US005821195A

United States Patent [19]
Sandbrink et al.

[11] Patent Number: 5,821,195
[45] Date of Patent: *Oct. 13, 1998

[54] SEQUENTIAL APPLICATION METHOD FOR ENHANCING GLYPHOSATE HERBICIDAL EFFECTIVENESS WITH REDUCED ANTAGONISM

[75] Inventors: Joseph J. Sandbrink, Des Peres; James M. Warner, University City; Daniel R. Wright, St. Louis; Paul C. C. Feng, Ellisville, all of Mo.

[73] Assignee: Monsanto Company, St. Louis, Mo.

[*] Notice: This patent issued on a continued prosecution application filed under 37 CFR 1.53(d), and is subject to the twenty year patent term provisions of 35 U.S.C. 154(a)(2).

[21] Appl. No.: 698,883

[22] Filed: Aug. 16, 1996

[51] Int. Cl.$^6$ .................................................. A01N 57/02
[52] U.S. Cl. ............................................................ 504/206
[58] Field of Search ............................................. 504/206

[56] References Cited

U.S. PATENT DOCUMENTS

| | | | |
|---|---|---|---|
| 2,732,398 | 1/1956 | Brice et al. | 260/503 |
| 2,764,602 | 9/1956 | Ahlbrecht | 260/404.5 |
| 2,764,603 | 9/1956 | Ahlbrecht | 260/404.5 |
| 2,803,656 | 8/1957 | Ahlbrecht et al. | 260/556 |
| 2,809,990 | 10/1957 | Brown | 260/534 |
| 3,147,064 | 9/1964 | Brown et al. | 8/116.2 |
| 3,255,131 | 6/1966 | Ahlbrecht et al. | 260/22 |
| 3,450,755 | 6/1969 | Ahlbrecht | 260/556 |
| 3,505,377 | 4/1970 | Morehouse | 260/448.2 |
| 3,723,512 | 3/1973 | Niederprum et al. | 260/501.15 |
| 3,799,758 | 3/1974 | Franz | 71/86 |
| 3,980,688 | 9/1976 | Litteral et al. | 260/448.8 R |
| 4,000,168 | 12/1976 | Bertocchio et al. | 260/404.5 |
| 4,042,522 | 8/1977 | Falk | 252/8.05 |
| 4,069,158 | 1/1978 | Bertocchio et al. | 252/3 |
| 4,069,244 | 1/1978 | Mueller | 260/501.12 |
| 4,090,967 | 5/1978 | Falk | 252/3 |
| 4,160,776 | 7/1979 | Scardera et al. | 260/448.8 |
| 4,161,590 | 7/1979 | Mueller | 544/159 |
| 4,161,602 | 7/1979 | Mueller | 546/335 |
| 4,226,794 | 10/1980 | Scardera et al. | 556/443 |
| 4,313,847 | 2/1982 | Chasin et al. | 252/356 |
| 4,337,168 | 6/1982 | Scardera et al. | 252/312 |
| 4,405,531 | 9/1983 | Franz | 260/501.12 |
| 4,431,789 | 2/1984 | Okazaki et al. | 528/18 |
| 4,481,365 | 11/1984 | Förster et al. | 556/442 |
| 4,488,896 | 12/1984 | Lamb et al. | 71/92 |
| 4,506,831 | 3/1985 | Ghyczy et al. | 239/10 |
| 4,629,499 | 12/1986 | Felix et al. | 71/100 |
| 4,695,313 | 9/1987 | Bordas et al. | 71/100 |
| 4,840,659 | 6/1989 | Franz | 71/86 |
| 4,902,333 | 2/1990 | Quimby, Jr. | 71/79 |
| 5,043,464 | 8/1991 | Yamamoto | 556/437 |
| 5,104,647 | 4/1992 | Policello | 514/772 |
| 5,147,444 | 9/1992 | Decor et al. | 71/86 |
| 5,187,184 | 2/1993 | Lovell | 514/406 |
| 5,246,936 | 9/1993 | Treacy et al. | 514/256 |
| 5,332,714 | 7/1994 | Albrecht et al. | 504/116 |
| 5,463,180 | 10/1995 | Gednalske et al. | 504/323 |
| 5,489,569 | 2/1996 | Bryant et al. | 504/166 |
| 5,504,054 | 4/1996 | Murphy | 504/116 |
| 5,510,316 | 4/1996 | Charudattan et al. | 504/117 |
| 5,527,760 | 6/1996 | Rensing et al. | 504/100 |
| 5,543,383 | 8/1996 | Parker et al. | 504/116 |
| 5,558,806 | 9/1996 | Policello et al. | 252/355 |
| 5,561,100 | 10/1996 | Hagen et al. | 504/130 |
| 5,571,772 | 11/1996 | Willms et al. | 504/106 |
| 5,580,841 | 12/1996 | Chan et al. | 504/206 |

FOREIGN PATENT DOCUMENTS

| | | | |
|---|---|---|---|
| 38389/89 | 5/1991 | Australia | A01N 25/30 |
| 0 394 211 | 10/1990 | European Pat. Off. | A01N 25/14 |
| 0 427 991 A | 5/1991 | European Pat. Off. | A01N 25/28 |
| WO 96/05721 | 2/1996 | WIPO | A01G 7/06 |

OTHER PUBLICATIONS

Sundaram, A. et al. "Effect of Glycerol on Spreading and Drying of Vision(R) Droplets containing Silwet(R) L–77: Relevance to Rainfastness and Herbicidal Activity of Glyphosate on Trembling Aspen (Populus tremuloides Michx.)" *Journal of Environmental Science and Health*, vol. B31(4), pp. 901–912 (1996).

Osi Specialties, Inc., "Silwet® Surfactants," pp. 1–20, Jun. 1994.

Peter J. G. Stevens, "Organosilicone Surfactants as Adjuvants for Agrochemical," *Pesticide Science*, vol. 38, pp. 103–122, 1993.

Robyn E. Gaskin and Peter J. G. Stevens, "Antagonism of the Foliar Uptake of Glyphosate into Grasses by Organosilicone Surfactants. Part 1: Effects of Plant Species, Formulation, Concentrations and Timing of Application," *Pesticide Science*, vol. 38, pp. 185–192, 1993.

Photographs of Truck–Mounted Double Boom Spray Apparatus, observed in Trenton, Missouri May 1997.

Osi Specialties, Inc., "Bibliography of Silwet® Organosilicone Surfactants as Agricultural Adjuvants," Mar. 1996.

R. K. Yokomi, D. R. Jimenez, L. S. Osborne and J. P. Shapiro, "Comparison of Silverleaf Whitefly Induced and Chlormequat Chloride Induced Leaf Silvering in *Cucurbita pepo*," *Plant Disease*, vol. 79, No. 9, pp. 950–955, Sep. 1995.

(List continued on next page.)

*Primary Examiner*—S. Mark Clardy
*Attorney, Agent, or Firm*—James C. Forbes; Arnold, White & Durkee

[57] ABSTRACT

A novel herbicidal method is provided wherein plants are first treated with a glyphosate herbicide and then sequentially treated with a liquid accession agent which provides improved herbicidal effectiveness such that plants are controlled with lower rates of the applied herbicide. Sequential application has been demonstrated to reduce the antagonism to herbicidal effectiveness that may be exhibited when the accession agent is added to the herbicide in a tank mix or coformulation. Typical accession agents employed in the disclosed method include a class of surfactants known as superwetting agents, such as certain silicone-based and fluorocarbon-based surfactants.

60 Claims, No Drawings

OTHER PUBLICATIONS

K. D. Klein, S. Wilkowski and J. Selby, "Silane Surfactants—Novel Adjuvants for Agricultural Applications," *Proceedings 4th International Symposium of Adjuvants for Agrochemicals*, pp. 27–31, Oct. 1995.

L. L. Foloni, "Adjuvant Effects on Sulphosate and Glyphosate for Control of Red–Rice in Rice," *Proc. Brighton Crop Protection Conference—Weeds*, pp. 743–746, 1995.

George A. Policello, Peter J. G. Stevens, W. Alison Forster and Gerald J. Murphy, "The Influence of pH on the Performance of Organosilicon Surfactants," In *Pesticide Formulation and Application Systems:* 14th vol., pp. 313–317, ASTM Spec. Tech. Publ., 1995.

P. J. G. Stevens, J. C. Caseley and C. Bond, "Organosilicones as Adjuvants for Graminicides," *Proc. Brighton Crop Protection Conference—Weeds*, pp. 757–762, 1995.

P. Kudsk and S.K. Mathiassen, "Effects of Broadleaf Herbicides on Imazamethabenz–methyl Performance on Wild Oat (*Avena fatua* L.)," *Weed Research*, vol. 34, pp. 251–263, 1994.

Frank C. Roggenbuck, Richard F. Burow and Donald Penner, "Relationship of Leaf Position to Herbicide Absorption and Organosilicone Adjuvant Efficacy," *Weed Technology*, vol. 8, No. 3, pp. 582–585, Jul.–Sep. 1994.

John W. Leung, "A Fluorometric Method to Determine Rainfastness, Volatilization and Photostability of Glyphosate from Glass Slides, After Application of Vision® with Two Adjuvants," *J. Environ. Sci. Health*, vol. B29, No. 2, pp. 341–363, 1994.

W. A. Forster and J. A. Zabkiewicz, "Effect of an Organosilicone Surfactant on Spray Drop Adhesion and Retention by Pea (*Pisum sativum*) Leaf Surfaces," *Proc. 47th New Zealand Weed and Pest Control Conference*, pp. 387–391, 1994.

P. J. G. Stevens, J. T. S. Walker, P. W. Shaw and D. M. Suckling, "Organosilicone Surfactants: Tools for Horticultural Crop Protection," *Proc. Brighton Crop Protection Conference—Pests and Diseases*, pp. 755–760, 1994.

F. Dastgheib, R. J. Field and H. Searle, "Surfactant Effects on the Uptake of Different Herbicides by Gorse," *Proc. 47th New Zealand Weed and Pest Control Conference*, pp. 392–396, 1994.

Rosalind D. Buick, Graeme D. Buchan and Roger J. Field, "The Role of Surfact Tension of Spreading Droplets in Absorption of a herbicide Formulation via Leaf Stomata," *Pesticide Science*, vol. 38, pp. 227–235, 1993.

A. D. Baylis and C. A. Hart, "Varying Responses Among Weed Species to Glyphosate–Trimesiumin the Presence of an Organosilicone Surfactant," *Proc. Brighton Crop Protection Conference—Weeds*, pp. 1331–1336, 1993.

Robyn E. Gaskin and Peter J. G. Stevens, "Antagonism of the Foliar Uptake of Glyphosate into Grasses by Organosilicone. Part 2: Effects of Surfactant Structure and Glycerol Addition," *Pesticide Science*, vol. 38, pp. 193–200, 1993.

Jerzy A. Zabkiewicz, Peter J.G. Stevens, W. Allison Forster and Kevin D. Steele, "Foliar Uptake of Organosilicone Surfactant Oligomers into Bean Leaf in the Presence and Absence of Glyphosate," *Pesticide Science*, vol. 38, pp. 135–143, 1993.

Frank C. Roggenbuck, Donald Penner, Richard F. Burow and Bryan Thomas, "Study of the Enhancement of Herbicide Activity and Rainfastness by an Organosilicone–Adjuvant Utilizing Radiolabeled Herbicide and Adjuvant," *Pesticide Science*, vol. 37, pp. 121–125, 1993.

J. M. Balneaves, R. E. Gaskin and J. A. Zabkiewicz, "The Effect of Varying Rates of Glyphosate and an Organosilicone Surfactant on the Control of Gorse," *Aspects of Applied Biology*, vol. 122, pp. 531–536, 1993.

B. H. Rohitha, R. E. Gaskin, T. Hartley and A. K. Karl, "Evaluation of Silwet L–77 for Postharvest Disinfestation of Thrip in Asparagus," *Proc. 45th New Zealand Weed and Pest Control Conference*, pp. 17–20, 1992.

Hans de Ruiter, Esther Meinen and Monique A. M. Verbeek, "Influence of the Type and Concentration of Surfactant on Glyphosate Absorption; Relevance of Drop Spreading and Drying Time," In *Adjuvants for Agrochemicals*, ed. C. L. Foy, Chapter 8, pp. 109–116, CRC Press, Boca Raton, Florida, 1992.

Joseph H. Combellack, A. McShane and Robert G. Richardson, "The Influence of Adjuvants on the Performance of A Glyphosate/2,4–DMixture," In *Adjuvants for Agrochemicals*, ed. C. L. Foy, Chapter 29, pp. 303–310, CRC Press, Boca Raton, Florida, 1992.

E. D. Goddard and K. P. A. Padmanabhan, "A Mechanistic Study of the Wetting, Spreading, and Solution Properties of Organosilicone Surfactants," In *Adjuvants for Agrochemicals*, ed. C. L. Foy, Chapter 35, pp. 373–383, CRC Press, Boca Raton, Florida, 1992.

Peter J. G. Stevens Robyn E. Gaskin, Sung–Ok Hong and Jerzy A. Zabkiewicz, "Pathways and Mechanisms of Foliar Uptake as Influenced by Surfactants," In *Adjuvants for Agrochemicals*, ed. C. L. Foy, Chapter 36, pp. 385–398, CRC Press, Boca Raton, Florida, 1992.

Peter J. G. Stevens, Jerzy A. Zabkiewicz, Jonathan H. Barran, K. R. Klitscher and Fiona Ede "Spray Formulation with Silwet® Organosilicone Surfactants," In *Adjuvants for Agrochemicals*, ed. C. L. Foy, Chapter 37, pp. 399–403, CRC Press, Boca Raton, Florida, 1992.

Robyn E. Gaskin and Jerzy A. Zabkiewicz, "Effect of Plant Age and Adjuvant on the Foliar Penetration and Translocation of Glyphosate in Pampas Grass (*Cortaderia selloana*)," In *Adjuvants for Agrochemicals*, ed. C. L. Foy, Chapter 38, pp. 405–409, CRC Press, Boca Raton, Florida, 1992.

Roger J. Field, Nicole N. Dobson and Lynnore J. Tisdall, "Species–SpecificSensitivity to Organosilicone Surfactant–Enhancementof Glyphosate Uptake," In *Adjuvants for Agrochemicals*, ed. C. L. Foy, Chapter 40, pp. 423–431, CRC Press, Boca Raton, Florida 1992.

Charles W. Coggins, Jr., Gilbert L. Henning and Michael F. Anthony, "Possible Methods to Increase Efficacy of Gibberellic Acid Applied to Navel Orange Trees," In *Adjuvants for Agrochemicals*, ed. C. L. Foy, Chapter 55, pp. 567–572, CRC Press, Boca Raton, Florida, 1992.

Walter Steurbaut, H. S. Megahed, G. Van Roey, T. Melkebeke and W. Dejonckheere, "Influence of Surfactant–Oil Combinations on the Activity of Foliar–Applied Fungicides," In *Adjuvants for Agrochemicals*, ed. C. L. Foy, Chapter 61, pp. 623–635, CRC Press, Boca Raton, Florida, 1992.

Siyuan Tan and Garvin D. Crabtree, "Effects of Nonionic Surfactants on Cuticular Sorption and Penetration of 2,4–Dichlorophenoxy Acetic Acid," *Pesticide Science*, vol. 35, pp. 299–303, 1992.

Robyn E. Gaskin and Peter J. Holloway, "Some Physicochemical Factors Influencing Foliar Uptake Enhancement of Glyphosate–mono(isopropylammonium)by Polyoxyethylene Surfactants," *Pesticide Science*, vol. 34, pp. 195–206, 1992.

R. E. Gaskin and J. A. Zabkiewicz, "A Comparison Between Two Commercial Organosilicone Surfactants; Their Effect on the Uptake and Translocation of Glyphosate in Gorse (*Ulex europaeus*)," *Proc. 44th New Zealand Weed and Pest Control Conference*, pp. 109–111, 1991.

Peter J. G. Stevens, Robyn E. Gaskin, Sung–Ok Hong and Jerzy A. Zabkiewicz, "Contributions of Stomatal Infiltration and Cuticular Penetration to Enhancements of Foliar Uptake by Surfactants," *Pesticide Science*, vol. 33, pp. 371–382, 1991.

R. J. Field and L. J. Tisdall, "The Mechanism of Organosilicone Surfactant–Induced Antagonism of Glyphosate Uptake," *Proc. 9th Australian Weeds Conference*, pp. 332–335, Aug. 6–10, 1990.

P. J. G. Stevens and J. A. Zabkiewicz, "New Formulation Technology—Silwet® Organosilicone Surfactants Have Physical and Physiological Properties which Enchance the Performance of Sprays," *Proc. 9th Australian Weeds Conference*, pp. 327–331, Aug. 6–10, 1990.

R. D. Buick, R. J. Field and A. B. Robson, "The Effects of Silwet L77 on Triclopyr Absorption," *Proc. 43rd New Zealand Weed and Pest Control Conference*, pp. 174–177, 1990.

Jörg Schönherr and Hubert Bauer, "Analysis of Effects of Surfactants on Permeability of Plant Cuticles," In *Adjuvants and Agrochemicals vol. 1: Mode of Action and Physiological Activity*, ed. P. N. P. Chow, C. A. Grant, A. M. Hinshalwood and E. Simmundsson, Chapter 2, pp. 17–35, CRC Press, Boca Raton, Florida, 1989.

Alam Sundaram, "Influence of Two Polymeric Adjuvants on Bioavailability of Glyphosate in Vision® Formulation: Relevance to Rainwashing of Deposits from Foliar Surfaces," In *Adjuvants and Agrochemicals vol. 1: Mode of Action and Physiological Activity*, ed. P .N. P. Chow, C. A. Grant, A. M. Hinshalwood and E. Simmundsson, Chapter 5, pp. 77–85, CRC Press, Boca Raton, Florida, 1989.

R. E. Gaskin and R. C. Kirkwood, "The Effect of Certain Nonionic Surfactants on the Uptake and Translocation of Herbicides in Bracken (*Pteridium aquilinum* [L.] Kuhn)," In *Adjuvants and Agrochemicals, vol. 1: Mode of Action and Physiological Activity*, ed. P. N. P. Chow, C. A. Grant, A. M. Hinshalwood and E. Simmundsson, Chapter 13, pp. 129–139, CRC Press, Boca Raton, Florida, 1989.

J. A. Zabkiewicz and R. E. Gaskin, "Effect of Adjuvants on Uptake and Translocation of Glyphosate in Gorse (*Ulex europaeus* L.)," In *Adjuvants and Agrochemicals, vol. 1: Mode of Action and Physiological Activity*, ed. P. N. P. Chow, C. A. Grant, A. M. Hinshalwood and E. Simmundsson, Chapter 14, pp. 141–149, CRC Press, Boca Raton, Florida, 1989.

R. E. Gaskin and J. A. Zabkiewicz, "The Effect of Surfactants on the Uptake and Translocation of Glyphosate in Yorkshire Fog," *Proc. 42nd New Zealand Weed and Pest Control Conference*, pp. 128–131, 1989.

Chris M. Boerboom and Donald L. Wyse, "Influence of Glyphosate Concentration on Glyphosate Absorption and Translocation in Canada Thistle (*Cirsium arvense*)," Weed Science, vol. 36, No. 3, pp. 291–295, May 1988.

H. de Ruiter, M. A. M. Verbeek and A. J. M. Uffing, "Mode of Action of a Nonionic and a Cationic Surfactant in Relation to Glyphosate," In *Pesticide Fomulations: Innovations and Developments*, ed. B. Cross and H. B. Scher, Chapter 5, pp. 44–55, American Chemical Society, Washington DC, 1988.

J. A. Zabkiewicz, D. Coupland and F. Ede, "Effects of Surfactants on Droplet Spreading and Drying Rates in Relation to Foliar Uptake," In *Pesticide Fomulations: Innovations and Developments*, ed. B. Cross and H. B. Scher, Chapter 7, pp. 77–89, American Chemical Society, Washington DC, 1988.

Peter J. G. Stevens, Edward A. Baker and Nicholas H. Anderson, "Factors Affecting the Foliar Absorption and Redistribution of Pesticides. 2. Physicochemical Properties of the Active Ingredient and the Role of Surfactant," *Pesticide Science*, vol. 24, pp. 31–53, 1988.

Roger J. Field and Nicholas G. Bishop, "Promotion of Stomatal Infiltration of Glyphosate by an Organosilicone Surfactant Reduces the Critical Rainfall Period," *Pesticide Science*, vol. 24, pp. 55–62, 1988.

Michael R. Blumhorst and George Kapusta, "Mefluidide as an Enhancing Agent for Postmergence Broadleaf Herbicides in Soybeans," *Weed Technology*, vol. 1, No. 2, pp. 149–153, Apr. 1987.

R. J. Field and N. G. Bishop, "The Mechanism of Action of Silwet L77$^R$ in Improving the Performance of Glyphosate Applied to Perennial Ryegrass," *Proc. 8th Australian Weeds Conference*, pp. 411–415, 1987.

Stewart L. Sherrick, Harvey A. Holt and F. Dan Hess, "Absorption and Translocation of MON 0818 Adjuvant in Field Bindweed (*Convolvulus arvensis*)," *Weed Science*, vol. 34, No. 6, pp. 817–823, Nov. 1986.

John F. Ahrens, "Postemergence Herbicides for Apples and Grapes," *Proc. Northeastern Weed Science Society 40th Annual Meeting*, p. 160, 1986.

J. S. Goudey, M. Dale and J. Hoddinott, "The Effects of Oil Spill Chemicals on Transpiration, $CO_2$ Exchange, and Cuticular Structure in Salix interior," *Can. J. Bot.*, vol. 63, pp. 2340–2344, 1985.

J. C. Caseley and D. Coupland, "Environmental and Plant Factors Afecting Glyphosate Uptake, Movement, and Activity," In *The Herbicide Glyphosate*, ed. E. Grossbard and D. Atkinson, Chapter 7, pp. 92–123, Butterworths, London, 1985.

D. J. Turner, "Effects on Glyphosate Performance of Formulation, Additives and Mixing with Other Herbicides," In *The Herbicide Glyphosate*, ed. E. Grossbard and D. Atkinson, Chapter 15, pp. 221–240, Butterworths, London, 1985.

Edward A. Baker, Grace M. Hunt and Peter J. G. Stevens, "Studies of Plant Cuticle and Spray Droplet Interactions: a Fresh Approach," *Pesticide Science*, vol. 14, pp. 645–658, 1983.

N. G. Bishop and R. J. Field, "Improved Performance of Glyphosate in the Full Season Control of Perennial Ryegrass," *Aspects of Applied Biology*, vol. 4, pp. 363–370, 1983.

J. B. Wyrill III and O. C. Burnside, "Glyphosate Toxicity to Common Milkweed and Hemp Dogbane as Influenced by Surfactants," *Weed Science*, vol. 25, No. 3, pp. 275–287, May 1977.

F. A. Qureshi and W. H. Vanden Born, "Spray Droplet Distribution and Herbicide Uptake in Sequential Applications of Diclofop–methyl and MCPA for Weed Control in Barley," *Can. J. Plant Sci.*, vol. 89, pp. 93–98, Jan. 1979.

R. D. Buick and R. J. Field, "The Mechanism of Organosilicone Surfactant–Induced Uptake of Amine and Ester Formulations of Triclopyr," Proceedings 1st International Weed Control Congress, Melbourne, vol. 2, pp. 103–105, 1992.

SEQUENTIAL APPLICATION METHOD FOR ENHANCING GLYPHOSATE HERBICIDAL EFFECTIVENESS WITH REDUCED ANTAGONISM

This invention relates to a method of enhancing the effectiveness of herbicidal compositions, in particular compositions comprising N-phosphonomethylglycine ("glyphosate") and its herbicidal derivatives. Specifically, the present invention relates to the use of a class of liquid agents (referred to herein as "accession agents") to enhance the herbicidal effectiveness of glyphosate on a variety of plant species, but without the antagonistic effect such agents may otherwise exhibit when used with glyphosate on certain plant species by methods previously described in the art. It has been found that sequential application of an accession agent (rather than application concurrent with glyphosate as for example in a tank mix) provides unique enhancement of the effectiveness of pre-applied glyphosate compositions on and in the foliar parts of plants. Such sequential treatment has been found to enhance the effectiveness of glyphosate and its herbicidal derivatives on many species, with minimal antagonism on other species. More particularly, this invention relates to a method of enhancing the herbicidal effectiveness of compositions comprising a salt of N-phosphonomethylglycine.

BACKGROUND OF THE INVENTION

Foliar-applied herbicides, such as glyphosate, are typically formulated with surfactants, so that when water is added, the resulting sprayable composition will more easily and effectively cover the foliage (e.g., the leaves or other photosynthesizing organs) of plants. Thus, for example, glyphosate has been formulated with surfactants such as polyoxyalkylene-type surfactants including, among other surfactants, polyoxyalkylene alkylamines. Thus, for example commercial formulations of glyphosate herbicide marketed under the trademark ROUNDUP® have been formulated with such a polyoxyalkylene alkylamine, in particular a polyethoxylated tallowamine, identified as MON-0818.

It is also known to formulate glyphosate herbicide with additional surfactants. For example, European Patent Specification No. 0 394 211 B1 discloses solid granular formulations of glyphosate containing organosilicone wetting agents or fluoro-organic wetting agents.

Some commercial formulations of glyphosate herbicide have been formulated with such additional surfactants, including a particular group of polyoxyalkylene polysiloxane surfactants, such as the commercial organosilicone surfactant Silwet L-77, which has been reported to affect the foliar absorption of glyphosate by plants. A number of studies relating to the use of Silwet L-77 with glyphosate have been published. It should be noted that to date, these surfactants have generally been combined with glyphosate either in a commercial concentrate (herein referred to as a "coformulation"), or in a diluted mixture that is prepared from separate glyphosate and surfactant compositions prior to use in the field (i.e., a tank mix). Coformulations and tank mixes, and methods for applying them, are herein distinguished from the "sequential application" methods that are the subject of this invention.

A foliar uptake study of glyphosate herbicide, wherein an organosilicone (Silwet L-77) was applied together with glyphosate to simulate a tank mix, is reported by Field & Bishop in Pestic. Sci., 1988, Vol. 24, pp. 55–62. When these tank mix compositions were applied to the adaxial leaf surfaces of perennial ryegrass plants, complete surface wetting was observed at Silwet L-77 concentrations of 0.1–0.5% by volume. Through timed experiments wherein radio-labeled glyphosate was applied to the leaves followed by washing of the leaves, it was concluded that use of Silwet L-77 provides a reduced critical rain-free period after application because of an enhanced rate of glyphosate uptake. Rapid uptake was observed into stomata of the plants treated with the tank mix. Visual confirmation of stomatal uptake was confirmed by dye studies. However, these workers found Silwet L-77 antagonistic to glyphosate uptake over a 48 hour period. Herbicidal effects were reported in terms of tiller re-growth (expressed as percentage of tiller number at time of glyphosate application). Stevens et al, Pestic. Sci., 1991, Vol. 33, pp. 371–82, note an enhancement of herbicide uptake over a 0–6 hour period for tank mixes of glyphosate and Silwet L-77.

Another study of the effects of Silwet L-77 upon the foliar uptake of glyphosate herbicide is reported in an article by Gaskini & Stevens entitled "Antagonism of the Foliar Uptake of Glyphosate into Grasses by Organosilicone Surfactants. Part 1: Effects Of Plant Species, Formulation, Concentrations, and Timing of Application," Pestic. Sci., 1993, Vol. 38, pp. 185–92. In this study, radio-labeled glyphosate (specifically the isopropylammonium "IPA" salt) was utilized to determine the uptake of herbicide in wheat plants. The authors measured the foliar uptake when Silwet L-77 was applied before (pretreatment), during (i.e., in a tank mix), and after (post-treatment) application of the glyphosate herbicide to the plants. Pretreatment of the plants with Silwet L-77 reduced the uptake of the glyphosate by the foliage over the course of the study and failed substantially to increase even the initial rate of uptake of glyphosate into the plant. Both simultaneous (i.e., tank mix) and post-treatment of the plants with Silwet L-77 at 4 and 8 hours after herbicide application were found to increase the initial rate of uptake of glyphosate; but these workers concluded that "the initial enhancements provided by both simultaneous and sequential application of Silwet L-77 slowed down rapidly thereafter in all treatments." The article reports no measurements of herbicidal effectiveness for any species. The article states that Silwet L-77 may be beneficial as a spray (i.e., a tank mix) adjuvant if rain falls after its application but not in the absence of rain. Further study of the antagonism of glyphosate uptake by Silwet L-77 is reported by Gaskin & Stevens, "Antagonism of the Foliar Uptake of Glyphosate into Grasses by Organosilicone Surfactants. Part 2: Effects of Surfactant Structure and Glycerol Addition", Pestic. Sci., 1993, Vol. 38, pp. 193–200. An extensive review of 160 references relating to the use of organosilicones as adjuvants for agrochemicals was provided by Stevens, Pestic. Sci., 1993, Vol. 38, pp. 103–22. Although Stevens discusses extensively work relating to coformulations or tank mixes of organosilicones with, e.g., herbicides, there is no discussion of work relating to sequential application of these materials.

The effects of Silwet L-77 on the foliar uptake of other herbicides has been investigated. Buick et al., Pestic. Sci., 1993, Vol. 38, pp. 227–35, report increases in uptake of triclopyr triethylamine in field bean over time periods of one hour and six hours by inclusion of Silwet L-77 in a simulated tank mix. These workers posit infiltration of foliar stomata to explain this effect. Other workers have questioned the significance of stomatal infiltration to the operation of organosilicone surfactants. Roggenbuck et al, Weed Tech., 1994, Vol. 8, pp. 582–85, conclude there is no relationship between the number of stomata covered and the degree to which herbicide uptake is influenced by addition of Sylgard 309, an organosilicone surfactant.

Antagonistic effects with respect to the herbicidal effectiveness or uptake of glyphosate have been reported in the following species for tank mixes containing Silwet L-77:

colonial bentgrass (*Agrostis tenuis*)
downy broom (*Bromus tectorum*)
orchardgrass (*Dactylis glomerata*)
crabgrass (*Digitaria sp.*)
barnyardgrass (*Echinochloa crus-galli*)
goosegrass (*Eleusine indica*)
quackgrass (*Elymus repens*)
wild poinsettia (*Euphorbia heterophylla*)
common velvetgrass (*Holcus lanatus*)
dallisgrass (*Paspalum dilatatum*)
prostrate knotweed (*Polygonum aviculare*)
green foxtail (*Setaria viridis*)
johnsongrass (*Sorghum halepense*)
wheat (*Triticum aestivum*)
cocklebur (*Xanthium pennsylvanicum*)

See Gaskin & Stevens, *Pestic. Sci.*, 1993, Vol. 38, pp. 185–92; Baylis & Hart, *Brighton Crop Protection Conference*, 1993, pp. 1331–36; Field & Tisdall, *Ninth Australian Weed Conference*, 1990, pp. 332–35; Australian Patent Publication No. 38389/89.

We have observed similar antagonistic effects in the following species:

velvetleaf (*Abutilon theophrasti*)
redroot pigweed (*Amaranthus retroflexus*)
wild oat (*Avena fatua*)
broadlead signalgrass (*Brachiaria platyphylla*)
canola (*Brassica napus*)
downy broom (*Bromus tectorum*)
sicklepod (*Cassia obtusifolia*)
common lambsquarter (*Chenopodium album*)
barnyardgrass (*Echinochloa crus-galli*)
redstem filaree (*Erodium cicutarium*)
cutleaf geranium (*Geranium dissectum*)
soybean (*Glycine max*)
little barley (*Hordeum pusillum*)
pitted morning-glory (*Ipomoea lacunosa*)
annual ryegrass (*Lolium multiflorum*)
annual bluegrass (*Poa annua*)
wild buckwheat (*Polygonum convolvulus*)
cutleaf evening primrose (*Primula trientalis*)
curly dock (*Rumex crispus*)
hemp sesbania (*Sesbania exaltata*)
prickly sida (*Sida spinosa*)
wild mustard (*Sinapis arvensis*)
johnsongrass (*Sorghum halepense*)
wheat (*Triticum aestivum*)

Blumhorst & Kapusta have investigated sequential and tank mix applications of plant growth regulators (specifically, mefluidide) with herbicides. *Weed Technology*, 1987, Vol. 1, pp. 149–53. A study of the sequential application of herbicide materials is reported by Qureshi & VandenBorn, *Canadian Journal of Plant Science*, 1979, Vol. 59, pp. 93–98.

Because surfactants may enhance herbicidal effects when coformulated with or added in a tank mix to herbicidal compositions, numerous workers have studied the effects of various surfactants. One extensive study was conducted by Wyrill & Burnside and reported in *Weed Science*, 1977, Vol. 25, Issue 3 pp. 285–87. These investigators concluded that "the effectiveness of surfactant combinations was quite variable and difficult to predict. Therefore, the indiscriminate addition of surfactants into glyphosate spray mixtures which already contain a surfactant should be avoided." However, this study did not include any surfactant treatment that might be expected to induce stomatal infiltration. Another study of surfactant effects on glyphosate is set forth in Gaskin & Kirkwood, "The Effect of Certain Nonionic Surfactants on the Uptake and Translocation of Herbicides in Bracken," *Adjuvants and Agrochemicals*, 1989, Vol. 1, Chapter 13, pp. 129–39. In this study, surfactants (including Silwet L-77) are compared and rated for selected herbicides, based upon plant uptake and translocation measurements. Silwet L-77 was shown to be superior to two non-organosilicone surfactants for enhancing glyphosate uptake and translocation in bracken.

So many studies are reported in this area that OSi Specialties (a unit of Witco Corporation) has published a *Bibliography of Silwet Organosilicone Surfactants As Agricultural Adjuvants* (1996), which is indexed for computer searching. This reference lists hundreds of published studies of commercial organosilicone surfactants in agricultural applications. This bibliography is available to the public through the publisher's office in Tarrytown, N.Y.

Bishop & Field, *Aspects of Applied Biology*, 1983, Vol. 4, pp. 363–70, report that Silwet L-77 in tank mix enhanced the performance of glyphosate in field trials on perennial ryegrass. "Spectacular" leaf wetting was observed for tank mixes including 0.5% by volume Silwet L-77, indicating pronounced spreading of the herbicide over the foliar portions of the plant. Stevens et al. report in *Pestic. Sci.*, 1991, Vol. 33, pp. 371–82, that in vicia bean leaves, the stomatal infiltration of Silwet L-77 is antagonized by the surfactant coformulant in ROUNDUP® herbicide. Baylis & Hart have concluded that the effect of Silwet L-77 in tank mix on the herbicidal efficacy of glyphosate-trimesium (the trimethylsulfonium salt of glyphosate) varies with plant species, and could not be explained simply by stomatal infiltration. "Varying Response Among Weed Species to Glyphosate-Trimesium in the Presence of an Organosilicone Surfactant," *Brighton Crop Protection Conference*, 1993, pp. 1331–36.

Many have investigated the possible mechanisms of herbicide antagonism by Silwet L-77 and, therefore, the means to avoid it. As used herein, "antagonism" refers to a decrease in herbicidal effect when a material (such as Silwet L-77) is used in combination with the active herbicide; although it has been used in some of the literature cited herein to refer to a decrease in herbicide uptake or translocation. Australian Patent Application No. 38389/89 reports the use of tank mixed formulations of glyphosate and Silwet L-77, in combination with a humectant such as glycerin. An uptake investigation of similar formulations is reported by Field& Tisdall, published in the proceedings of the *Ninth Australian Weed Conference*, 1990, pp. 332–35. Glycerin was claimed to promote the uptake of glyphosate from formulations containing Silwet L-77. In this study, paspalum leaves were treated with formulations containing Silwet L-77, with and without glycerin. Pretreatment of the paspalum leaf surfaces with Silwet L-77 two hours prior to application of glyphosate stimulated uptake. Silwet L-77 tank mixed with glyphosate did not. These investigators stated that "glycerin does not appear to have a pronounced humectant effect and it is concluded that antagonism and its alleviation by glycerin involves specific leaf surface—solution interactions that are clearly species specific." They concluded that no stomatal infiltration occurred even at Silwet L-77 concentrations as high as 0.5% by volume.

From the numerous publications on the subject of formulating glyphosate with various surfactants, particularly organosilicone surfactants and others that can induce stomatal infiltration, it must be concluded that the effects observed vary with the plant species, herbicide, and surfactant. Tank mixed formulations containing Silwet L-77 (or other surfactants) may yield improved results on some species, but may antagonize the herbicidal effectiveness of glyphosate for others. This provides a disincentive to use surfactants like Silwet L-77, since multiple weed species are typically treated in the same field and the surfactant will likely prove antagonistic for at least some of the weed species present. The problem of herbicide antagonism for these surfactants over a variety of plant species has defied a practical solution—until now.

SUMMARY OF THE INVENTION

What has been discovered is a process that dramatically enhances the herbicidal effectiveness of glyphosate compositions. This process comprises a sequential application of: (1) a glyphosate composition to the foliage of a plant, followed by (2) a liquid accession agent selected to provide stomatal infiltration of liquid from the surface of the foliage. This sequential application yields a dramatic and unexpected result, in that it reduces or eliminates any antagonism that might be exhibited when the herbicide and accession agent are premixed and applied in admixture (i.e., in the standard "tank mix" processes). It has been discovered that for a spectrum of plant species, sequential application of these materials is superior to application in a tank mix. For those plant species for which tank-mixed glyphosate and accession agent (e.g., surfactant solution) are antagonistic, the antagonism is generally reduced and often eliminated. For those plant species for which the tank-mixed glyphosate and accession agent (e.g., surfactant solution) are not antagonistic, sequential application of these materials will produce a herbicidal effectiveness that generally does not differ significantly from that obtained with the tank mix and is sometimes superior to that obtained in a tank mix.

Accordingly, the invention may be described generally as a herbicidal method comprising the sequential steps of (a) contacting a plant with a herbicide comprising N-phosphonomethylglycine or a herbicidal derivative thereof and (b) thereafter contacting the plant with an accession agent whereby any antagonism to herbicidal effectiveness that would result from contacting the plant with a tank mix or coformulation of the herbicide and the accession agent is substantially reduced. The invention may also be generally described as a method for enhancing the herbicidal effectiveness of a herbicide for a plurality of plant species in a field. Such a method comprises the steps of (a) applying to the plurality of plant species in the field a herbicide comprising N-phosphonomethylglycine or a herbicidal derivative thereof and (b) thereafter applying to the plurality of plant species an accession agent, whereby the herbicidal effectiveness of the herbicide for at least one of the plurality of plant species is substantially enhanced. In addition, the invention may be generally described as a method for reducing the antagonism of an accession agent to the herbicidal effectiveness of a herbicide comprising N-phosphonomethylglycine or a herbicidal derivative thereof. Such a method comprises the steps of (a) applying the herbicide to a plant species for which the accession agent is antagonistic to the herbicidal effectiveness of the herbicide when tank mixed or coformulated therewith and (b) thereafter applying to the plant species an accession agent, whereby the herbicidal effectiveness of the herbicide is substantially preserved or enhanced for the plant species.

Further, the invention may also be generally described as a method for enhancing the yield of a field crop. Such a method comprises the steps of (a) planting a crop in a field, (b) substantially freeing the field of a weed species that would diminish the yield of the crop by (i) applying to weed species a herbicide comprising N-phosphonomethylglycine or a herbicidal derivative thereof and (ii) thereafter applying to the weed species an accession agent, whereby any antagonism to herbicidal effectiveness that would be exhibited by application of a tank mix or coformulation of the herbicide and the accession agent is substantially reduced, (c) allowing the crop to mature, and (d) harvesting the crop. In this method of enhancing the yield of a field crop, the order of the above steps may be altered, in which case a field for planting a crop is selected and, before the crop is planted in the field, the field is substantially freed of a weed species that would diminish the yield of the crop.

DETAILED DESCRIPTION OF THE INVENTION

The following sets forth in detail the novel method of the present invention, wherein the sequential application of a suitable accession agent, following the application of glyphosate reduces or eliminates the antagonism that might be obtained with conventional tank mix applications.

Glyphosate, Glyphosate Derivatives, and Herbicidal Compositions Thereof

The herbicide useful in the method of this invention is glyphosate (N-phosphonomethylglycine), a salt or ester thereof, or a compound which is converted to glyphosate in plant tissues or which otherwise provides glyphosate ion. Illustratively, glyphosate and its salts useful herein are disclosed in U.S. Pat. No. 3,799,758. Glyphosate salts that can be used according to this invention include (but are not restricted to) alkali metal, for example sodium and potassium, salts; ammonium salt; alkylamine, for example dimethylamine and isopropylamine, salts; alkylsulfonium, for example trimethylsulfonium, salt; and mixtures thereof. The herbicidal compositions sold by Monsanto Company as ROUNDUP® and ACCORD® contain the monoisopropylamine (IPA) salt of N-phosphonomethylglycine. The herbicidal compositions sold by Monsanto Company as ROUNDUP® DRY and RIVAL® contain the ammonium salt of N-phosphonomethylglycine. The herbicidal composition sold by Monsanto Company as ROUNDUP® GEOFORCE contains the monosodium salt of N-phosphonomethylglycine. The herbicidal properties of N-phosphonomethylglycine and its derivatives were first discovered by Franz, then disclosed and patented in U.S. Pat. No. 3,799,758, issued Mar. 26, 1974. A number of herbicidal salts of N-phosphonomethylglycine were patented by Franz in U.S. Pat. No. 4,405,531, issued Sept. 20, 1983. Both of these patents are hereby incorporated by reference.

Because the commercially most important herbicidal derivatives of N-phosphonomethylglycine are the salts of the acid, the glyphosate compositions useful in the present invention will be described in more detail with respect to such compounds. These salts are well known and include ammonium, alkylamine (such as isopropylamine (IPA) salt), alkali metal (such as the mono-, di-, and trisodium salts, and the mono-, di-, and tripotassium salts), alkylsulfonium (such as methylsulfonium, dimethylsulfonium and trimethylsulfonium salts), and sulfoxonium salts. Salts of N-phosphonomethylglycine are commercially significant because they are water soluble. Most of the ammonium, alkylamine and alkali metal salts are highly water soluble, thereby allowing for highly concentrated solutions that may be diluted at the site of use. In accordance with this invention, an aqueous solution of glyphosate, or a salt of the same, is applied to the foliage of plants, followed by treatment of the same foliage with a suitable amount of an accession agent, selected in accordance with this invention.

"Herbicidal effectiveness," as used herein, refers to the observable (and desired) degree of control, which is inclusive of the actions of (1) killing, (2) inhibiting growth, reproduction or proliferation, and (3) removing, destroying, or otherwise diminishing the occurrence and activity of plants, and is applicable to any of these actions, or any combinations thereof. The data set forth herein report "inhibition" as a percentage following the standard procedure in the art which reflects a visual assessment of plant mortality and growth reduction by comparison with untreated plants, made by technicians specially trained to make and record such observations. In all cases, a single technician makes all assessments of percent inhibition within any one experiment or trial. Such measurements are relied upon and regularly reported by Monsanto Company in the course of its herbicide business. Typically, adequate herbicidal effectiveness for commercial use corresponds to about 85% inhibition. Over two decades of glyphosate use and published studies relating to such use have provided abundant information from which a weed control practitioner may select glyphosate application rates that are herbicidally effective on particular species at particular growth stages in particular environmental conditions.

Herbicidal compositions of glyphosate or derivatives thereof are used to control a very wide variety of plant species worldwide. Particularly important genera for which glyphosate compositions are used are exemplified without limitation by the following:

Annual broadleaves:
velvetleaf (*Abutilon theophrasti*)
pigweed (*Amaranthus spp.*)
buttonweed (*Borreria spp.*)
oilseed rape, canola, indian mustard, etc. (*Brassica spp.*)
commelina (*Commelina spp.*)
filarce (*Erodium spp.*)
sunflower (*Helianthus spp.*)
morningglory (*Ipomoea spp.*)
kochia (*Kochia scoparia*)
mallow (*Malva spp.*)
wild buckwheat, smartweed, etc. (*Polygonum spp.*)
purslane (*Portulaca spp.*)
russian thistle (*Salsola spp.*)
sida (*Sida spp.*)
wild mustard (*Sinapis arvensis*)
cocklebur (*Xanthium spp.*)
Annual narrowleaves:
wild oat (*Avena fatua*)
carpetgrass (*Axonopus spp.*)
downy broom (*Bromus tectorum*)
crabgrass (*Digitaria spp.*)
barnyardgrass (*Echinochloa crus-galli*)
goosegrass (*Eleusine indica*)
annual ryegrass (*Lolium multiflorum*)
rice (*Oryza sativa*)
ottochloa (*Ottochloa nodosa*)
bahiagrass (*Paspalum notatum*)
canarygrass (*Phalaris spp.*)
foxtail (*Setaria spp.*)
wheat (*Triticum aestivum*)
corn (*Zea mays*)
Perennial broadleaves:
mugwort (*Artemisia spp.*)
milkweed (*Asclepias spp.*)
canada thistle (*Cirsium arvense*)
field bindweed (*Convolvulus arvensis*)
kudzu (*Pueraria spp.*)
Perennial narrowleaves:
brachiaria (*Brachiaria spp.*)
bermudagrass (*Cynodon dactylon*)
yellow nutsedge (*Cyperus esculentus*)
purple nutsedge (*C. rotundus*)
quackgrass (*Elymus repens*)
lalang (*Imperata cylindrica*)
perennial ryegrass (*Lolium pesenne*)
guineagrass (*Panicum maximum*)
dallisgrass (*Paspalum dilatatum*)
reed (*Phragmites spp.*)
johnsongrass (*Sorghum halepense*)
cattail (*Typha spp.*)
Other perennials:
horsetail (*Equisetum spp.*)
bracken (*Pteridium aquilinum*)
blackberry (*Rubus spp.*)
gorse (*Ulex europaeus*)

The method of the present invention may be useful on any of the above species.

Accession Agents

While many of the accession agents of this invention are aqueous solutions of compounds known in the art as "surfactants," not all aqueous surfactant solutions perform as accession agents according to the invention. It has been determined that a property common to all accession agents as defined herein, whether or not they comprise a surfactant, is that they are capable of infiltrating the internal voids of a leaf of the plant species to be treated by the method of the invention, primarily via the stomata. This property is referred to herein as "stomatal infiltration." Although this property is important to determining whether a particular material will perform as an accession agent in the method of the present invention, it is not known whether the property of stomatal infiltration plays any part in the mechanism by which accession agents of the invention provide their surprising benefits in enhancing herbicide effectiveness while reducing antagonism.

The accession agents of this invention must be introduced as a flowable, bulk material, such as a liquid (e.g., an oil or an aqueous surfactant solution). Useful accession agents should wet the leaf. Preferred accession agents may exhibit rapid, almost instantaneous spreading when applied to the leaf surfaces to be treated. Stomatal infiltration of preferred accession agents involves mass flow in addition to any purely capillary flow or diffusion through stomatal apertures. The accession agents useful in the practice of this invention may be identified through any one of several tests for stomatal infiltration.

The following test is one of several that may be useful in determining whether a liquid is a potential stomatal infiltrant, and therefore can function as an accession agent in the method of the present invention. Plants of a suitable test species are grown, for example in a greenhouse or growth chamber, to such a size that they have fully expanded leaves. Velvetleaf (*Abutilon theophrasti*) has been found to be a convenient species for this test, but other species having stomata on the upper surface of the leaves may be found similarly useful. Growing conditions immediately prior to the test should be such as to favor the fully expanded leaves having their stomata open; normally this means that the plants should have been exposed for at least one hour to a light intensity of about 475 microeinsteins or more, and that the plants should not be subject to physiological stress from excess or deficiency of water, from excessively high or low temperature, or from other adverse environmental conditions.

The procedure described herein relates to velvetleaf. Modifications may be found necessary or desirable if another species is chosen. Potted velvetleaf plants are brought from the greenhouse and immediately sprayed with ROUNDUP® herbicide at a rate of 350 g a.e./ha in a spray volume of 93 l/ha, using a track sprayer. The spray solution is made by diluting 1 ml of ROUNDUP® herbicide to 95 ml with tap water. After spraying, the plants are returned to a well illuminated greenhouse, where they are allowed to sit for at least 10 minutes and preferably not more than one hour, during which time the spray deposit on the leaves substantially dries.

A liquid to be tested as a candidate stomatal infiltrant is prepared, for example by dilution of a surfactant in water at a desired concentration, and fluorescein is dissolved in the liquid at 0.1% by volume. An automatic syringe is used to dispense 0.8 microliters of the liquid containing fluorescein to each of three loci on the surface of one or more fully expanded leaves. The treated leaves remain attached to the plants throughout the procedure.

Exactly 10 minutes after dispensing the liquid, each treated leaf is washed with copious amounts of water to remove substantially all of the fluorescein from the leaf surface. The plants are then removed to a darkened place where the treated leaves are observed with the naked eye under long-wave ultraviolet illumination. If fluorescence is observed at or close to the loci of deposition of the candidate liquid, it can be concluded that the liquid has infiltrated stomata. Any such liquid has the potential to be an accession agent in the method of the present invention. If desired, the degree of fluorescence can be quantified by appropriate instrumentation, but this is unnecessary if the objective is simply to know whether or not a liquid is a stomatal infiltrant.

To verify that plants are in suitable condition for the test, a known accession agent can be tested by the above procedure. An aqueous solution of Silwet L-77 at 0.05% by volume typically gives a weak fluorescence signal indicating that modest infiltration has occurred. An aqueous solution of Silwet L-77 at 0.5% by volume typically gives a very strong fluorescence signal, indicating that a substantial amount of the solution has infiltrated stomata.

Preferred accession agents useful in the process of this invention are aqueous solutions of particular surfactants in a concentration sufficient to induce stomatal infiltration of the leaves or other foliage to be treated, as detected by any suitable test procedure, such as that described above. These surfactants are generally of a type known as "superwetting" or "superspreading" surfactants, and they are well known in the art. Two classes of superwetting surfactants have been found to be particularly useful as accession agents in the method of the present invention. Thus, the accession agent of the present invention is preferably an aqueous solution of a super-wetting surfactant selected from the group consisting of silicone—based surfactants (referred to herein as "organosilicone wetting agents" or simply "organosilicones") and fluorocarbon—based surfactants (referred to herein as "fluoro-organic wetting agents" or simply "fluoro-organics").

There are many classes of organosilicone wetting agents. One preferred class has the following general formula:

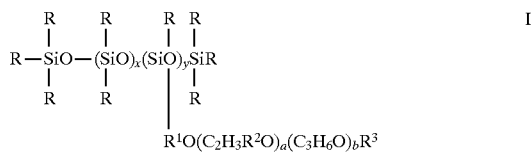

where each R is independently a monovalent saturated or unsaturated alkyl radical, $R^1$ is a divalent alkylidene radical, $R^2$ is independently hydrogen or a $C_1$–$C_4$ alkyl radical, $R^3$ is hydrogen or a monovalent saturated or unsaturated alkyl radical, x and b are integers independently greater than or equal to zero, and y and a are integers independently greater than or equal to one. In a preferred subclass of the compounds of Formula I, R and $R^3$ are —$CH_3$, $R^1$ is —$C_3H_6$—, $R^2$ is hydrogen, x is zero or one, y is one to five, a is five to 20, and b is zero. A second preferred subclass of the compounds of Formula I can be represented by the following formula:

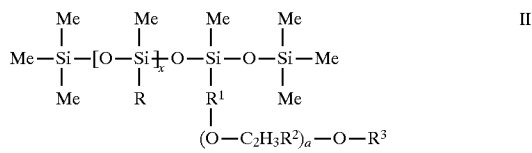

where a is one to 20, x is zero or one, R is $C_1$–$C_6$ alkyl, $R^1$ is divalent $C_1$–$C_6$ alkylidene, $R^2$ is independently H or —$CH_3$, and $R^3$ is H, $C_1$–$C_4$ alkyl, or $C_2$–$C_4$ acyl. A particularly preferred organosilicone wetting agent within the two preferred subclasses of Formula I is the compound having the following formula:

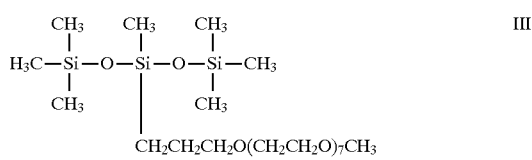

Another preferred class of organosilicone wetting agents has the general formula:

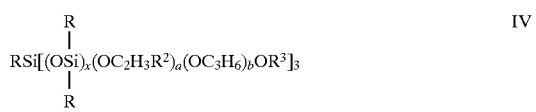

where R, $R^2$, $R^3$, x, a and b are as defined above for Formula I, except that x must be greater than one. Preferably in compounds of Formula IV, R and $R^3$ are —$CH_3$, $R^2$ is hydrogen, a is five to 20 and b is zero.

Organosilicones of the above formulas are generally described in product literature of Union Carbide Corp. and OSi Specialties, Inc., and in U.S. Pat. No. 3,505,377. Several of such ethoxylated organosilicone wetting agents are available from OSi Specialties as Silwet silicone glycol copolymers. Preferred Silwet surface active copolymers include Silwet L-77, Silwet 408, and Silwet 800. Silwet L-77 is an especially preferred ethoxylated organosilicone wetting agent which has an average formula corresponding to Formula III above.

An additional class of organosilicone wetting agents has the average formula

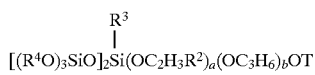   V where $R^2$, $R^3$, a, and b are as defined above for Formula IV, each $R^4$ group is independently a monovalent saturated or unsaturated alkyl radical, and T is hydrogen, a monovalent saturated or unsaturated alkyl radical, or a group of the formula $—Si(R^3)[OSi(OR^4)_3]_2$. Representative ethoxylated organosilicone wetting agents of Formula V are described in product literature of Olin Corporation and in U.S. Pat. Nos. 4,160,776, 4,226,794, and 4,337,168.

An additional class of organosilicone wetting agents has the average formula

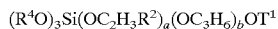   VI where $R^2$ and $R^4$ are as defined immediately above, e is at least four, f is greater than or equal to zero, and $T^1$ is hydrogen, a monovalent saturated or unsaturated alkyl radical, or a group of the formula $—Si(OR^4)_3$.

Fluoro-organic wetting agents useful in this invention are organic molecules represented by the formula

wherein $R_f$ is a fluoroaliphatic radical and G is a group which contains at least one hydrophilic group such as cationic, anionic, nonionic, or amphoteric groups. $R_f$ is a fluorinated, monovalent, aliphatic organic radical containing at least four carbon atoms. Preferably, it is a saturated perfluoroaliphatic monovalent organic radical. However, hydrogen or chlorine atoms can be present as substituents on the skeletal chain. While radicals containing a large number of carbon atoms may function adequately, compounds containing not more than about 20 carbon atoms are preferred since large radicals usually represent a less efficient utilization of fluorine than is possible with shorter skeletal chains. Preferably, $R_f$ contains about 5 to 14 carbon atoms.

The cationic groups which are usable in the fluoro-organic wetting agents employed in this invention may include an amine or a quaternary ammonium cationic group which can be oxygen-free (e.g., $—NH_2$) or oxygen-containing (e.g., amine oxides). Such amine and quaternary ammonium cationic hydrophilic groups can have formulas such as $—NH_2$, $—(NH_3)X$, $—(NH(R^2)_2)X$, $—(NH(R^2)_3)X$, or $—N(R_2)_2{\rightarrow}O$, where X is an anionic counterion such as halide, hydroxide, sulfate, bisulfate, or carboxylate, $R^2$ is H or $C_{1-18}$ alkyl group, and each $R^2$ can be the same as or different from other $R^2$ groups. Preferably, $R^2$ is H or a $C_{1-16}$ alkyl group and X is halide, hydroxide, or bisulfate. Preferably, the fluoro-organic wetting agents used in this invention contain hydrophilic groups which are quaternary ammonium cations.

The anionic groups which are usable in the fluoro-organic wetting agents employed in this invention include groups which by ionization can become radicals of anions. The anionic groups may have formulas such as $—COOM$, $—SO_3M$, $—OSO_3M$, $—PO_3M_2$, $—PO_3HM$, $—OPO_3M_2$, or $—OPO_3HM$, where M is H, a metal ion, $(NR^1_4)^+$, or $(SR^1_4)^+$, where each $R^1$ is independently H or substituted or unsubstituted $C_1$–$C_6$ alkyl. Preferably M is $Na^+$ or $K^+$. The preferred anionic groups of the fluoro-organic wetting agents used in this invention have the formula $—COOM$ or $—SO_3M$.

The amphoteric groups which are usable in the fluoro-organic wetting agent employed in this invention include groups which contain at least one cationic group as defined above and at least one anionic group as defined above.

The nonionic groups which are usable in the fluoro-organic wetting agents employed in this invention include groups which are hydrophilic but which under pH conditions of normal agronomic use are not ionized. The nonionic groups may have formulas such as $—O(CH_2CH_2)_xH$ where x is greater than zero, $—SO_2NH_2$, $—SO_2NHCH_2CH_2OH$, $—SO_2N(CH_2CH_2OH)_2$, $—CONH_2$, $—CONHCH_2CH_2OH$, or $—CON(CH_2CH_2OH)_2$.

Such cationic fluoro-organic wetting agents include those cationic fluorochemicals described, for example in U.S. Pat. Nos. 2,764,602, 2,764,603, 3,147,064, and 4,069,158. Such amphoteric fluoro-organic wetting agents include those amphoteric fluorochemicals described, for example, in U.S. Pat. Nos. 2,764,602, 4,042,522, 4,069,158, 4,069,244, 4,090,967, 4,161,590, and 4,161,602. Such anionic fluoro-organic wetting agents include those anionic fluorochemicals described, for example, in U.S. Pat. Nos. 2,803,656, 3,255,131, 3,450,755, and 4,090,967.

Especially preferred surfactants for use as components of accession agents include those organosilicone surfactants that are capable of reducing the surface tension of water to very low levels (typically below about 25 dyne/cm.). Other especially preferred surfactants for use as components of accession agents are fluoroalkyl surfactants, which may be anionic, nonionic, cationic or amphoteric. Both classes of materials have been demonstrated to produce enhanced herbicidal effects (with reduced species-specific antagonism) when applied sequentially to plant foliage following an initial application of a glyphosate composition. Thus, in accordance with the various aspects of the present invention, the herbicidal effectiveness of N-phosphonomethylglycine and its herbicidal derivatives is enhanced by sequentially applying a liquid accession agent capable of infiltrating the stomata of the treated species.

Any number of liquid accession agents may be employed in the method of this invention, and may be identified as useful through the procedures described above. Surfactant solutions that provide the appropriate indicia of stomatal infiltration at the concentrations tested will likely prove useful in the method of this invention. A concentration of surfactant shown to be useful by these tests is termed herein an "effective concentration" of, for example, an aqueous solution used as an accession agent.

The accession agents employed in this invention are liquids which provide rapid and enhanced access of the herbicide to the plant system wherein the herbicide is effective. While not being held to any theory of operation of the accession agents employed in the method of this invention, we have found that infiltration, which likely proceeds through foliar stomata, allows flow of liquid from the foliar surface into sub-stomatal and other voids in the interior of the foliage (such as intercellular voids). By infiltrating stomata, it appears that the accession agents employed in this invention carry with them any previously applied herbicide. The manner by which they do this is not yet understood, but the results are certainly at variance with the herbicidal effect observed when such agents are mixed (either in tank mix or in coformulation) with the herbicide prior to application to the plants. As demonstrated below, these accession agents may be antagonistic to the herbicidal effectiveness of the herbicide (on certain species and under certain application conditions) when employed in a tank mix. In such cases, superior herbicidal effect may be obtained using the sequential method of this invention, with the result being that plants can be controlled with lower rates of the applied herbicide.

Because leaf morphologies and consequent leaf/liquid interactions vary, different liquids show varying degrees of success on individual plant species when used in the method of this invention. However, sequential application of all operative accession agents useful in this invention will reduce to some degree the antagonism observed in the corresponding tank mix methods for a variety of plant species.

Application of Accession Agents

For accession agents which are surfactant solutions, the concentration of surfactant therein is important to achieving enhanced herbicidal effectiveness of pre-applied glyphosate compositions. Regarding such solutions, the solution itself is referred to herein as the "accession agent." The "concentration" of the "accession agent" refers to the concentration of the component ingredients (normally surfactants) of the "accession agent" in the aqueous solution as applied.

Even if a specific material at a specific concentration is observed (by one of the procedures outlined above) to infiltrate leaf stomata and penetrate the subsurface foliar voids, this concentration may nonetheless prove insufficient to enhance the herbicidal effect of glyphosate. In such cases, it may prove desirable to employ as an accession agent a solution containing a higher concentration of surfactant. Typically, the minimum concentration of the accession agent needed to obtain a desired enhancement of herbicidal effectiveness with minimal antagonism is 0.25% by volume, as exemplified by polyoxyethylene trisiloxane surfactants such as Silwet L-77. Other accession agents will have higher or lower minimum effective concentrations. It is highly preferred to use polyoxyethylene trisiloxane accession agents in concentrations of about 0.35 to 0.6% by volume. Higher concentrations may certainly be employed, but the cost of employing such higher concentrations would have to be balanced against the extent of improved results obtainable. However, significant enhancement of glyphosate effectiveness has been obtained by applying the accession agent at a concentration of at least about 0.5% by volume or greater. It has been found that for certain surfactants, much higher concentrations (i.e., greater than 1% and up to 5% by volume) must be used to obtain the enhanced herbicidal effect that is a feature of this invention. Certain accession agents may be neat liquids, in which case this invention may be practiced without a solvent or diluent. When a solvent or diluent is used as the major component of an accession agent, its specifics are not important to this invention, provided such solvent or diluent is capable of carrying the previously applied glyphosate along with it into the plant structure. Thus, when the herbicide is a water-soluble glyphosate salt, water suffices as a solvent in the accession agent.

Application rates for accession agents vary depending upon a number of factors, including the type and concentration of accession agent and the plant species involved. Application rates for accession agents generally should not be so high as to wash significant amounts of the herbicide off the foliage. Useful rates for applying an aqueous solution liquid accession agent to a field of foliage are from about 25 to about 1,000 liters per hectare (l/ha) by spray application. The preferred application rates for aqueous solutions are in the range from about 50 to about 300 l/ha.

Herbicides such as glyphosate must be taken up by living tissues of the plant and translocated within the plant in order to produce the desired herbicidal effect. Thus, it is important that the accession agent not be applied in such a manner as to excessively injure and interrupt the normal functioning of the plant. However, some limited degree of local injury may be insignificant, or even beneficial, in its impact on glyphosate effectiveness. We have observed that application at night or in cold weather may prove relatively ineffective. It is possible that is because leaf stomata may contract and restrict infiltration under these conditions, but these observations might be explainable on the basis of some other theory as well.

The liquid accession agent may be applied almost immediately, for example within seconds, after the herbicide has contacted the plant foliage. It may be applied with productive effect up to 96 hours or more later, provided there has been no intervening rainfall of a sufficient volume or intensity to remove a significant amount of the applied herbicide from the leaf surface. Typically, when the concentration of the surfactant in the accession agent is relatively low (i.e., about 0.25% by volume in the case of a polyoxyethylene trisiloxane), a preferred time period for application of the accession agent is from about one hour to about 24 hours, most preferably from about one hour to about three hours, after herbicide application. However, significant enhancement has been observed when the liquid accession agent is applied within about three minutes, and in field trials within a few seconds, after application of the herbicide. The accession agent may be deployed in a single, sequential application following a spray of a glyphosate composition. The accession agent may also be employed in multiple sequential applications after application of the glyphosate composition.

The method of this invention may also be practiced using a system whereby separate spray solutions are applied sequentially to plants from a single moving vehicle. This may be accomplished in a number of different ways, e.g., by using a double boom system or its equivalent. In this particular use of the present invention, a single vehicle may carry two booms, one spraying a liquid glyphosate composition and the other spraying, a liquid accession agent. Each of the booms employed in this exemplary use of the present invention can employ any conventional means for spraying liquids, such as spray nozzles, atomizers, or the like. Instead of two booms, each with plurality of spray nozzles, the method of the present invention may also be carried out with a single boom having, two sets of nozzles or the like, one set spraying, a liquid glyphosate composition and the other set spraying, a liquid accession agent. The two sets of nozzles should be oriented differently on the single boom so that, as the vehicle carrying the boom moves forward, the glyphosate composition contacts the plants being, treated prior to the time when the accession agent contacts the same plants. In any of these approaches, the period of time between the application of the glyphosate composition and the application of the accession agent will depend upon the distance between the two spray booms (or the distance between spray paths created by the two differently oriented sets of spray nozzles where a single boom is employed) and the speed of the vehicle carrying the boom or booms. A preferred period of time between the two applications is from about 0.05 to about ten seconds. The great convenience and cost savings of such a single moving vehicle system may in many cases compensate for the somewhat weaker overall enhancement by comparison with a more delayed sequential application.

Glyphosate is known generally to be effective at lower rates as a herbicide for grasses then for broadleaf plants, although it is widely used on all species. We have found, however, that for both classes of plant species for which glyphosate and an accession agent are antagonistic in a coformulation or tank mix, superior results are achieved through the sequential application method of this invention.

Tank Mixes v. Sequential Application

The sequential application method of the present invention provides a novel method for avoidingy the antagonism that might be found in certain plant species when the accession agent and herbicide (e.g., glyphosate) are employed in a tank mix. This reduction (and in many instances elimination) of antagonism offers a number of practical and commercial advantages over the prior tank mix methods.

First, this invention facilitates use of accession agents in fields infested with a variety of plant species. When used in a tank mix, the accession agent may enhance glyphosate activity with respect to some species, but reduce glyphosate activity with respect to others (antagonism). A single application of the tank mix will, in such cases, prove ineffective to control all plant species, unless the glyphosate is introduced at significantly higher levels, thereby defeating the purpose of the accession agent. In contrast, as demonstrated below, the sequential application method of this invention will preserve or in some cases further magnify the enhancements of herbicidal effectiveness provided by the tank mix, but substantially reduce or eliminate antagonism for individual plant species that might be found in the subject field. This invention therefore permits use of accession agents over a broad spectrum of plant species, unlike tank mix methods which may enhance or decrease herbicidal activity depending on the plant species.

In addition to permitting, the effective use of accession agents over a spectrum of plant species and thus making such agents useful in cases of infestation by multiple species, the present invention reduces the work required to screen accession agents for species-specific antagonism. In those instances where tank mixes of glyphosate and accession agent are antagonistic, use of the sequential method of this invention will substantially reduce (if not eliminate) such antagonism. In those instances where the accession agent improves the herbicidal effectiveness of glyphosate in a tank mix, the sequential application method of this invention will yield at least comparable results. Thus, as a result of the sequential method of this invention, increased use of accession agents will be made possible, because when used in the method of the present invention, they provide enhanced glyphosate activity in some plant species without antagonistic effect in others.

EXAMPLES

The following examples are provided for illustrative purposes only and are not intended to limit the scope of the present invention defined by the claims. In these examples, percentage amounts refer to percent by volume unless otherwise noted.

In the following examples, experiments were performed using the following (and other) formulations:

Formulation A: which consists of 41% by weight of the monoisopropylamine salt of glyphosate in aqueous solution with a coformulant (7.5% by weight) of a surfactant (MON-0818 of Monsanto Company) based upon 15 EO tallowamine polyethoxylate.

Formulation B: which consists of 41% by weight of the monoisopropylamine salt of glyphosate in aqueous solution.

Formulation C: which consists of 41% by weight of the monoisopropylamine salt of glyphosate in aqueous solution with a coformulant (15% by weight) of MON-0818 surfactant.

Formulation J: which consists of 41% by weight of the monoisopropylamine salt of glyphosate in aqueous solution, together with inert ingredients that have not publicly been disclosed. This formulation is sold in the USA by the Monsanto Company under the ROUNDUP® Ultra trademark.

All of these formulations contain 356 grams of glyphosate acid equivalent per liter (g a.e./l). Other formulations used are described in the particular Examples where they occur.

Example 1

Seeds of velvetleaf (*Abutilon theophrasti*, ABUTH) were planted in 85 mm square pots in a soil mix which was previously steam sterilized and pre-fertilized with a 14-14-14 NPK slow release fertilizer at a rate of 3.6 $kg/m^3$. The pots were placed in a greenhouse with sub-irrigation. About one week after emergence, seedlings were thinned as needed, including removal of any unhealthy or abnormal plants, to create a uniform series of test pots.

The plants were maintained for the duration of the test in the greenhouse where they received a minimum of 14 hours of light per day. If natural light was insufficient to achieve the daily requirement, artificial light with an intensity of approximately 475 microeinsteins was used to make up the difference. Exposure temperatures were not precisely controlled but averaged about 27° C. during the day and 18° C. during the night. Plants were sub-irrigated throughout the test to ensure adequate soil moisture levels.

Pots were assigned to different treatments in a fully randomized experimental design with 3 replications. A set of pots was left untreated as a reference against which effects of the treatments could later be evaluated.

Initial treatments with Formulation A, alone or in tank mix with an accession agent, were applied 20 days after planting. Initial treatments were applied by spraying with a track sprayer fitted with a 9501E nozzle calibrated to deliver a spray volume of 93 liters per hectare (l/ha) at a pressure of 166 kilopascals (kPa). Plants treated according to methods of prior art, for comparative purposes, received an initial treatment only. Plants treated by a method illustrative of the present invention received an initial application of Formulation A followed sequentially by a subsequent application of an accession agent. Various intervals between initial and subsequent applications were tested in this Example. Some treatments involved a single subsequent application of an accession agent; others involved multiple subsequent treatments. All subsequent applications in this Example were applied by spraying an accession agent with a track sprayer fitted exactly as for the initial application and calibrated to deliver a spray volume of 93 l/ha at a pressure of 166 kPa.

Formulation A was applied without accession agent at a range of rates from 300 to 1000 g a.e./ha. When an accession agent was included in the treatment, either in tank mix with Formulation A or as a subsequent application, only the two lowest rates of Formulation A, 300 and 400 g a.e./ha, were tested. This Example uses only one accession agent, an aqueous solution containing 5% glycerin and 0.25% Silwet L-77 (abbreviated in data tables herein as L-77). Silwet L-77 is a commercial polyethoxylated trisiloxane surfactant having the chemical structure shown above and is a product of Witco Corporation, OSi Specialties Group. As this surfactant is known to be hydrolytically unstable in aqueous solution, spray solutions were prepared immediately before application. The time interval between initial and subsequent applications was varied from about 0.05 hour (the shortest interval that could practically be tested using the procedure of this Example) to 24 hours.

Except for pots subjected to the ~0.05 hour interval between initial and subsequent applications, pots were returned to the greenhouse between applications. After the subsequent application, all pots remained in the greenhouse until ready for evaluation.

Twenty-three days after the initial application, all plants in the test were examined by a single practiced technician to evaluate percent inhibition, which is a visual measurement of the effectiveness of the treatment by comparison with untreated plants. A percent inhibition of 0% indicates no effect, and a percent inhibition of 100% indicates that all of the specimens are completely dead. A percent inhibition of 85% or more is in most cases considered acceptable for normal herbicidal uses.

Treatments and corresponding percent inhibitions are given in Table 1.

TABLE 1

| Initial application 93 l/ha | | Glyphosate rate | Subsequent application 93 l/ha | % Inhibition |
|---|---|---|---|---|
| herbicide | accession agent | g a.e./ha | accession agent | ABUTH |
| Formulation A | none | 300 | none | 43 |
| Formulation A | none | 400 | none | 63 |
| Formulation A | none | 500 | none | 82 |
| Formulation A | none | 600 | none | 75 |
| Formulation A | none | 800 | none | 98 |
| Formulation A | none | 1000 | none | 99 |
| Formulation A | 5% glycerin + 0.25% L-77 | 300 | none | 14 |
| Formulation A | 5% glycerin + 0.25% L-77 | 400 | none | 10 |
| Formulation A | none | 300 | 5% glycerin + 0.25% L-77 at ~0.05 hr | 31 |
| Formulation A | none | 400 | 5% glycerin + 0.25% L-77 at ~0.05 hr | 44 |
| Formulation A | none | 300 | 5% glycerin + 0.25% L-77 at 1 hr | 30 |
| Formulation A | none | 400 | 5% glycerin + 0.25% L-77 at 1 hr | 53 |
| Formulation A | none | 300 | 5% glycerin + 0.25% L-77 at 3 hrs | 56 |
| Formulation A | none | 400 | 5% glycerin + 0.25% L-77 at3hrs | 69 |
| Formulation A | none | 300 | 5% glycerin + 0.25% L-77 at 6 hrs | 60 |
| Formulation A | none | 400 | 5% glycerin + 0.25% L-77 at 6 hrs | 54 |
| Formulation A | none | 300 | 5% glycerin + 0.25% L-77 at 24 hrs | 38 |
| Formulation A | none | 400 | 5% glycerin + 0.25% L-77 at 24 hrs | 61 |
| Formulation A | none | 300 | 5% glycerin + 0.25% L-77 at 1 and 3 hrs | 57 |
| Formulation A | none | 400 | 5% glycerin + 0.25% L-77 at 1 and 3 hrs | 71 |
| Formulation A | none | 300 | 5% glycerin + 0.25% L-77 at 1, 3 and 6 hrs | 56 |
| Formulation A | none | 400 | 5% glycerin + 0.25% L-77 at 1, 3 and 6 hrs | 82 |
| Formulation A | none | 300 | 5% glycerin + 0.25% L77 at 1, 3, 6 and 24 hrs | 69 |
| Formulation A | none | 400 | 5% glycerin + 0.25% L77 at 1, 3, 6 and 24 hrs | 74 |

The comparative tank mix treatments of this Example, employing an accession agent which is a combination of glycerin and Silwet L-77 in aqueous solution, are noticeably antagonistic to herbicidal effectiveness of glyphosate. This antagonism is reduced significantly ashen the same accession agent is applied sequentially following the glyphosate, instead of being included with the glyphosate in tank mix. Significant improvement in herbicidal effectiveness of glyphosate is found in treatments involving multiple sequential applications of the same accession agent. Glycerin has been used and proposed as a humectant material to improve tank mix performance of Silwet L-77.

Example 2

Velvetleaf (*Abutilon theophrasti*, ABUTH) plants were grown in pots, maintained in a greenhouse and treated with initial and subsequent applications by procedures exactly as described for Example 1, except where otherwise noted below.

Initial applications of Formulation A, alone or in tank mix with an accession agent, were applied in a spray volume of 93 l/ha at a pressure of 166 kPa, 22 days after planting. All subsequent applications in this Example were applied by spraying an accession agent at a spray volume of 280 l/ha at a pressure of 166 kPa.

Formulation A was applied without accession agent at a range of rates from 200 to 800 g a.e./ha. When an accession agent was included in the treatment, either in tank mix with Formulation A or as a subsequent application, only the three lowest rates of Formulation A, 200, 300 and 400 g a.e./ha, were tested. This Example includes only one accession agent, an aqueous solution containing 0.5% Silwet L-77. The time interval between initial and subsequent applications was about 0.05 hour or 4 hours.

Twenty-one days after the initial application, all plants in the test were examined by a single practiced technician to evaluate percent inhibition. Treatments and corresponding percent inhibitions are given in Table 2.

Here, Silwet L-77 in tank mix formulation gave some enhancement of herbicidal effectiveness. Somewhat greater enhancement was obtained through sequential application of Silwet L-77.

Example 3

Prickly sida (*Sida spinosa*, SIDSP) plants were grown in pots, maintained in a greenhouse and treated with initial and subsequent applications by procedures exactly as described for Example 1, except where otherwise noted below.

Initial applications of Formulation A, alone or in tank mix with an accession agent, were applied 29 days after planting. Formulation A was applied without accession agent at a range of rates from 300 to 1000 g a.e./ha. When an accession agent was included in the treatment, either in tank mix with Formulation A or as a subsequent application, only the three lowest rates of Formulation A, 300, 400 and 500 g a.e./ha, were tested. This Example includes as accession agent an aqueous solution containing 0.5% or 0.25% Silwet L-77. The time interval between initial and subsequent applications was varied from about 0.05 hour to 3 hours.

Twenty-three days after the initial application, all plants in the test were examined by a single practiced technician to evaluate percent inhibition. Treatments and corresponding percent inhibitions are given in Table 3.

TABLE 2

| Initial application 93 l/ha | | Glyphosate rate | Subsequent application 93 l/ha | % Inhibition |
|---|---|---|---|---|
| herbicide | accession agent | g a.e./ha | accession agent | ABUTH |
| Formulation A | none | 200 | none | 0 |
| Formulation A | none | 300 | none | 13 |
| Formulation A | none | 400 | none | 40 |
| Formulation A | none | 500 | none | 50 |
| Formulation A | none | 600 | none | 55 |
| Formulation A | none | 800 | none | 75 |
| Formulation A | 0.5% L-77 | 200 | none | 49 |
| Formulation A | 0.5% L-77 | 300 | none | 48 |
| Formulation A | 0.5% L-77 | 400 | none | 61 |
| Formulation A | none | 200 | 0.5% L-77 at ~0.05 hr | 60 |
| Formulation A | none | 300 | 0.5% L-77 at ~0.05 hr | 73 |
| Formulation A | none | 400 | 0.5% L-77 at ~0.05 hr | 77 |
| Formulation A | none | 200 | 0.5% L-77 at 4 hrs | 66 |
| Formulation A | none | 300 | 0.5% L-77 at 4 hrs | 77 |
| Formulation A | none | 400 | 0.5% L-77 at 4 hrs | 78 |

TABLE 3

| Initial application 93 l/ha | | Glyphosate rate | Subsequent application 93 l/ha | % Inhibition |
|---|---|---|---|---|
| herbicide | accession agent | g a.e./ha | accession agent | SIDSP |
| Formulation A | none | 300 | none | 58 |
| Formulation A | none | 400 | none | 84 |
| Formulation A | none | 500 | none | 93 |
| Formulation A | none | 600 | none | 96 |
| Formulation A | none | 800 | none | 99 |
| Formulation A | none | 1000 | none | 100 |
| Formulation A | 0.5% L-77 | 300 | none | 44 |
| Formulation A | 0.5% L-77 | 400 | none | 74 |
| Formulation A | 0.5% L-77 | 500 | none | 84 |
| Fonnulation A | none | 300 | 0.5% L-77 at ~0.05 hr | 67 |
| Formulation A | none | 400 | 0.5% L-77 at ~0.05 hr | 66 |
| Formulation A | none | 500 | 0.5% L-77 at ~0.05 hr | 80 |
| Formulation A | none | 300 | 0.5% L-77 at 1 hr | 89 |
| Formulation A | none | 400 | 0.5% L-77 at 1 hr | 94 |
| Formulation A | none | 500 | 0.5% L-77 at 1 hr | 94 |
| Formulation A | none | 300 | 0.5% L-77 at 3 hrs | 76 |
| Formulation A | none | 400 | 0.5% L-77 at 3 hrs | 89 |
| Formulation A | none | 500 | 0.5% L-77 at 3 hrs | 90 |
| Formulation A | none | 300 | 0.25% L-77 at 1 hr | 74 |
| Formulation A | none | 400 | 0.25% L-77 at 1 hr | 77 |
| Formulation A | none | 500 | 0.25% L-77 at 1 hr | 82 |

Silwet L-77 in tank mix formulation was mildly antagonistic to the effectiveness of the herbicidal composition in prickly sida. This antagonism was overcome through sequential application after one and three hours, which gave significant improvement of effectiveness over the herbicidal composition applied without Silwet L-77, and applied with Silwet L-77 in tank mix.

Example 4

Morningglory (*Ipomoea sp.*, IPOSS) plants were grown in pots, maintained in a greenhouse and treated with initial and subsequent applications by procedures exactly as described for Example 1, except where otherwise noted below.

Initial applications of Formulations A, B and C, alone or in tank mix with an accession agent, were applied 29 days after planting. Formulations were each applied without accession agent at a range of rates from 400 to 800 g a.e./ha. When an accession agent was included in the treatment, either in tank mix or as a subsequent application, only the two lowest rates of each glyphosate formulation, 400 and 600 g a.e./ha, were tested. This Example includes as accession agent an aqueous solution containing 0.5% Silwet L-77.

All subsequent applications in this Example were made by spraying the accession agent with a track sprayer fitted as in Example 1 but calibrated to deliver a spray volume of 280 l/ha at a pressure of 166 kPa. The time interval between initial and subsequent applications was 1 hour.

Twenty-two days after the initial application, all plants in the test were examined by a single practiced technician to evaluate percent inhibition. Treatments and corresponding percent inhibitions are given in Table 4.

TABLE 4

| Initial application 93 l/ha | | Glyphosate rate | Subsequent application 93 l/ha | % Inhibition |
|---|---|---|---|---|
| herbicide | accession agent | g a.e./ha | accession agent | IPOSS |
| Formulation A | none | 400 | none | 347 |
| Formulation A | none | 600 | none | 85 |
| Formulation A | none | 800 | none | 85 |
| Formulation A | 0.5% L-77 | 400 | none | 63 |
| Formulation A | 0.5% L-77 | 600 | none | 70 |
| Formulation A | none | 400 | 0.5% L-77 at 1 hr | 91 |
| Formulation A | none | 600 | 0.5% L-77 at 1 hr | 95 |
| Formulation B | none | 400 | none | 13 |
| Formulation B | none | 600 | none | 69 |
| Formulation B | none | 800 | none | 70 |
| Formulation B | 0.5% L-77 | 400 | none | 72 |
| Formulation B | 0.5% L-77 | 600 | none | 87 |
| Formulation B | none | 400 | 0.5% L-77 at 1 hr | 91 |
| Formulation B | none | 600 | 0.5% L-77 at 1 hr | 94 |
| Formulation C | none | 400 | none | 62 |
| Formulation C | none | 600 | none | 87 |
| Formulation C | none | 800 | none | 96 |
| Formulation C | 0.5% L-77 | 400 | none | 81 |

TABLE 4-continued

| Initial application 93 l/ha | | Glyphosate rate | Subsequent application 93 l/ha | % Inhibition |
|---|---|---|---|---|
| herbicide | accession agent | g a.e./ha | accession agent | IPOSS |
| Formulation C | 0.5% L-77 | 600 | none | 83 |
| Formulation C | none | 400 | 0.5% L-77 at 1 hr | 89 |
| Formulation C | none | 600 | 0.5% L-77 at 1 hr | 100 |

Remarkable improvement (over the comparative tank mix treatment) in herbicidal effectiveness is achieved in this Example by applying the accession agent subsequent to the initial herbicide application for each of Formulation A, Formulation B and Formulation C

Example 5

Russian thistle (*Salsola iberica*, SASKR) plants were grown in pots, maintained in a greenhouse and treated with initial and subsequent applications by procedures exactly as described for Example 1, except where otherwise noted below. Greenhouse temperature was maintained at approximately 21° C. during the day and 16° C. during the night.

The experimental design included only two replicate pots per treatment. Initial applications of Formulation A, alone or in tank mix with an accession agent, were applied 27 days after planting. Formulation A was applied without accession agent at a range of rates from 200 to 800 g a.e./ha. When an accession agent was included in the treatment, either in tank mix or as a subsequent application, the rates of Formulation A tested were 200, 300 and 400 g a.e./ha. This Example includes as accession agent an aqueous solution containing 0.5% Silwet L-77. The time interval between initial and subsequent applications was varied from about 0.05 hour to 3 hours.

Twenty days after the initial application, all plants in the test were examined by a single practiced technician to evaluate percent inhibition. Treatments and corresponding percent inhibitions are given in Table 5.

Silwet L-77 enhanced the effectiveness of the herbicidal composition for russian thistle when added in tank mix. The enhancement is comparable to that achieved when Silwet L-77 is applied sequentially.

Example 6

Wild buckwheat (*Polygonum convolvulus*, POLCO) plants were grown in pots, maintained in a greenhouse and treated with initial and subsequent applications by procedures exactly as described for Example 1, except where otherwise noted below.

Initial applications of Formulation A, alone or in tank mix with an accession agent, were applied 24 days after planting. Formulation A was applied without accession agent at a range of rates from 250 to 600 g a.e./ha. When an accession agent was included in the treatment, either in tank mix or as a subsequent application, Formulation A was tested only at the lowest rate. This Example includes as accession agents aqueous solutions containing Silwet L-77 at a range of concentrations from 0.25% to 1.5%. The time interval between initial and subsequent applications was varied from about 0.05 hour to 24 hours.

Fourteen days after the initial application, all plants in the test were examined by a single practiced technician to evaluate percent inhibition. Treatments and corresponding percent inhibitions are given in Table 6.

TABLE 5

| Initial application 93 l/ha | | Glyphosate rate | Subsequent application 93 l/ha | % Inhibition |
|---|---|---|---|---|
| herbicide | accession agent | g a.e./ha | accession agent | SASKR |
| Formulation A | none | 200 | none | 15 |
| Formulation A | none | 300 | none | 69 |
| Formulation A | none | 400 | none | 86 |
| Formulation A | none | 500 | none | 93 |
| Formulation A | none | 600 | none | 100 |
| Formulation A | none | 800 | none | 100 |
| Formulation A | 0.5% L-77 | 200 | none | 50 |
| Formulation A | 0.5% L-77 | 300 | none | 37 |
| Formulation A | 0.5% L-77 | 400 | none | 78 |
| Formulation A | none | 200 | 0.5% L-77 at ~0.05 hr | 20 |
| Formulation A | none | 300 | 0.5% L-77 at ~0.05 hr | 55 |
| Formulation A | none | 400 | 0.5% L-77 at ~0.05 hr | 87 |
| Formulation A | none | 200 | 0.5% L-77 at 1 hr | 43 |
| Formulation A | none | 300 | 0.5% L-77 at 1 hr | 66 |
| Formulation A | none | 400 | 0.5% L-77 at 1 hr | 81 |
| Formulation A | none | 200 | 0.5% L-77 at 3 hrs | 31 |
| Formulation A | none | 300 | 0.5% L-77 at 3 hrs | 63 |
| Formulation A | none | 400 | 0.5% L-77 at 3 hrs | 74 |

TABLE 6

| Initial application 93 l/ha | | Glyphosate rate | Subsequent application 93 l/ha | % Inhibition |
|---|---|---|---|---|
| herbicide | accession agent | g a.e./ha | accession agent | POLCO |
| Formulation A | none | 250 | none | 63 |
| Formulation A | none | 450 | none | 87 |
| Formulation A | none | 600 | none | 97 |
| Formulation A | 0.25% L-77 | 250 | none | 37 |
| Formulation A | 0.5% L-77 | 250 | none | 53 |
| Formulation A | 1.0% L-77 | 250 | none | 83 |
| Formulation A | 1.5% L-77 | 250 | none | 97 |
| Formulation A | none | 250 | 0.25% L-77 at ~0.05 hr | 35 |
| Formulation A | none | 250 | 0.5% L-77 at ~0.05 hr | 73 |
| Formulation A | none | 250 | 1.0% L-77 at ~0.05 hr | 86 |
| Formulation A | none | 250 | 1.5% L-77 at ~0.05 hr | 95 |
| Formulation A | none | 250 | 0.25% L-77 at 4 hrs | 33 |
| Formulation A | none | 250 | 0.5% L-77 at 4 hrs | 65 |
| Formulation A | none | 250 | 1.0% L-77 at 4 hrs | 71 |
| Formulation A | none | 250 | 1.5% L-77 at 4 hrs | 81 |
| Formulation A | none | 250 | 0.25% L-77 at 8 hrs | 48 |
| Formulation A | none | 250 | 0.5% L-77 at 8 hrs | 62 |
| Formulation A | none | 250 | 1.0% L-77 at 8 hrs | 53 |
| Formulation A | none | 250 | 1.5%.L-77 at 8 hrs | 49 |
| Formulation A | none | 250 | 0.25% L-77 at 24 hrs | 38 |
| Formulation A | none | 250 | 0.5% L-77 at 24 hrs | 58 |
| Formulation A | none | 250 | 1.0% L-77 at 24 hrs | 48 |
| Formulation A | none | 250 | 1.5% L-77at 24 hrs | 38 |

Silwet L-77 in tank mix enhances the effectiveness of the herbicidal composition on wild buckwheat at higher concentrations of the accession agent, but is antagonistic for lower concentrations. The effect of sequential application is comparable, except for a loss of enhancement at higher Silwet L-77 concentrations (~1%) applied at later times (8 hours or more later).

Example 7

Yellow nutsedge (*Cyperus esculentus*, CYPES) plants were grown in pots, maintained in a greenhouse and treated with initial and subsequent applications by procedures exactly as described for Example 1, except where otherwise noted below.

Initial applications of Formulation A, alone or in tank mix with an accession agent, were applied 22 days after planting. Formulation A was applied without accession agent at a range of rates from 1200 to 2000 g a.e./ha. When an accession agent was included in the treatment, either in tank mix or as a subsequent application, Formulation A was tested only at the lowest rate. This Example includes as accession agents aqueous solutions containing Silwet L-77 at a range of concentrations from 0.125% to 1.5%. The time interval between initial and subsequent applications was varied from about 0.05 hour to 24 hours.

Nineteen days after the initial application, all plants in the test were examined by a single practiced technician to evaluate percent inhibition. Treatments and corresponding percent inhibitions are given in Table 7.

TABLE 7

| Initial application 93 l/ha | | Glyphosate rate | Subsequent application 93 l/ha | % Inhibition |
|---|---|---|---|---|
| herbicide | accession agent | g a.e./ha | accession agent | CYPES |
| Formulation A | none | 1200 | none | 41 |
| Formulation A | none | 1600 | none | 96 |
| Formulation A | none | 2000 | none | 97 |
| FormulationA | 0.125%.L-77 | 1200 | none | 70 |
| Formulation A | 0.25% L-77 | 1200 | none | 81 |
| Formulation A | 0.5% L-77 | 1200 | none | 92 |
| Formulation A | 1.0% L-77 | 1200 | none | 81 |
| Formulation A | 1.5% L-77 | 1200 | none | 74 |
| Formulation A | none | 1200 | 0.125% L-77 at ∞0.05 hr | 73 |
| Formulation A | none | 1200 | 0.25% L-77 at ~0.05 hr | 87 |
| Formulation A | none | 1200 | 0.5% L-77 at ~0.05 hr | 86 |
| Formulation A | none | 1200 | 1.0% L-77 at ~0.05 hr | 89 |
| Formulation A | none | 1200 | 1.5% L-77 at ~0.05 hr | 86 |
| Formulation A | none | 1200 | 0.125%L-77 at 4hrs | 59 |
| Formulation A | none | 1200 | 0.25% L-77 at 4 hrs | 79 |
| Formulation A | none | 1200 | 0.5% L-77 at 4 hrs | 89 |
| Formulation A | none | 1200 | 1.0% L-77 at 4 hrs | 88 |
| Formulation A | none | 1200 | 1.5% L-77 at 4 hrs | 69 |

TABLE 7-continued

| Initial application 93 l/ha | | Glyphosate rate | Subsequent application 93 l/ha | % Inhibition |
|---|---|---|---|---|
| herbicide | accession agent | g a.e./ha | accession agent | CYPES |
| Formulation A | none | 1200 | 0.125% L-77 at 8 hrs | 70 |
| Formulation A | none | 1200 | 0.25% L-77 at 8 hrs | 67 |
| Formulation A | none | 1200 | 0.5% L-77 at 8 hrs | 95 |
| Formulation A | none | 1200 | 1.0% L-77 at 8 hrs | 83 |
| Formulation A | none | 1200 | 1.5% L-77 at 8 hrs | 83 |
| Formulation A | none | 1200 | 0.125% L-77 at 24 hrs | 86 |
| Formulation A | none | 1200 | 0.25% L-77 at 24 hrs | 94 |
| Formulation A | none | 1200 | 0.5% L-77 at 24 hrs | 59 |
| Formulation A | none | 1200 | 1.0% L-77 at 24 hrs | 81 |
| Formulation A | none | 1200 | 1.5% L-77 at 24 hrs | 68 |

Silwet L-77 in tank mix significantly enhances the effectiveness of the herbicidal composition on yellow nutsedge at all the tested accession agent concentrations. The effect of sequential application of the accession agent is generally comparable.

Example 8

Winter wheat (*Triticum aestivum*, TRZAW) plants were grown in pots, maintained in a greenhouse and treated with initial and subsequent applications by procedures exactly as described for Example 1, except where otherwise noted below.

Initial applications of Formulations B and C, alone or in tank mix with an accession agent, were applied 14 days after planting. Formulations were each applied without accession agent at a range of rates from 75 to 450 g a.e./ha. When an accession agent was included in the treatment, either in tank mix or as a subsequent application, formulations were tested across the same range of rates. This Example includes as accession agents aqueous solutions containing Silwet L-77 at a range of concentrations from 0.2% to 1.0%. The time interval between initial and subsequent applications was 4 or 8 hours.

Fourteen days after the initial application, all plants in the test were examined by a single practiced technician to evaluate percent inhibition. Treatments and corresponding percent inhibitions are given in Table 8.

TABLE 8

| Initial application 93 l/ha | | Glyphosate rate | Subsequent application 93 l/ha | % Inhibition |
|---|---|---|---|---|
| herbicide | accession agent | g a.e./ha | accession agent | TRZAW |
| Formulation B | none | 150 | none | 8 |
| Formulation B | none | 450 | none | 55 |
| Formulation B | 0.2% L-77 | 75 | none | 11 |
| Formulation B | 0.2% L-77 | 150 | none | 20 |
| Formulation B | 0.2% L-77 | 450 | none | 93 |
| Formulation B | none | 75 | 0.2% L-77 at 4 hrs | 13 |
| Formulation B | none | 150 | 0.2% L-77 at 4 hrs | 15 |
| Formulation B | none | 450 | 0.2% L-77 at 4 hrs | 45 |
| Formulation B | none | 75 | 0.2% L-77 at 8 hrs | 30 |
| Formulation B | none | 150 | 0.2% L-77 at 8 hrs | 18 |
| Formulation B | none | 450 | 0.2% L-77 at 8 hrs | 56 |
| Formulation B | 0.5% L-77 | 75 | none | 62 |
| Formulation B | 0.5% L-77 | 150 | none | 44 |
| Formulation B | 0.5% L-77 | 450 | none | 68 |
| Formulation B | none | 75 | 0.5% L-77 at 4 hrs | 37 |
| Formulation B | none | 150 | 0.5% L-77 at 4 hrs | 21 |
| Formulation B | none | 450 | 0.5% L-77 at 4 hrs | 67 |
| Formulation B | none | 75 | 0.5% L-77 at 8 hrs | 30 |
| Formulation B | none | 150 | 0.5% L-77 at 8 hrs | 33 |
| Formulation B | none | 450 | 0.5% L-77 at 8 hrs | 67 |
| Formulation B | 1.0% L-77 | 75 | none | 56 |
| Formulation B | 1.0% L-77 | 150 | none | 83 |
| Formulation B | 1.0% L-77 | 450 | none | 100 |
| Formulation B | none | 75 | 1.0% L-77 at 4 hrs | 15 |
| Formulation B | none | 150 | 1.0% L-77at4hrs | 38 |
| Formulation B | none | 450 | 1.0% L-77 at 4 hrs | 69 |
| Formulation B | none | 75 | 1.0% L-77 at 8 hrs | 34 |
| Formulation B | none | 150 | 1.0% L-77 at 8 hrs | 34 |
| Formulation B | none | 450 | 1.0% L-77 at 8 hrs | 59 |
| Formulation C | none | 75 | none | 76 |
| Formulation C | none | 150 | none | 93 |
| Formulation C | none | 450 | none | 100 |
| Formulation C | 0.2% L-77 | 75 | none | 44 |

TABLE 8-continued

| Initial application 93 l/ha | | Glyphosate rate | Subsequent application 93 l/ha | % Inhibition |
|---|---|---|---|---|
| herbicide | accession agent | g a.e./ha | accession agent | TRZAW |
| Formulation C | 0.2% L-77 | 150 | none | 53 |
| Formulation C | 0.2% L-77 | 450 | none | 98 |
| Formulation C | none | 75 | 0.2% L-77 at 4 hrs | 58 |
| Formulation C | none | 150 | 0.2% L-77 at 4 hrs | 78 |
| Formulation C | none | 450 | 0.2% L-77 at 4 hrs | 99 |
| Formulation C | none | 75 | 0.2% L-77 at 8 hrs | 58 |
| Formulation C | none | 150 | 0.2% L-77 at 8 hrs | 77 |
| Formulation C | none | 450 | 0.2% L-77 at 8 hrs | 97 |
| Formulation C | 0.5% L-77 | 75 | none | 27 |
| Formulation C | 0.5% L-77 | 150 | none | 48 |
| Formulation C | 0.5% L-77 | 450 | none | 98 |
| Formulation C | none | 75 | 0.5% L-77 at 4 hrs | 66 |
| Formulation C | none | 150 | 0.5% L-77 at 4 hrs | 94 |
| Formulation C | none | 450 | 0.5% L-77 at 4 hrs | 99 |
| Formulation C | none | 75 | 0.5% L-77 at 8 hrs | 66 |
| Formulation C | none | 150 | 0.5% L-77 at 8 hrs | 85 |
| Formulation C | none | 450 | 0.5% L-77 at 8 hrs | 99 |
| Formulation C | 1.0% L-77 | 75 | none | 49 |
| Formulation C | 1.0% L-77 | 150 | none | 64 |
| Formulation C | 1.0% L-77 | 450 | none | 99 |
| Formulation C | none | 75 | 1.0% L-77 at 4 hrs | 71 |
| Formulation C | none | 150 | 1.0% L-77at 4 hrs | 88 |
| Formulation C | none | 450 | 1.0% L-77 at 4 hrs | 97 |
| Formulation C | none | 75 | 1.0% L-77 at 8 hrs | 66 |
| Formulation C | none | 150 | 1.0% L-77 at 8 hrs | 81 |
| Formulation C | none | 450 | 1.0% L-77 at 8 hrs | 100 |

The greatest improvement of herbicidal effectiveness through sequential application of an accession agent in this Example is in the case of Formulation C, which includes a polyethoxylated tallowamine based surfactant, unlike Formulation B, which contains no surfactant.

Example 9

Soybean (*Glycine max*, GLXMA) plants were grown in pots, maintained in a greenhouse and treated with initial and subsequent applications by procedures exactly as described for Example 1, except where otherwise noted below.

Initial applications of Formulation A, alone or in tank mix with an accession agent, were applied 18 days after planting. Formulation A was applied without accession agent at a range of rates from 250 to 800 g a.e./ha. When an accession agent was included in the treatment, either in tank mix or as a subsequent application, Formulation A was tested only at the lowest rate. This Example includes as accession agents aqueous solutions containing Silwet L-77 at a range of concentrations from 0.125% to 1.0%. The time interval between initial and subsequent applications was varied from about 0.05 to 24 hours.

Sixteen days after the initial application, all plants in the test were examined by a single practiced technician to evaluate percent inhibition. Treatments and corresponding percent inhibitions are given in Table 9.

TABLE 9

| Initial application 93 l/ha | | Glyphosate rate | Subsequent application 93 l/ha | % Inhibition |
|---|---|---|---|---|
| herbicide | accession agent | g a.e./ha | accession agent | GLXMA |
| Formulation A | none | 250 | none | 72 |
| Formulation A | none | 500 | none | 93 |
| Formulation A | none | 800 | none | 94 |
| Formulation A | 0.125% L-77 | 250 | none | 45 |
| Formulation A | 0.25% L-77 | 250 | none | 44 |
| Formulation A | 0.5% L-77 | 250 | none | 45 |
| Formulation A | 1.0% L-77 | 250 | none | 61 |
| Formulation A | none | 250 | 0.125% L-77 at ~0.05 hr | 74 |
| Formulation A | none | 250 | 0.25% L-77 at ~0.05 hr | 59 |
| Formulation A | none | 250 | 0.5% L-77 at ~0.05 hr | 60 |
| Formulation A | none | 250 | 1.0% L-77 at ~0.05 hr | 46 |
| Formulation A | none | 250 | 0.125% L-77 at 4 hrs | 76 |
| Formulation A | none | 250 | 0.25% L-77 at 4 hrs | 74 |
| Formulation A | none | 250 | 0.5% L-77 at 4 hrs | 67 |
| Formulation A | none | 250 | 1.0% L-77 at 4 hrs | 70 |
| Formulation A | none | 250 | 0.125% L-77 at 8 hrs | 71 |
| Formulation A | none | 250 | 0.25% L-77 at 8 hrs | 62 |

TABLE 9-continued

| Initial application 93 l/ha | | Glyphosate rate | Subsequent application 93 l/ha | % Inhibition |
|---|---|---|---|---|
| herbicide | accession agent | g a.e./ha | accession agent | GLXMA |
| Formulation A | none | 250 | 0.5% L-77 at 8 hrs | 67 |
| Formulation A | none | 250 | 1.0% L-77 at 8 hrs | 67 |
| Formulation A | none | 250 | 0.125% L-77 at 24 hrs | 75 |
| Formulation A | none | 250 | 0.25% L-77 at 24 hrs | 75 |
| Formulation A | none | 250 | 0.5% L-77 at 24 hrs | 69 |
| Formulation A | none | 250 | 1.0% L-77 at 24 hrs | 66 |

Silwet L-77 in tank mix was strongly antagonistic to the effectiveness of the herbicidal composition in soybean. This antagonism was overcome through sequential application after four hours.

Example 10

Downy broom (*Bromus tectorum*, BROTE) and annual ryegrass (*Lolium multiflorum*, LOLMG) plants were grown in pots, maintained in a greenhouse and treated with initial and subsequent applications by procedures exactly as described for Example 1, except where otherwise noted below. Greenhouse temperature was maintained at approximately 21° C. during the day and 16° C. during the night.

The experimental design included only two replicate pots per treatment. Initial applications of Formulation A, alone or in tank mix with an accession agent, were applied 26 days after planting. Formulation A was applied without accession agent at a range of rates from 100 to 800 g a.e./ha. When an accession agent was included in the treatment, either in tank mix or as a subsequent application, Formulation A was tested only at 100, 200 and 300 g a.e./ha. This Example includes as accession agent an aqueous solution containing 0.5% Silwet L-77. The time interval between initial and subsequent applications was varied from about 0.05 to 3 hours.

Twenty days after the initial application, all plants in the test were examined by a single practiced technician to evaluate percent inhibition. Treatments and corresponding percent inhibitions are given in Table 10.

TABLE 10

| Initial application 93 l/ha | | Glyphosate rate | Subsequent application 93 l/ha | % Inhibition | |
|---|---|---|---|---|---|
| herbicide | accession agent | g a.e./ha | accession agent 0.5% L-77 | BROTE | LOLMG |
| Formulation A | none | 100 | none | 35 | 17 |
| Formulation A | none | 200 | none | 64 | 60 |
| Formulation A | none | 300 | none | 83 | 85 |
| Formulation A | none | 400 | none | 71 | 83 |
| Formulation A | none | 500 | none | 94 | 100 |
| Formulation A | none | 600 | none | 94 | 100 |
| Formulation A | none | 800 | none | 100 | 100 |
| Formulation A | 0.5% L-77 | 100 | none | 3 | 0 |
| Formulation A | 0.5% L-77 | 200 | none | 18 | 38 |
| Formulation A | 0.5% L-77 | 300 | none | 45 | 55 |
| Formulation A | none | 100 | at ~0.05 hr | 30 | 18 |
| Formulation A | none | 200 | at ~0.05 hr | 68 | 70 |
| Formulation A | none | 300 | at ~0.05 hr | 78 | 92 |
| Formulation A | none | 100 | at 1 hr | 38 | 42 |
| Formulation A | none | 200 | at 1 hr | 65 | 82 |
| Formulation A | none | 300 | at 1 hr | 79 | 85 |
| Formulation A | none | 100 | at 3 hrs | 53 | 85 |
| Formulation A | none | 200 | at 3 hrs | 81 | 80 |
| Formulation A | none | 300 | at 3 hrs | 97 | 90 |

The data in Table 10 show better herbicidal results in the sequential process of this invention than in the comparative tank mix treatment as applied to both downy brome and annual ryegrass. Substantial tank mix antagonism is eliminated or reversed, with the best results for application of the Silwet L-77 accession agent obtained three hours after application of the herbicide.

Example 11

Velvetleaf (*Abutilon theophrasti*, ABUTH) and Japanese millet, a form of barnyardgrass (*Echinochloa crus-galli*, ECHCF) plants were grown in pots, maintained in a greenhouse and treated with initial and subsequent applications by procedures exactly as described for Example 1, except where otherwise noted below.

Initial applications of Formulations A and B, alone or in tank mix with an accession agent, were applied on the same day, 19 days after planting velvetleaf and 14 days after planting Japanese millet. Formulations were applied without accession agent at a range of rates from 200 to 600 g a.e./ha. When an accession agent was included in the treatment, either in tank mix or as a subsequent application, formulations were tested only at the lowest rate. This Example includes as accession agent an aqueous solution containing 0.5% Silwet L-77. The time interval between initial and subsequent applications was 4 hours.

Nineteen days after the initial application, all plants in the test were examined by a single practiced technician to evaluate percent inhibition. Treatments and corresponding percent inhibitions are given in Table 11.

TABLE 11

| Initial application 93 l/ha | | Glyphosate | Subsequent application 93 l/ha | % Inhibition | |
|---|---|---|---|---|---|
| herbicide | accession agent | rate g a.e./ha | accession agent 0.5% L-77 | ABUTH | ECHCF |
| Formulation A | none | 200 | none | 40 | 79 |
| Formulation A | none | 300 | none | 71 | 100 |
| Formulation A | none | 400 | none | 89 | 100 |
| Formulation A | none | 600 | none | 97 | 100 |
| Formulation A | 0.5% L-77 | 200 | none | 84 | 16 |
| Formulation A | none | 200 | at 4 hrs | 83 | 77 |
| Formulation B | none | 200 | none | 12 | 57 |
| Formulation B | none | 300 | none | 22 | 52 |
| Formulation B | none | 400 | none | 60 | 55 |
| Formulation B | none | 600 | none | 67 | 89 |
| Formulation B | 0.5% L-77 | 200 | none | 87 | 12 |
| Formulation B | none | 200 | at 4 hrs | 86 | 16 |

The data in Table 11 show, in the case of Formulation A, strong enhancement of velvetleaf control by glyphosate when Silwet L-77 is added in tank mix. At the same time, the data show serious antagonism of Japanese millet control with the same tank mix treatment. This is a dramatic illustration of the major problem of using the prior art method wherein an accession agent is tank mixed or coformulated with a glyphosate herbicide. Attempts to gain enhancement on one species, in this Example velvetleaf, are confounded by the resulting antagonism on another species, in this Example Japanese millet. It will be noted that the method of the present invention, where the accession agent is applied sequentially 4 hours after application of the glyphosate herbicide, gives enhancement of velvetleaf control equal to that provided by the tank mix, yet eliminates the antagonism of Japanese millet control seen with the tank mix treatment.

In this Example, antagonism was not overcome by sequential application of accession agent after Formulation B. As noted above, Formulation B contains no surfactant.

Example 12

Velvetleaf (*Abutilon theophrasti*, ABUTH) and Japanese millet (*Echinochloa crus-galli*, ECHCF) plants were grown in pots, maintained in a greenhouse and treated with initial and subsequent applications by procedures exactly as described for Example 1, except where otherwise noted below.

Initial applications of Formulations A and B, and of glyphosate acid, alone or in tank mix with an accession agent, were applied on the same day, 17 days after planting velvetleaf and 20 days after planting Japanese millet. Glyphosate acid was not prepared as a concentrate formulation but was simply dissolved in water to make the dilute spray solutions of this Example. Formulations and glyphosate acid were applied without accession agent at a range of rates from 250 to 800 g a.e./ha. When an accession agent was included in the treatment, either in tank mix or as a subsequent application, formulations were tested only at 250 and 500 g a.e./ha. This Example includes as accession agent an aqueous solution containing 0.5% Silwet L-77. Initial applications were made in a spray volume of 93 l/ha, and subsequent applications in a spray volume of 280 l/ha. The time interval between initial and subsequent applications was 4 hours.

Twenty days after the initial application, all plants in the test were examined by a single practiced technician to evaluate percent inhibition. Treatments and corresponding percent inhibitions are given in Table 12.

TABLE 12

| Initial application 93 l/ha | | Glyphosate | Subsequent application 280 l/ha | % Inhibition | |
|---|---|---|---|---|---|
| herbicide | accession agent | rate g a.e./ha | accession agent 0.5% L-77 | ABUTH | ECHCF |
| Formulation A | none | 250 | none | 39 | 85 |
| Formulation A | none | 500 | none | 67 | 85 |
| Formulation A | none | 800 | none | 88 | 100 |
| Formulation A | 0.5% L-77 | 250 | none | 65 | 40 |
| Formulation A | 0.5% L-77 | 500 | none | 89 | 21 |
| Formulation A | none | 250 | at 4 hrs | 89 | 46 |
| Formulation A | none | 500 | at 4 hrs | 92 | 57 |

TABLE 12-continued

| | Initial application 93 l/ha | | Glyphosate | Subsequent application 280 l/ha | % Inhibition | |
|---|---|---|---|---|---|---|
| herbicide | accession agent | | rate g a.e./ha | accession agent 0.5% L-77 | ABUTH | ECHCF |
| Formulation B | none | | 250 | none | 13 | 24 |
| Formulation B | none | | 500 | none | 39 | 77 |
| Formulation B | none | | 800 | none | 53 | 93 |
| Formulation B | 0.5% L-77 | | 250 | none | 76 | 25 |
| Formulation B | 0.5% L-77 | | 500 | none | 92 | 49 |
| Formulation B | none | | 250 | at 4 hrs | 77 | 28 |
| Formulation B | none | | 500 | at 4 hrs | 89 | 21 |
| glyphosate acid | none | | 250 | none | 17 | 7 |
| glyphosate acid | none | | 500 | none | 7 | 10 |
| glyphosate acid | none | | 800 | none | 18 | 17 |
| glyphosate acid | 0.5% L-77 | | 250 | none | 64 | 12 |
| glyphosate acid | 0.5% L-77 | | 500 | none | 42 | 23 |
| glyphosate acid | none | | 250 | 0.5% L-77 | 78 | 7 |
| glyphosate acid | none | | 500 | 0.5% L-77 | 84 | 21 |

The data for glyphosate acid in this Example show an unusually low level of inhibition, especially on barnyardgrass. It is possible that the glyphosate acid was not fully dissolved in the spray solution at the time of spraying.

Example 13

Velvetleaf (*Abutilon theophrasti*, ABUTH) and Japanese millet (*Echinochloa crus-galli*, ECHCF) plants were grown in pots, maintained in a greenhouse and treated with initial and subsequent applications by procedures exactly as described for Example 1, except where otherwise noted below.

Initial applications of Formulations A, alone or in tank mix with an accession agent, were applied on the same day, 13 days after planting velvetleaf and 16 days after planting Japanese millet. Formulation A was applied without accession agent at a range of rates from 200 to 500 g a.e./ha. When an accession agent was included in the treatment, either in tank mix or as a subsequent application, Formulation A was tested only at the lowest rate.

Three different spray volumes were used for initial and subsequent applications. In one set of treatments, the initial spray volume was 93 l/ha; in a second set of treatments 47 l/ha; and in a third set of treatments 28 l/ha. For each initial spray volume, three subsequent application spray volumes were tested, again 93, 47 and 28 l/ha. Accession agents in this Example were aqueous solutions containing Silwet L-77. For each spray volume tested, three Silwet L-77 concentrations were used. These were set in such a way as to provide approximately equal dosage rates (200, 300 and 600 g/ha) of Silwet L-77 across different spray volumes. The time interval between initial and subsequent applications was 4 hours.

Twenty days after the initial application, all plants in the test were examined by a single practiced technician to evaluate percent inhibition. Treatments and corresponding percent inhibitions are given in Tables 13a, 13b and 13c. Each table relates to one initial application spray volume.

TABLE 13a

| | Initial application 93 l/ha | | Glyphosate | Subsequent application 280 l/ha | % Inhibition | |
|---|---|---|---|---|---|---|
| herbicide | accession agent | | rate g a.e./ha | accession agent 0.5% L-77 | ABUTH | ECHCF |
| Formulation A | none | | 200 | none | 98 | 96 |
| Formulation A | none | | 300 | none | 96 | 100 |
| Formulation A | none | | 500 | none | 100 | 100 |
| Formulation A | 0.21% L-77 | | 200 | none | 79 | 33 |
| Formulation A | 0.31% L-77 | | 200 | none | 96 | 22 |
| Formulation A | 0.63% L-77 | | 200 | none | 98 | 25 |
| Formulation A | none | | 200 | 0.21% L-77, 93 l/ha | 93 | 94 |
| Formulation A | none | | 200 | 0.31% L-77, 93 l/ha | 93 | 99 |
| Formulation A | none | | 200 | 0.63% L-77, 93 l/ha | 97 | 99 |
| Formulation A | none | | 200 | 0.42% L-77, 47 l/ha | 86 | 98 |
| Formulation A | none | | 200 | 0.63% L-77, 47 l/ha | 95 | 96 |
| Formulation A | none | | 200 | 1.25% L-77, 47 l/ha | 86 | 91 |
| Formulation A | none | | 200 | 0.64% L-77, 28 l/ha | 87 | 99 |
| Formulation A | none | | 200 | 0.98% L-77, 28 l/ha | 86 | 100 |
| Formulation A | none | | 200 | 1.95% L-77, 28 l/ha | 75 | 96 |

TABLE 13b

| Initial application 93 l/ha | | Glyphosate rate | Subsequent application at 4 hours | % Inhibition | |
|---|---|---|---|---|---|
| herbicide | accession agent | g a.e./ha | accession agent spray volume | ABUTH | ECHCF |
| Formulation A | none | 200 | none | 95 | 100 |
| Formulation A | none | 300 | none | 100 | 96 |
| Formulation A | none | 500 | none | 100 | 100 |
| Formulation A | 0.21% L-77 | 200 | none | 80 | 76 |
| Formulation A | 0.31% L-77 | 200 | none | 93 | 55 |
| Formulation A | 0.63% L-77 | 200 | none | 95 | 49 |
| Formulation A | none | 200 | 0.21% L-77, 93 l/ha | 93 | 96 |
| Formulation A | none | 200 | 0.31% L-77, 93 l/ha | 95 | 97 |
| Formulation A | none | 200 | 0.63% L-77, 93 l/ha | 91 | 99 |
| Formulation A | none | 200 | 0.42% L-77, 47 l/ha | 98 | 100 |
| Formulation A | none | 200 | 0.63% L-77, 47 l/ha | 97 | 98 |
| Formulation A | none | 200 | 1.25% L-77, 47 l/ha | 95 | 95 |
| Formulation A | none | 200 | 0.64% L-77, 28 l/ha | 92 | 95 |
| Formulation A | none | 200 | 0.98% L-77, 28 l/ha | 94 | 98 |
| Formulation A | none | 200 | 1.95% L-77, 28 l/ha | 93 | 100 |

TABLE 13c

| Initial application 93 l/ha | | Glyphosate rate | Subsequent application at 4 hours | % Inhibition | |
|---|---|---|---|---|---|
| herbicide | accession agent | g a.e./ha | accession agent spray volume | ABUTH | ECHCF |
| Formulation A | none | 200 | none | 99 | 100 |
| Formulation A | none | 3 00 | none | 100 | 100 |
| Formulation A | none | 500 | none | 100 | 100 |
| Formulation A | 0.21% L-77 | 200 | none | 100 | 85 |
| Formulation A | 0.31% L-77 | 200 | none | 99 | 62 |
| Formulatidn A | 0.63% L-77 | 200 | none | 96 | 85 |
| Formulation A | none | 200 | 0.21% L-77, 93 l/ha | 95 | 99 |
| Formulation A | none | 200 | 0.31% L-77, 93 l/ha | 96 | 98 |
| Formulation A | none | 200 | 0.63% L-77, 93 l/ha | 98 | 100 |
| Formulation A | none | 200 | 0.42% L-77, 47 l/ha | 91 | 95 |
| Formulation A | none | 200 | 0.63% L-77, 47 l/ha | 99 | 100 |
| Formulation A | none | 200 | 1.25% L-77, 47 l/ha | 95 | 98 |
| Formulation A | none | 200 | 0.64% L-77, 28 l/ha | 92 | 90 |
| Formulation A | none | 200 | 0.98% L-77, 28 l/ha | 80 | 93 |
| Formulation A | none | 200 | 1.95% L-77, 28 l/ha | 71 | 92 |

Example 14

Velvetleaf (*Abutilon theophrasti*, ABUTH) and Japanese millet (*Echinochloa crus-galli*, ECHCF) plants were grown in pots, maintained in a greenhouse and treated with initial and subsequent applications by procedures exactly as described for Example 1, except where otherwise noted below.

Initial applications of Formulation A, alone or in tank mix with an accession agent, were applied on the same day, 15 days after planting velvetleaf and 17 days after planting Japanese millet. Formulation A was applied without accession agent at a range of rates from 150 to 750 g a.e./ha. When an accession agent was included in the treatment, either in tank mix or as a subsequent application, Formulation A was tested at a range of rates from 150 to 550 g a.e./ha. This Example includes as accession agent an aqueous solution containing 0.5% Silwet L-77. The time interval between initial and subsequent applications was varied from about 0.05 to 24 hours.

Nineteen days after the initial application, all plants in the test were examined by a single practiced technician to evaluate percent inhibition. Treatments and corresponding percent inhibitions are given in Table 14.

TABLE 14

| Initial application 93 l/ha | | Glyphosate rate | Subsequent application 280 l/ha | % Inhibition | |
|---|---|---|---|---|---|
| herbicide | accession agent | g a.e./ha | accession agent 0.5% L-77 | ABUTH | ECHCF |
| Formulation A | none | 150 | none | 6 | 78 |
| Formulation A | none | 250 | none | 49 | 100 |
| Formulation A | none | 350 | none | 67 | 100 |
| Formulation A | none | 550 | none | 90 | 100 |
| Formulation A | none | 750 | none | 100 | 100 |
| Formulation A | 0.5% L-77 | 150 | none | 51 | 7 |
| Formulation A | 0.5% L-77 | 250 | none | 68 | 9 |
| Formulation A | 0.5% L-77 | 350 | none | 80 | 10 |
| Formulation A | 0.5% L-77 | 550 | none | 94 | 35 |
| Formulation A | none | 150 | at ~0.05 hr | 51 | 13 |
| Formulation A | none | 250 | at ~0.05 hr | 63 | 75 |
| Formulation A | none | 350 | at ~0.05 hr | 84 | 72 |
| Formulation A | none | 550 | at ~0.05 hr | 92 | 97 |
| Formulation A | none | 150 | at 4 hrs | 58 | 59 |
| Formulation A | none | 250 | at 4 hrs | 79 | 91 |
| Formulation A | none | 350 | at 4 hrs | 82 | 90 |
| Formulation A | none | 550 | at 4 hrs | 92 | 95 |
| Formulation A | none | 150 | at 8 hrs | 56 | 52 |
| Formulation A | none | 250 | at 8 hrs | 79 | 59 |
| Formulation A | none | 350 | at 8 hrs | 84 | 79 |
| Formulation A | none | 550 | at 8 hrs | 96 | 98 |
| Formulation A | none | 150 | at 24 hrs | 69 | 42 |
| Formulation A | none | 250 | at 24 hrs | 84 | 79 |
| Formulation A | none | 350 | at 24 hrs | 96 | 79 |
| Formulation A | none | 550 | at 24 hrs | 100 | 97 |

Example 15

Velvetleaf (*Abutilon theophrasti*, ABUTH) and Japanese millet (*Echinochloa crus-galli*, ECHCF) plants were grown in pots, maintained in a greenhouse and treated with initial and subsequent applications by procedures exactly as described for Example 1, except where otherwise noted below.

Initial applications of Formulations A and B, alone or in tank mix with an accession agent, were applied on the same day, 17 days after planting velvetleaf and 19 days after planting Japanese millet. Formulations were applied without accession agent at a range of rates from 350 to 850 g a.e./ha. When an accession agent was included in the treatment, either in tank mix or as a subsequent application, formulations were tested only at the lowest rate. This Example includes as accession agents aqueous solutions containing Fluorad FC-98 or Fluorad FC-99 at a range of concentrations from 0.03% to 0.48%. Fluorad FC-98 and Fluorad FC-99 are perfluoroalkyl sulfonate surfactants, with potassium and amine counterions respectively, of 3M Company and are abbreviated in tables herein by omission of the 'Fluorad' trademark. The time interval between initial and subsequent applications was 4 hours.

Fifteen days after the initial application, all plants in the test were examined by a single practiced technician to evaluate percent inhibition. Treatments and corresponding percent inhibitions are given in Table 15.

TABLE 15

| Initial application 93 l/ha | | Glyphosate rate | Subsequent application 93 l/ha | % Inhibition | |
|---|---|---|---|---|---|
| herbicide | accession agent | g a.e./ha | accession agent at 4 hrs | ABUTH | ECHCF |
| Formulation A | none | 350 | none | 48 | 58 |
| Formulation A | none | 450 | none | 57 | 83 |
| Formulation A | none | 550 | none | 68 | 97 |
| Formulation A | none | 650 | none | 77 | 99 |
| Formulation A | none | 850 | none | 87 | 99 |
| Formulation A | 0.03% FC-98 | 350 | none | 42 | 33 |
| Formulation A | 0.06% FC-98 | 350 | none | 28 | 22 |
| Formulation A | 0.12% FC-98 | 350 | none | 25 | 22 |
| Formulation A | 0.24% FC-98 | 350 | none | 33 | 28 |
| Formulation A | 0.48% FC-98 | 350 | none | 22 | 27 |
| Formulation A | none | 350 | 0.03% FC-98 | 57 | 43 |
| Formulation A | none | 350 | 0.06% FC-98 | 53 | 63 |

TABLE 15-continued

| | Initial application 93 l/ha | Glyphosate | Subsequent application 93 l/ha | % Inhibition | |
|---|---|---|---|---|---|
| herbicide | accession agent | rate g a.e./ha | accession agent at 4 hrs | ABUTH | ECHCF |
| Formulation A | none | 350 | 0.12% FC-98 | 42 | 65 |
| Formulation A | none | 350 | 0.24% FC-98 | 40 | 57 |
| Formulation A | none | 350 | 0.48% FC-98 | 37 | 77 |
| Formulation A | 0.03% FC-99 | 350 | none | 27 | 30 |
| Formulation A | 0.06% FC-99 | 350 | none | 22 | 22 |
| Formulation A | 0.12% FC-99 | 350 | none | 22 | 10 |
| Formulation A | 0.24% FC-99 | 350 | none | 28 | 10 |
| Formulation A | 0.48% FC-99 | 350 | none | 42 | 10 |
| Formulation A | none | 350 | 0.03% FC-99 | 47 | 80 |
| Formulation A | none | 350 | 0.06% FC-99 | 48 | 88 |
| Formulation A | none | 350 | 0.12%FC-99 | 45 | 67 |
| Formulation A | none | 350 | 0.24% FC-99 | 40 | 67 |
| Formulation A | none | 350 | 0.48% FC-99 | 48 | 68 |
| Formulation B | none | 350 | none | 27 | 28 |
| Formulation B | none | 450 | none | 30 | 32 |
| Formulation B | none | 550 | none | 42 | 33 |
| Formulation B | none | 650 | none | 60 | 37 |
| Formulation B | none | 850 | none | 68 | 40 |
| Formulation B | 0.03% FC-98 | 350 | none | 22 | 22 |
| Formulation B | 0.06% FC-98 | 350 | none | 20 | 20 |
| Formulation B | 0.12% FC-98 | 350 | none | 22 | 30 |
| Formulation B | 0.24% FC-98 | 350 | none | 27 | 30 |
| Formulation B | 0.48% FC-98 | 350 | none | 37 | 25 |
| Formulation B | none | 350 | 0.03% FC-98 | 27 | 38 |
| Formulation B | none | 350 | 0.06% FC-98 | 30 | 38 |
| Formulation B | none | 350 | 0.12% FC-98 | 28 | 35 |
| Formulation B | none | 350 | 0.24% FC-98 | 32 | 30 |
| Formulation B | none | 350 | 0.48% FC-98 | 33 | 68 |
| Formulation B | 0.03% FC-99 | 350 | none | 25 | 22 |
| Formulation B | 0.06% FC-99 | 350 | none | 27 | 22 |
| Formulation B | 0.12% FC-99 | 350 | none | 30 | 25 |
| Formulation B | 0.24% FC-99 | 350 | none | 42 | 15 |
| Formulation B | 0.48% FC-99 | 350 | none | 58 | 12 |
| Formulation B | none | 350 | 0.03% FC-99 | 27 | 48 |
| Formulation B | none | 350 | 0.06% FC-99 | 32 | 57 |
| Formulation B | none | 35Q | 0.12% FC-99 | 27 | 45 |
| Formulation B | none | 350 | 0.24% FC-99 | 25 | 37 |
| Formulation B | none | 350 | 0.48% FC-99 | 35 | 32 |

For the herbicidal compositions containing a surfactant coformulant, the FC-98 and FC-99 surfactants in tank mix were significantly antagonistic to the effectiveness of the herbicidal composition in Japanese millet, and somewhat less antagonistic in velvetleaf. This antagonism was overcome through sequential application, which (in some cases, especially in Japanese millet) gave significant improvement of effectiveness over the herbicidal composition applied without FC-98 or FC-99. For the herbicidal composition (Formulation B) which does not contain a surfactant coformulant, antagonism was less pronounced, but sequential application of accession agent generally gave some improvement of effectiveness over comparable tank mix application.

Example 16

Velvetleaf (*Abutilon theophrasti*, ABUTH) and Japanese millet (*Echinochloa crus-galli*, ECHCF) plants were grown in pots, maintained in a greenhouse and treated with initial and subsequent applications by procedures exactly as described for Example 1, except where otherwise noted below.

The experimental design included four replicate pots per treatment. Initial applications of Formulation B, alone or in tank mix with an accession agent, were applied on the same day, 18 days after planting velvetleaf and 20 days after planting Japanese millet. Formulation B was applied without accession agent at a range of rates from 350 to 650 g a.e./ha. When an accession agent was included in the treatment, either in tank mix or as a subsequent application, Formulation B was tested only at the lowest rate. This Example includes several candidate accession agents, all aqueous solutions of surfactants or of surfactant blends at a total surfactant concentration of 0.125% or 0.5%. The time interval between initial and subsequent applications was 4 hours.

Surfactants in the accession agents of this Example included Silwet L-77, Fluorad FC-98 and Fluorad FC-135, a product of 3M Company disclosed in McCutcheon's Emulsifiers and Detergents, North American Edition, 1994 (hereinafter, McCutcheon's), as fluorinated alkyl quaternary ammonium iodides. Other surfactants used in this Example included the following:

Surfynol 465 of Air Products and Chemicals, Inc.: disclosed in McCutcheon's (loc. cit.) as ethoxylated tetramethyl decynediol, abbreviated in tables herein as 'Surf 465'.

Agrimul PG 2069 of Henkel Corporation: disclosed in Henkel Technical Bulletin 105B, 1993, as a composition containing 50% alkyl polyglucoside, abbreviated in tables herein as 'PG 2069'. A newsletter from Henkel dated July 1996 and titled "Solutions in the field: Agrimul PG surfactants" discloses that Agrimul PG 2069 has a C9–11 alkyl chain and that its degree of polymerization (moles glucose per mole surfactant) is 1.6.

Silamine C-100 of Siltech Inc.: abbreviated in tables herein as 'Silamine'.

Seventeen days after the initial application, all plants in the test were examined by a single practiced technician to evaluate percent inhibition. Treatments and corresponding percent inhibitions are given in Table 16.

millet. Formulations D and E were not prepared as concentrate formulations but were made by simply dissolving the respective salts in water to make the dilute spray solutions of this Example. Formulations were applied without accession agent at a range of rates from 200 to 800 g a.e./ha. When an accession agent was included in the treatment, either in

TABLE 16

| Initial application 93 l/ha | | Glyphosate rate | Subsequent application 93 l/ha | % Inhibition | |
|---|---|---|---|---|---|
| herbicide | accession agent | g a.e./ha | accession agent at 4 hrs | ABUTH | ECHCF |
| Formulation B | none | 350 | none | 51 | 24 |
| Formulation B | none | 450 | none | 68 | 25 |
| Formulation B | none | 650 | none | 77 | 66 |
| Formulation B | 0.125% L-77 | 350 | none | 29 | 5 |
| Formulation B | 0.5% L-77 | 350 | none | 87 | 0 |
| Formulation B | none | 350 | 0.125% L-77 | 36 | 29 |
| Formulation B | none | 350 | 0.5% L-77 | no data | 29 |
| Formulation B | 0.125% FC-98 | 350 | none | 43 | 11 |
| Formulation B | 0.5% FC-98 | 350 | none | 55 | 12 |
| Formulation B | none | 350 | 0.125% FC-98 | 44 | 25 |
| Formulation B | none | 350 | 0.5% FC-98 | 67 | 20 |
| Formulation B | 0.125% FC-135 | 350 | none | 68 | 35 |
| Formulation B | 0.5% FC-135 | 350 | none | 80 | 75 |
| Formulation B | none | 350 | 0.125% FC-135 | 77 | 24 |
| Formulation B | none | 350 | 0.5% FC-135 | 64 | 29 |
| Formulation B | 0.125% Surf 465 | 350 | none | 67 | 33 |
| Formulation B | 0.5% Surf 465 | 350 | none | 61 | 30 |
| Formulation B | none | 350 | 0.125% Surf 465 | 58 | 27 |
| Formulation B | none | 350 | 0.5% Surf 465 | 53 | 29 |
| Formulation B | 0.125% Surf465 + L-77, 1:1 | 350 | none | 25 | 12 |
| Formulation B | 0.5% Surf 465 + L-77, 1:1 | 350 | none | 79 | 26 |
| Formulation B | none | 350 | 0.125% Surf 465 + L-77,1:1 | 43 | 31 |
| Formulation B | none | 350 | 0.5% Surf 465 + L-77,1:1 | 55 | 17 |
| Formulation B | 0.125% PG 2069 | 350 | none | 53 | 43 |
| Formulation B | 0.5% PG 2069 | 350 | none | 68 | 55 |
| Formulation B | none | 350 | 0.125% PG 2069 | 66 | 43 |
| Formulation B | none | 350 | 0.5% PG 2069 | 61 | 27 |
| Formulation B | 0.125% PG 2069 + L-77, 1:1 | 350 | none | 41 | 36 |
| Formulation B | 0.5% PG 2069 + L-77, 1:1 | 350 | none | 71 | 12 |
| Formulation B | none | 350 | 0.125% PG 2069 + L-77, 1:1 | 49 | 18 |
| Formulation B | none | 350 | 0.5% PG 2069 + L-77, 1:1 | 58 | 47 |
| Formulation B | 0.125% Silamine | 350 | none | 58 | 46 |
| Formulation B | 0.5% Silamine | 350 | none | 69 | 39 |
| Formulation B | none | 350 | 0.125% Silamine | 55 | 25 |
| Formulation B | none | 350 | 0.5% Silamine | 57 | 45 |

Example 17

Velvetleaf (*Abutilon theophrasti*, ABUTH) and Japanese millet (*Echinochloa crus-galli*, ECHCF) plants were grown in pots, maintained in a greenhouse and treated with initial and subsequent applications by procedures exactly as described for Example 1, except where otherwise noted below.

Initial applications of Formulation B, the disodium salt of glyphosate (Formulation D) and the trisodium salt of glyphosate (Formulation E), alone or in tank mix with an accession agent, were applied on the same day, 17 days after planting velvetleaf and 19 days after planting Japanese millet. Formulations D and E were not prepared as concentrate formulations but were made by simply dissolving the respective salts in water to make the dilute spray solutions of this Example. Formulations were applied without accession agent at a range of rates from 200 to 800 g a.e./ha. When an accession agent was included in the treatment, either in tank mix or as a subsequent application, comparative testing was conducted only at 200 and 400 g a.e./ha. This Example includes as accession agent an aqueous solution containing 0.5% Silwet L-77. The time interval between initial and subsequent applications was about 0.05 or 3 hours.

Seventeen days after the initial application, all plants in the test were examined by a single practiced technician to evaluate percent inhibition. Treatments and corresponding percent inhibitions are given in Table 17.

TABLE 17

| Herbicide | Initial application 93 l/ha accession agent | Glyphosate rate g a.e./ha | Subsequent application 93 l/ha accession agent 0.5% L-77 | % Inhibition ABUTH | ECHCF |
|---|---|---|---|---|---|
| Formulation B | none | 200 | none | 22 | 30 |
| Formulation B | none | 400 | none | 42 | 61 |
| Formulation B | none | 600 | none | 77 | 83 |
| Formulation B | none | 800 | none | 69 | 90 |
| Formulation B | 0.5% L-77 | 200 | none | 83 | 3 |
| Formulation B | 0.5% L-77 | 400 | none | 89 | 43 |
| Formulation B | none | 200 | at ~0.05 hr | 78 | 7 |
| Formulation B | none | 400 | at ~0.05 hr | 79 | 27 |
| Formulation B | none | 200 | at 3 hrs | 81 | 35 |
| Formulation B | none | 400 | at 3 hrs | 86 | 37 |
| Formulation D | none | 200 | none | 2 | 21 |
| Formulation D | none | 400 | none | 5 | 50 |
| Formulation D | none | 600 | none | 43 | 47 |
| Formulation D | none | 800 | none | 71 | 60 |
| Formulation D | 0.5% L-77 | 200 | none | 77 | 0 |
| Formulation D | 0.5% L-77 | 400 | none | 82 | 10 |
| Formulation D | none | 200 | at ~0.05 hr | 74 | 10 |
| Formulation D | none | 400 | at ~0.05 hr | 93 | 31 |
| Formulation D | none | 200 | at 3 hrs | 77 | 16 |
| Formulation D | none | 400 | at 3 hrs | 83 | 19 |
| Formulation B | none | 200 | none | 0 | 2 |
| Formulation E | none | 400 | none | 31 | 8 |
| Formulation E | none | 600 | none | 56 | 32 |
| Fonnulation E | none | 800 | none | 64 | 35 |
| Formulation E | 0.5% L-77 | 200 | none | 69 | 0 |
| Formulation E | 0.5% L-77 | 400 | none | 75 | 3 |
| Forrnulation E | none | 200 | ~0.05 hrs | 75 | 0 |
| Forrnulation E | none | 400 | ~0.05 hrs | 86 | 17 |
| Formulation E | none | 200 | 3 hrs | 82 | 2 |
| Formulation E | none | 400 | 3 hrs | 83 | 33 |

Example 18

Velvetleaf (*Abutilon theophrasti*, ABUTH) and Japanese millet (*Echinochloa crus-galli*, ECHCF) plants were grown in pots, maintained in a greenhouse and treated with initial and subsequent applications by procedures exactly as described for Example 1, except where otherwise noted below.

Initial applications of Formulation B, and of Formulations F–I as defined below, alone or in tank mix with an accession agent, were applied on the same day, 15–17 days after planting velvetleaf and 17–19 days after planting, Japanese millet. Formulations F, G, H and I are aqueous solutions of the monosodium, monopotassium, monoammonium and mono(trimethylsulfonium) salts respectively of glyphosate. Formulations F and G were not prepared as concentrate formulations but were made by simply dissolving the respective salts in water to make the dilute spray solutions of this Example. Formulation H was prepared from a water soluble granular concentrate of monoammonium glyphosate, containing no surfactant, as sold by Monsanto Company. Formulation I was prepared from an aqueous concentrate product sold in the USA by Zeneca under the trademark Touchdown which is believed to have no coformulated surfactant. All applications of glyphosate salt formulations were made with the addition to the spray solution of 0.09% MON-0818 surfactant of Monsanto Company. Formulations were applied without accession agent at 200 and 400 g, a.e./ha. When an accession agent was included in the treatment, either in tank mix or as a subsequent application, formulations were tested at the same two rates. This Example includes as accession agent an aqueous solution containing 0.5% Silwet L-77. The time interval between initial and subsequent applications was about 0.05 or 3 hours.

Seventeen days after the initial application, all plants in the test were examined by a single practiced technician to evaluate percent inhibition. Treatments and corresponding percent inhibitions are given in Table 18.

TABLE 18

| Herbicide | Initial application 93 l/ha accession agent | Glyphosate rate g a.e./ha | Subsequent application 93 l/ha accession agent 0.5% L-77 | % Inhibition ABUTH | ECHCF |
|---|---|---|---|---|---|
| Formulation B | none | 200 | none | 56 | 91 |
| Formulation B | none | 400 | none | 85 | 100 |
| Formulation B | 0.5% L-77 | 200 | none | 65 | 33 |

TABLE 18-continued

| Herbicide | Initial application 93 1/ha accession agent | Glyphosate rate g a.e./ha | Subsequent application 93 1/ha accession agent 0.5% L-77 | % Inhibition ABUTH | ECHCF |
|---|---|---|---|---|---|
| Formulation B | 0.5% L-77 | 400 | none | 71 | 51 |
| Formulation B | none | 200 | at ~0.05 hr | 83 | 66 |
| Formulation B | rione | 400 | at ~0.05 hr | 91 | 93 |
| Formulation B | none | 200 | at 3 hrs | 43 | 75 |
| Formulation B | none | 400 | at 3 hrs | 81 | 100 |
| Formulation F | none | 200 | none | 36 | 100 |
| Formulation F | none | 400 | none | 85 | 100 |
| Formulation F | 0.5% L-77 | 200 | none | 54 | 36 |
| Formulation F | 0.5% L-77 | 400 | none | 81 | 63 |
| Formulation F | none | 200 | at ~0.05 hr | 51 | 64 |
| Formulation F | none | 400 | at ~0.05 hr | 80 | 91 |
| Formulation F | none | 200 | at 3 hrs | 41 | 73 |
| Formulation F | none | 400 | at 3 hrs | 88 | 100 |
| Formulation G | none | 200 | none | 68 | 93 |
| Formulation G | none | 400 | none | 86 | 100 |
| Formulation G | 0.5% L-77 | 200 | none | 55 | 33 |
| Formulation G | 0.5% L-77 | 400 | none | 80 | 43 |
| Formulation G | none | 200 | ~0.05 hrs | 63 | 50 |
| Formulation G | none | 400 | ~0.05 hrs | 76 | 80 |
| Formulation G | none | 200 | 3 hrs | 46 | 81 |
| Formulation G | none | 400 | 3 hrs | 66 | 99 |
| Formulation H | none | 200 | none | 69 | 93 |
| Formulation H | none | 400 | none | 86 | 100 |
| Formulation H | 0.5% L-77 | 200 | none | 64 | 48 |
| Formulation H | 0.5% L-77 | 400 | none | 78 | 59 |
| Formulation H | none | 200 | ~0.05 hrs | 73 | 69 |
| Formulation H | none | 400 | ~0.05 hrs | 89 | 81 |
| Formulation H | none | 200 | 3 hrs | 40 | 81 |
| Formulation H | none | 400 | 3 hrs | 75 | 99 |
| Formulation I | none | 200 | none | no data | 96 |
| Formulation I | none | 400 | none | no data | 100 |
| Fonnulation I | 0.5% L-77 | 200 | none | no data | 30 |
| Formulation I | 0.5% L-77 | 400 | none | no data | 53 |
| Formulation I | none | 200 | ~0.05 hrs | no data | 75 |
| Formulation J | none | 400 | ~0.05 hrs | no data | 84 |
| Formulation J | none | 200 | 3 hrs | no data | 88 |
| Formulation I | none | 400 | 3 hrs | no data | 89 |

Example 19

Canada thistle (*Cirsium arvense*, CIRAR) plants were grown in pots, maintained in a greenhouse and treated with initial and subsequent applications by procedures exactly as described for Example 1, except where otherwise noted below.

Greenhouse temperature was maintained at approximately 21° C. during the day and 13° C. during the night. Initial applications of Formulations A and B, alone or in tank mix with an accession agent, were applied 40 days after planting. Formulations were each applied without accession agent at 250 and 500 g a.e./ha. When an accession agent was included in the treatment, either in tank mix or as a subsequent application, formulations were tested only at the lower rate. This Example includes as accession agents aqueous solutions containing Silwet L-77 at a range of concentrations from 0.5% to 2.0%. The time interval between initial and subsequent applications was varied from about 0.05 hour to 24 hours.

Twenty-six days after the initial application, all plants in the test were examined by a single practiced technician to evaluate percent inhibition. Treatments and corresponding percent inhibitions are given in Table 19.

TABLE 19

| Herbicide | Initial application 93 1/ha accession agent | Glyphosate rate g a.e./ha | Subsequent application 93 l/ha accession agent 0.5% L-77 | % Inhibition CIRAR |
|---|---|---|---|---|
| Formulation A | none | 250 | none | 66 |
| Formulation A | none | 500 | none | 79 |
| Formulation A | 0.5% L-77 | 250 | none | 52 |

TABLE 19-continued

| Initial application 93 l/ha | | Glyphosate rate | Subsequent application 93 l/ha accession agent | % Inhibition |
|---|---|---|---|---|
| Herbicide | accession agent | g a.e./ha | 0.5% L-77 | CIRAR |
| Formulation A | 1.0% L-77 | 250 | none | 71 |
| Formulation A | 2.0% L-77 | 250 | none | 81 |
| Formulation A | none | 250 | 0.5% L-77 at ~0.05 hr | 80 |
| Formulation A | none | 250 | 1.0% L-77 at ~0.05 hr | 84 |
| Formulation A | none | 250 | 2.0% L-77 at ~0.05 hr | 83 |
| Formulation A | none | 250 | 0.5% L-77 at 4 hrs | 75 |
| Formulation A | none | 250 | 1.0% L-77 at 4 hrs | 93 |
| Formulation A | none | 250 | 2.0% L-77 at 4 hrs | 81 |
| Formulation A | none | 250 | 0.5% L-77 at 24 hrs | 78 |
| Formulation A | none | 250 | 1.0% L-77 at 24 hrs | 73 |
| Formulation A | none | 250 | 2.0% L-77 at 24 hrs | 78 |
| Formulation B | none | 250 | none | 70 |
| Formulation B | none | 500 | none | 77 |
| Formulation B | 0.5% L-77 | 250 | none | 79 |
| Formulation B | 1.0% L-77 | 250 | none | 75 |
| Formulation B | 2.0% L-77 | 250 | none | 71 |
| Formulation B | none | 250 | 0.5% L-77 at ~0.05 hr | 85 |
| Formulation B | none | 250 | 1.0% L-77 at ~0.05 hr | 85 |
| Formulation B | none | 250 | 2.0% L-77 at ~0.05 hr | 75 |
| Formulation B | none | 250 | 0.5% L-77 at 4 hrs | 71 |
| Formulation B | none | 250 | 1.0% L-77 at 4 hrs | 64 |
| Formulation B | none | 250 | 2.0% L-77 at 4 hrs | 80 |
| Formulation B | none | 250 | 0.5% L-77 at 24 hrs | 84 |
| Formulation B | none | 250 | 1.0% L-77 at 24 hrs | 71 |
| Formulation B | none | 250 | 2.0% L-77 at 24 hrs | 80 |

Although Silwet L-77 in tank mix was not significantly antagonistic to herbicidal effectiveness in canada thistle, sequential application of the accession agent gave generally enhanced effectiveness.

Example 20

Soybean (*Glycine max*, GLXMA) plants were grown in pots, maintained in a greenhouse and treated with initial and subsequent applications by procedures exactly as described for Example 1, except where otherwise noted below.

Initial applications of Formulations A and B and glyphosate acid, alone or in tank mix with an accession agent, were applied 16 days after planting. Glyphosate acid was applied in the same way as in Example 12. Formulations were each applied without accession agent at a range of rates from 250 to 800 g a.e./ha. When an accession agent was included in the treatment, either in tank mix or as a subsequent application, formulations were tested only at 250 and 500 g a.e./ha. This Example includes as accession agent an aqueous solution containing 0.5% Silwet L-77. The time interval between initial and subsequent applications was 3 hours.

Twenty days after the initial application, all plants in the test were examined by a single practiced technician to evaluate percent inhibition. Treatments and corresponding percent inhibitions are given in Table 20.

TABLE 20

| Initial application 93 l/ha | | Glyphosate rate | Subsequent application 93 l/ha accession agent | % Inhibition |
|---|---|---|---|---|
| Herbicide | accession agent | g a.e./ha | 0.5% L-77 | GLXMA |
| Formulation A | none | 250 | none | 70 |
| Formulation A | none | 500 | none | 83 |
| Formulation A | none | 800 | none | 92 |
| Formulation A | 0.5% L-77 | 250 | none | 38 |
| Formulation A | 0.5% L-77 | 500 | none | 53 |
| Formulation A | none | 250 | 0.5% L-77 at 3 hrs | 56 |
| Formulation A | none | 500 | 0.5% L-77 at 3 hrs | 66 |
| Formulation B | none | 25Q | none | 17 |
| Formulation B | none | 500 | none | 25 |
| Formulation B | none | 800 | none | 41 |
| Formulation B | 0.5% L-77 | 250 | none | 42 |
| Formulation B | 0.5% L-77 | 500 | none | 54 |
| Formulation B | none | 250 | 0.5% L-77 at 3 hrs | 38 |
| Formulation B | none | 500 | 0.5% L-77 at 3 hrs | 43 |
| glyphosate acid | none | 250 | none | 7 |
| glyphosate acid | none | 500 | none | 3 |
| glyphosate acid | none | 800 | none | 8 |

TABLE 20-continued

| Initial application 93 l/ha | | Glyphosate rate | Subsequent application 93 l/ha accession agent | % Inhibition |
|---|---|---|---|---|
| Herbicide | accession agent | g a.e./ha | 0.5% L-77 | GLXMA |
| glyphosate acid | 0.5% L-77 | 250 | none | 33 |
| glyphosate acid | 0.5% L-77 | 500 | none | 48 |
| glyphosate acid | none | 250 | 0.5% L-77 at 3 hrs | 39 |
| glyphosate acid | none | 500 | 0.5% L-77 at 3 hrs | 28 |

Silwet L-77 in tank mix improved the herbicidal effectiveness of both glyphosate acid and the herbicidal composition (Formulation B) that lacked a surfactant coformulant for soybean. It was somewhat antagonistic for the herbicidal composition that includes a surfactant coformulant, and this antagonism was somewhat reduced through sequential application.

Example 21

Giant ragweed (*Ambrosia trifida*, AMBTR) plants were grown in pots, maintained in a greenhouse and treated with initial and subsequent applications by procedures exactly as described for Example 1, except where otherwise noted below.

Initial applications of Formulations A, B and C, alone or in tank mix with an accession agent, were applied 21 days after planting. Formulations were each applied without accession agent at a range of rates from 200 to 800 g a.e./ha. When an accession agent was included in the treatment, either in tank mix or as a subsequent application, formulations were tested only at 200 and 500 g a.e./ha. This Example includes as accession agent an aqueous solution containing 0.5% Silwet L-77. The time interval between initial and subsequent applications was 3 hours.

Twenty-one days after the initial application, all plants in the test were examined by a single practiced technician to evaluate percent inhibition. Treatments and corresponding percent inhibitions are given in Table 21.

TABLE 21

| Initial application 93 l/ha | | Glyphosate rate | Subsequent application 93 l/ha accession agent | % Inhibition |
|---|---|---|---|---|
| Herbicide | accession agent | g a.e./ha | 0.5% L-77 | AMBTR |
| Formulation A | none | 200 | none | 30 |
| Formulation A | none | 500 | none | 74 |
| Formulation A | none | 800 | none | 93 |
| Formulation A | 0.5% L-77 | 200 | none | 49 |
| Formulation A | 0.5% L-77 | 500 | none | 67 |
| Formulation A | none | 200 | 0.5% L-77 at 3 hrs | 47 |
| Formulation A | none | 500 | 0.5% L-77 at 3 hrs | 93 |
| Formulation B | none | 200 | none | 34 |
| Formulation B | none | 500 | none | 59 |
| Formulation B | none | 800 | none | 98 |
| Formulation B | 0.5% L-77 | 200 | none | 55 |
| Formulation B | 0.5% L-77 | 500 | none | 86 |
| Formulation B | none | 200 | 0.5% L-77 at 3 hrs | 47 |
| Formulation B | none | 500 | 0.5% L-77 at 3 hrs | 90 |
| Formulation C | none | 200 | none | 46 |
| Formulation C | none | 500 | none | 59 |
| Formulation C | none | 800 | none | 92 |
| Formulation C | 0.5% L-77 | 200 | none | 57 |
| Formulation C | 0.5% L-77 | 500 | none | 59 |
| Formulation C | none | 200 | 0.5% L-77 at 3 hrs | 49 |
| Formulation C | none | 500 | 0.5% L-77 at 3 hrs | 79 |

Silwet L-77 in tank mix slightly improved the effectiveness of the herbicidal composition against giant ragweed. Comparable improvement was achieved through sequential application of the accession agent.

Example 22

Hemp sesbania (*Sesbania exaltata*, SEBEX) plants were grown in pots, maintained in a greenhouse and treated with initial and subsequent applications by procedures exactly as described for Example 1, except where otherwise noted below.

Initial applications of Formulations A, B and C, alone or in tank mix with an accession agent, were applied 24 days after planting. Formulations were each applied without accession agent at a range of rates from 200 to 800 g a.e./ha. When an accession agent was included in the treatment, either in tank mix or as a subsequent application, formulations were tested only at 200 and 500 g a.e./ha. This Example includes as accession agent an aqueous solution containing 0.5% Silwet L-77. The time interval between initial and subsequent applications was 3 hours.

Twenty-one days after the initial application, all plants in the test were examined by a single practiced technician to evaluate percent inhibition. Treatments and corresponding percent inhibitions are given in Table 22.

Initial applications of Formulations A, B and C, alone or in tank mix with an accession agent, were applied 26 days

TABLE 22

| Initial application 93 l/ha | | Glyphosate rate | Subsequent application 93 l/ha accession agent | % Inhibition |
|---|---|---|---|---|
| Herbicide | accession agent | g a.e./ha | 0.5% L-77 | SEBEX |
| Formulation A | none | 200 | none | 51 |
| Formulation A | none | 500 | none | 58 |
| Formulation A | none | 800 | none | 73 |
| Formulation A | 0.5% L-77 | 200 | none | 16 |
| Formulation A | 0.5% L-77 | 500 | none | 55 |
| Formulation A | none | 200 | 0.5% L-77 at 3 hrs | 29 |
| Formulation A | none | 500 | 0.5% L-77 at 3 hrs | 62 |
| Formulation B | none | 200 | none | 7 |
| Formulation B | none | 500 | none | 25 |
| Formulation B | none | 800 | none | 27 |
| Formulation B | 0.5% L-77 | 200 | none | 13 |
| Formulation B | 0.5% L-77 | 500 | none | 33 |
| Formulation B | none | 200 | 0.5% L-77 at 3 hrs | 7 |
| Formulation B | none | 500 | 0.5% L-77 at 3 hrs | 28 |
| Formulation C | none | 200 | none | 50 |
| Formulation C | none | 500 | none | 62 |
| Formulation C | none | 800 | none | 77 |
| Formulation C | 0.5% L-77 | 200 | none | 19 |
| Formulation C | 0.5% L-77 | 500 | none | 94 |
| Formulation C | none | 200. | 0.5% L-77 at 3 hrs | 52 |
| Formulation C | none | 500 | 0.5% L-77 at 3 hrs | 48 |

Antagonism was in some cases observed in hemp sesbania for Silwet L-77 in tank mix with herbicidal compositions that employ a surfactant coformulant. In these cases, the antagonism was reduced through sequential application of the accession agent.

Example 23

Sicklepod (*Cassia obtusifolia*, CASOB) plants were grown in pots, maintained in a greenhouse and treated with initial and subsequent applications by procedures exactly as described for Example 1, except where otherwise noted below.

Initial applications of Formulations A, B and C, alone or in tank mix with an accession agent, were applied 26 days after planting. Formulations were each applied without accession agent at a range of rates from 400 to 1000 g a.e./ha. When an accession agent was included in the treatment, either in tank mix or as a subsequent application, formulations were tested only at 400 and 600 g a.e./ha. This Example includes as accession agent an aqueous solution containing 0.5% Silwet L-77. The time interval between initial and subsequent applications was 3 hours.

Eighteen days after the initial application, all plants in the test were examined by a single practiced technician to evaluate percent inhibition. Treatments and corresponding percent inhibitions are given in Table 23.

TABLE 23

| Initial application 93 l/ha | | Glyphosate rate | Subsequent application 93 l/ha accession agent | % Inhibition |
|---|---|---|---|---|
| Herbicide | accession agent | g a.e./ha | 0.5% L-77 | CIRAR |
| Formulation A | none | 400 | none | 62 |
| Formulation A | none | 600 | none | 81 |
| Formulation A | none | 1900 | none | 91 |
| Formulation A | 0.5% L-77 | 400 | none | 30 |
| Formulation A | 0.5% L-77 | 600 | none | 56 |
| Formulation A | none | 400 | 0.5% L-77 at 3 hrs | 66 |
| Formulation A | none | 600 | 0.5% L-77 at 3 hrs | 66 |
| Formulation B | none | 400 | none | 38 |
| Formulation B | none | 600 | none | 37 |
| Formulation B | none | 1000 | none | 44 |
| Formulation B | 0.5% L-77 | 400 | none | 33 |
| Formulation B | 0.5% L-77 | 600 | none | 46 |
| Formulation B | none | 400 | 0.5% L-77 at 3 hrs | 29 |
| Formulation B | none | 600 | 0.5% L-77 at 3 hrs | 23 |
| Formulation C | none | 400 | none | 72 |
| Formulation C | none | 600 | none | 81 |

TABLE 23-continued

| Initial application 93 l/ha | | Glyphosate rate | Subsequent application 93 l/ha | % Inhibition |
|---|---|---|---|---|
| Herbicide | accession agent | g a.e./ha | accession agent | CIRAR |
| Formulation C | none | 1000 | none | 87 |
| Formulation C | 0.5% L-77 | 400 | none | 27 |
| Formulation C | 0.5% L-77 | 600 | none | 26 |
| Formulation C | none | 400 | 0.5% L-77 at 3 hrs | 60 |
| Formulation C | none | 600 | 0.5% L-77 at 3 hrs | 69 |

In sicklepod, s Silwet L-77 in tank mix was significantly antagonistic for those herbicidal compositions that employ a surfactant coformulant. This antagonism was significantly reduced (and often eliminated) through sequential application of the accession agent.

Example 24

Yellow nutsedge (*Cyperus esculentus*, CYPES) plants were grown in pots, maintained in a greenhouse and treated with initial and subsequent applications by procedures exactly as described for Example 1, except where otherwise noted below.

Initial applications of Formulations A, B and C, alone or in tank mix with an accession agent, were applied 21 days after planting. Formulations were each applied without accession agent at a range of rates from 1600 to 3200 g a.e./ha. When an accession agent was included in the treatment, either in tank mix or as a subsequent application, formulations were tested only at 1600 and 2200 g a.e./ha. This Example includes as accession agent an aqueous solution containing 0.5% Silwet L-77. The time interval between initial and subsequent applications was 3 hours.

Twenty-five days after the initial application, all plants in the test were examined by a single practiced technician to evaluate percent inhibition. Treatments and corresponding percent inhibitions are given in Table 24.

In yellow nutsedge, Silwet L-77 in tank mix was mildly antagonistic for those herbicidal compositions that employ a surfactant coformulant. This antagonism was reduced through sequential application of the accession agent.

Example 25

Seedling johnsongrass (*Sorghum halepense*, SORHA) plants were grown in pots, maintained in a greenhouse and treated with initial and subsequent applications by procedures exactly as described for Example 1, except where otherwise noted below.

Initial applications of Formulations A, B and C, alone or in tank mix with an accession agent, were applied 30 days after planting. Formulations were each applied without accession agent at a range of rates from 150 to 400 g a.e./ha. When an accession agent was included in the treatment, either in tank mix or as a subsequent application, formulations were tested only at 150 and 250 g a.e./ha. This Example includes as accession agent an aqueous solution containing 0.5% Silwet L-77. The time interval between initial and subsequent applications was 6 hours.

Seventeen days after the initial application, all plants in the test were examined by a single practiced technician to evaluate percent inhibition. Treatments and corresponding percent inhibitions are given in Table 25.

TABLE 24

| Initial application 93 l/ha | | Glyphosate rate | Subsequent application 93 l/ha | % Inhibition |
|---|---|---|---|---|
| herbicide | accession agent | g a.e./ha | accession agent | CYPES |
| Formulation A | none | 1600 | none | 100 |
| Formulation A | none | 2200 | none | 100 |
| Formulation A | none | 3200 | none | 100 |
| Formulation A | 0.5% L-77 | 1600 | none | 82 |
| Formulation A | 0.5% L-77 | 2200 | none | 96 |
| Formulation A | none | 1600 | 0.5% L-77 at 3 hrs | 78 |
| Formulation A | none | 2200 | 0.5% L-77 at 3 hrs | 97 |
| Formulation B | none | 1600 | none | 94 |
| Formulation B | none | 2200 | none | 100 |
| Formulation B | none | 3200 | none | 98 |
| Formulation B | 0.5% L-77 | 1600 | none | |
| Formulation B | 0.5% L-77 | 2200 | none | 100 |
| Formulation B | none | 1600 | 0.5% L-77 at 3 hrs | 79 |
| Formulation B | none | 2200 | 0.5% L-77 at 3 hrs | 95 |
| Formulation C | none | 1600 | none | 99 |
| Formulation C | none | 2200 | none | 97 |
| Formulation C | none | 3200 | none | 98 |
| Formulation C | 0.5% L-77 | 1600 | none | 82 |
| Formulation C | 0.5% L-77 | 2200 | none | 96 |
| Formulation C | none | 1600 | 0.5% L-77 at 3 hrs | 94 |
| Formulation C | none | 2200 | 0.5% L-77 at 3 hrs | 100 |

TABLE 25

| Initial application 93 l/ha | | Glyphosate rate | Subsequent application 93 l/ha | % Inhibition |
|---|---|---|---|---|
| herbicide | accession agent | g a.e./ha | accession agent | SORHA |
| Formulation A | none | 150 | none | 74 |
| Formulation A | none | 250 | none | 65 |
| Formulation A | none | 400 | none | 91 |
| Formulati6n A | 0.5% L-77 | 150 | none | 0 |
| Formulation A | 0.5% L-77 | 250 | none | 17 |
| Formulation A | none | 150 | 0.5% L-77 at 6 hrs | 46 |
| Formulation A | none | 250 | 0.5% L-77 at 6 hrs | 56 |
| Formulation B | none | 150 | none | 0 |
| Formulation B | none | 250 | none | 25 |
| Formulation B | none | 400 | none | 72 |
| Formulation B | 0.5% L-77 | 150 | none | 0 |
| Formulation B | 0.5% L-77 | 250 | none | 0 |
| Formulation B | none | 150 | 0.5% L-77 at 6 hrs | 19 |
| Formulation B | none | 250 | 0.5% L-77 at 6 hrs | 42 |
| Formulation C | none | 150 | none | 56 |
| Formulation C | none | 250 | none | 85 |
| Formulation C | none | 400 | none | 96 |
| Formulation C | 0.5% L-77 | 150 | none | 5 |
| Formulation C | 0.5% L-77 | 250 | none | 18 |
| Formulation C | none | 150 | 0.5% L-77 at 6 hrs | 33 |
| Formulation C | none | 250 | 0.5% L-77 at 6 hrs | 74 |

In seedling johnsongrass, Silwet L-77 in tank mix was significantly antagonistic (more so for those herbicidal compositions that employ a surfactant coformulant). This antagonism was significantly reduced (and often eliminated) through sequential application of the accession agent.

Example 26

Cutleaf geranium (*Geranium dissectum*, GERDI) plants were grown in pots, maintained in a greenhouse and treated with initial and subsequent applications by procedures exactly as described for Example 1, except where otherwise noted below. Greenhouse temperature was maintained at approximately 21° C. during the day and 16° C. during the night.

Initial applications of Formulations A, B and C, alone or in tank mix with an accession agent, were applied 39 days after planting. Formulations were each applied without accession agent at a range of rates from 300 to 900 g a.e./ha. When an accession agent was included in the treatment, either in tank mix or as a subsequent application, formulations were tested only at 300 and 450 g a.e./ha. This Example includes as accession agent an aqueous solution containing 0.5% Silwet L-77. The time interval between initial and subsequent applications was 4 hours.

Twenty-two days after the initial application, all plants in the test were examined by a single practiced technician to evaluate percent inhibition. Treatments and corresponding percent inhibitions are given in Table 26.

TABLE 26

| Initial application 93 l/ha | | Glyphosate rate | Subsequent application 93 l/ha | % Inhibition |
|---|---|---|---|---|
| herbicide | accession agent | g a.e./ha | accession agent | GERDI |
| Formulation A | none | 300 | none | 49 |
| Formulation A | none | 450 | none | 94 |
| Formulation A | none | 900 | none | 93 |
| Formulation A | 0.5% L-77 | 300 | none | 13 |
| Fonnulation A | 0.5% L-77 | 450 | none | 52 |
| Formulation A | none | 300 | 0.5% L-77 at 4 hrs | 57 |
| Formulation A | none | 450 | 0.5% L-77 at 4 hrs | 67 |
| Formulation B | none | 300 | none | 22 |
| Formulation B | none | 450 | none | 43 |
| Formulation B | none | 900 | none | 70 |
| Formulation B | 0.5% L-77 | 300 | none | 16 |
| Formulation B | 0.5% L-77 | 450 | none | 48 |
| Formulation B | none | 300 | 0.5% L-77 at 4 hrs | 53 |
| Formulation B | none | 450 | 0.5% L-77 at 4 hrs | 59 |
| Formulation C | none | 300 | none | 85 |
| Formulation C | none | 450 | none | 90 |
| Formulation C | none | 900 | none | 95 |
| Formulation C | 0.5% L-77 | 300 | none | 43 |
| Formulation C | 0.5% L-77 | 450 | none | 53 |
| Formulation C | none | 300 | 0.5% L-77 at 4 hrs | 42 |
| Formulation C | none | 450 | 0.5% L-77 at 4 hrs | 60 |

In cutleaf geranium, Silwet L-77 in tank mix was strongly antagonistic for those herbicidal compositions that employ a surfactant coformulant. This antagonism was reduced through sequential application of the accession agent.

Example 27

Indian mustard (*Brassica juncea*, BRSJU) plants were grown in pots, maintained in a greenhouse and treated with initial and subsequent applications by procedures exactly as described for Example 1, except where otherwise noted below. Greenhouse temperature was maintained at approximately 21° C. during the day and 16° C. during the night.

Initial applications of Formulations A, B and C, alone or in tank mix with an accession agent, were applied 26 days after planting. Formulations were each applied without accession agent at a range of rates from 150 to 500 g a.e./ha. When an accession agent was included in the treatment, either in tank mix or as a subsequent application, formulations were tested only at 150 and 250 g a.e./ha. This Example includes as accession agent an aqueous solution containing 0.5% Silwet L-77. The time interval between initial and subsequent applications was 4 hours.

Eighteen days after the initial application, all plants in the test were examined by a single practiced technician to evaluate percent inhibition. Treatments and corresponding percent inhibitions are given in Table 27.

In indian mustard, Silwet L-77 in tank mix was noticeably antagonistic for those herbicidal compositions that employ a surfactant coformulant. This antagonism was reduced through sequential application of the accession agent.

Example 28

Common lambsquarter (*Chenopodium album*, CHEAL) plants were grown in pots, maintained in a greenhouse and treated with initial and subsequent applications by procedures exactly as described for Example 1, except where otherwise noted below. Greenhouse temperature was maintained at approximately 21° C. during the day and 16° C. during the night.

Initial applications of Formulations A, B and C, alone or in tank mix with an accession agent, were applied 33 days after planting. Formulations were each applied without accession agent at a range of rates from 200 to 600 g a.e./ha. When an accession agent was included in the treatment, either in tank mix or as a subsequent application, formulations were tested only at 200 and 400 g a.e./ha. This Example includes as accession agent an aqueous solution containing 0.5% Silwet L-77. The time interval between initial and subsequent applications was 4 hours.

Sixteen days after the initial application, all plants in the test were examined by a single practiced technician to evaluate percent inhibition. Treatments and corresponding percent inhibitions are given in Table 28.

TABLE 27

| Initial application 93 l/ha | | Glyphosate rate | Subsequent application 93 l/ha | % Inhibition |
|---|---|---|---|---|
| herbicide | accession agent | g a.e./ha | accession agent | BRSJU |
| Formulation A | none | 150 | none | 72 |
| Formulation A | none | 250 | none | 68 |
| Formulation A | none | 500 | none | 85 |
| Formulation A | 0.5% L-77 | 150 | none | 30 |
| Formulation A | 0.5% L-77 | 250 | none | 61 |
| Formulation A | none | 150 | 0.5% L-77 at 3 hrs | 43 |
| Formulation A | none | 250 | 0.5% L-77 at 3 hrs | 70 |
| Formulation B | none | 150 | none | 5 |
| Formulation B | none | 250 | none | 35 |
| Formulation B | none | 500 | none | 79 |
| Formulation B | 0.5% L-77 | 150 | none | 22 |
| Formulation B | 0.5% L-77 | 250 | none | 53 |
| Formulation B | none | 150 | 0.5% L-77 at 3 hrs | 42 |
| Formulation B | none | 250 | 0.5% L-77 at 3 hrs | 69 |
| Formulation C | none | 150 | none | 54 |
| Formulation C | none | 250 | none | 78 |
| Formulation C | none | 500 | none | 87 |
| Formulation C | 0.5% L-77 | 150 | none | 26 |
| Formulation C | 0.5% L-77 | 250 | none | 42 |
| Formulation C | none | 150 | 0.5% L-77 at 3 hrs | 59 |
| Formulation C | none | 250 | 0.5% L-77 at 3 hrs | 63 |

TABLE 28

| Initial application 93 l/ha | | Glyphosate rate | Subsequent application 93 l/ha | % Inhibition |
|---|---|---|---|---|
| herbicide | accession agent | g a.e./ha | accession agent | CHEAL |
| Formulation A | none | 200 | none | 52 |
| Formulation A | none | 400 | none | 81 |
| Formulation A | none | 600 | none | 97 |
| Formulation A | 0.5% L-77 | 200 | none | 3 |
| Formulation A | 0.5% L-77 | 400 | none | 7 |
| Formulation A | none | 200 | 0.5% L-77 at 3 hrs | 36 |
| Formulation A | none | 400 | 0.5% L-77 at 3 hrs | 73 |
| Formulation B | none | 200 | none | 2 |
| Formulation B | none | 400 | none | 3 |
| Formulation B | none | 600 | none | 5 |
| Formulation B | 0.5% L-77 | 200 | none. | 0 |
| Formulation B | 0.5% L-77 | 400 | none | 39 |
| Formulation B | none | 200 | 0.5% L-77 at 3 hrs | 11 |
| Formulation B | none | 400 | 0.5% L-77 at 3 hrs | 4 |
| Formulation C | none | 200 | none | 65 |
| Formulation C | none | 400 | none | 95 |
| Formulation C | none | 600 | none | 98 |
| Formulation C | 0.5% L-77 | 200 | none | 2 |
| Formulation C | 0.5% L-77 | 400 | none | 21 |
| Formulation C | none | 200 | 0.5% L-77 at 3 hrs | 63 |
| Formulation C | none | 400 | 0.5% L-77 at 3 hrs | 87 |

In lambsquarter, Silwet L-77 tank mix was significantly antagonistic for those herbicidal compositions that employ a surfactant coformulant. This antagonism was reduced through sequential application of the accession agent.

Example 29

Annual bluegrass (*Poa annua*, POAAN) and redstem filaree (*Erodium cicutarium*, EROCI) plants were grown in pots, maintained in a greenhouse and treated with initial and subsequent applications by procedures exactly as described for Example 1, except where otherwise noted below. Greenhouse temperature was maintained at approximately 21° C. during the day and 16° C. during the night.

Initial applications of Formulations A, B and C, alone or in tank mix with an accession agent, were applied 26 days after planting. Formulations were each applied without accession agent at a range of rates from 300 to 1000 g a.e./ha. When an accession agent was included in the treatment, either in tank mix or as a subsequent application, formulations were tested only at 300 and 600 g a.e./ha. This Example includes as accession agent an aqueous solution containing 0.5% Silwet L-77. The time interval between initial and subsequent applications was 4 hours.

Twenty days after the initial application, all plants in the test were examined by a single practiced technician to evaluate percent inhibition. Treatments and corresponding percent inhibitions are given in Table 29.

TABLE 29

| Initial application 93 l/ha | | Glyphosate rate | Subsequent application 93 l/ha | % Inhibition | |
|---|---|---|---|---|---|
| herbicide | accession agent | g a.e./ha | accession agent | POAAN | EROCI |
| Formulation A | none | 300 | none | 92 | 30 |
| Formulation A | none | 600 | none | 93 | 79 |
| Formulation A | none | 1000 | none | 98 | 93 |
| Formulation A | 0.5% L-77 | 300 | none | 35 | 49 |
| Formulation A | 0.5% L-77 | 600 | none | 77 | 77 |
| Formulation A | none | 300 | 0.5% L-77 at 4 hrs | 88 | 46 |
| Formulation A | none | 600 | 0.5% L-77 at 4 hrs | 93 | 79 |
| Formulation B | none | 300 | none | 57 | 17 |
| Formulation B | none | 600 | none | 78 | 58 |
| Formulation B | none | 1000 | none | 83 | 81 |
| Formulation B | 0.5% L-77 | 300 | none | 27 | 28 |
| Formulation B | 0.5% L-77 | 600 | none | 54 | 60 |
| Formulation B | none | 300 | 0.5% L-77 at 4 hrs | 50 | 15 |
| Formulation B | none | 600 | 0.5% L-77 at 4 hrs | 68 | 77 |
| Formulation C | none | 300 | none | 93 | 68 |
| Formulation C | none | 600 | none | 97 | 95 |
| Formulation C | none | 1000 | none | 98 | 97 |
| Formulation C | 0.5% L-77 | 300 | none | 51 | 29 |
| Formulation C | 0.5% L-77 | 600 | none | 81 | 59 |
| Formulation C | none | 300 | 0.5% L-77 at 4 hrs | 87 | 51 |
| Formulation C | none | 600 | 0.5% L-77 at 4 hrs | 94 | 82 |

In annual bluegrass, Silwet L-77 in tank mix was significantly antagonistic. This antagonism was significantly reduced (and often eliminated) through sequential application of the accession agent. In redstem filaree, Silwet L-77 in tank mix generally enhanced herbicidal effectiveness, and comparable enhancement was observed for sequential application.

Example 30

Velvetleaf (*Abutilon theoplirasti*, ABUTH) and Japanese millet (*Echinochloa crus-galli*, ECHCF) plants were grown in pots, maintained in a greenhouse and treated with initial and subsequent applications by procedures exactly as described for Example 1, except where otherwise noted below.

The experimental design included four replicate pots per treatment. Initial applications of Formulation B, alone or in tank mix with MON-0818 surfactant and/or an accession agent, were applied 14 days after planting velvetleaf and 17 days after planting Japanese millet. MON-0818 was used at a concentration of 0.09% in the spray solution. Formulation B (with and without MON-0818) was applied without accession agent at a range of rates from 100 to 500 g a.e./ha. When an accession agent was included in the treatment, either in tank mix or as a subsequent application, Formulation B was tested only at the lowest rate. This Example includes as accession agents aqueous solutions containing Silwet L-77 at concentrations of 0.5% and 3.0%. Other candidate accession agents tested in this Example include aqueous solutions, at concentrations of 0.5% and 3.0%, of the following surfactants or other substances. In the case of surfactant or other products supplied as diluted products, spray solutions in this and other Examples were prepared to contain 0.5% or 3.0% of the primary ingredient, not on an "as is" basis.

Tergitol TMN-6 of Union Carbide Corporation: described in Union Carbide Product Information, 1989, as 90% ethoxylated 2,6,8-trimethyl-4-nonanol; with an average of 8 moles of ethylene oxide; abbreviated in Tables herein as TMN-6. Tergitol TMN-6 was also employed in mixture with Silwet L-77 at 1:49, 1:19, and 1:9 ratios.

Tween 20 of ICI Surfactants: described in McCutcheon's (loc. cit.) as polyoxyethylene (20) sorbitan monolaurate.

Dimethylsulfoxide: abbreviated herein as DMSO.

The time interval between initial and subsequent applications was 4 hours.

Eighteen days after the initial application, all plants in the test were examined by a single practiced technician to evaluate percent inhibition. Treatments and corresponding percent inhibitions are given in Table 30a (Formulation B applied without MON-0818) and 30b (Formulation B applied with 0.09% MON-0818).

TABLE 30a

| herbicide | Initial application 93 l/ha accession agent | Glyphosate rate g a.e./ha | Subsequent application 93 l/ha accession agent at 4 hrs | % Inhibition ABUTH | ECHCF |
|---|---|---|---|---|---|
| Formulation B | none | 100 | none | 40 | 50 |
| Formulation B | none | 300 | none | 74 | 73 |
| FormulationB | none | 400 | none | 85 | 80 |
| Formulation B | none | 500 | none | 94 | 89 |
| Formulation B | 0.5% L-77 | 100 | none | 89 | 10 |
| Formulation B | 3.0% L-77 | 100 | none | 78 | 10 |
| Formulation B | none | 100 | 0.5% L-77 | 78 | 28 |
| Formulation B | none | 100 | 3.0% L-77 | 70 | 20 |
| Formulation B | 0.5% TMN-6 | 100 | none | 35 | 23 |
| Formulation B | 3.0% TMN-6 | 100 | none | 55 | 15 |
| Formulation B | none | 100 | 0.5% TMN-6 | 30 | 23 |
| Formulation B | none | 100 | 3.0% TMN-6 | 55 | 20 |
| Formulation B | 0.5% Tween 20 | 100 | none | 53 | 53 |
| Formulation B | 3.0% Tween 20 | 100 | none | 75 | 73 |
| Formulation B | none | 100 | 0.5% Tween 20 | 28 | 55 |
| Formulation B | none | 100 | 3.0% Tween 20 | 40 | 40 |
| Formulation B | 0.5% DMSO | 100 | none | 50 | 28 |
| Formulation B | 3.0% DMSO | 100 | none | 48 | 45 |
| Formulation B | none | 100 | 0.5% DMSO | 45 | 33 |
| Formulation B | none | 100 | 3.0% DMSO | 33 | 40 |
| Formulation B | 0.5% TMN-6 + L-77, 1:49 | 100 | none | 88 | 15 |
| Formulation B | 3.0% TMN-6 + L-77, 1:49 | 100 | none | 75 | 15 |
| Formulation B | none | 100 | 0.5% TMN-6 + L-77, 1:49 | 70 | 28 |
| Formulation B | none | 100 | 3.0% TMN-6 + L-77, 1:49 | 50 | 15 |
| Formulation B | 0.5% TMN-6 + L-77, 1:19 | 100 | none | 65 | 10 |
| Formulation B | 3.0% TMN-6 + L-77, 1:19 | 100 | none | 65 | 15 |
| Formulation B | none | 100 | 0.5% TMN-6 + L-77, 1:19 | 73 | 25 |
| Formulation B | none | 100 | 3.0% TMN-6 + L-77, 1:19 | 70 | 35 |
| Formulation B | 0.5% TMN-6 + L-77, 1:9 | 100 | none | 84 | 20 |

TABLE 30a-continued

| Initial application 93 l/ha | | Glyphosate rate g a.e./ha | Subsequent application 93 l/ha | % Inhibition | |
|---|---|---|---|---|---|
| herbicide | accession agent | | accession agent at 4 hrs | ABUTH | ECHCF |
| Formulation B | 3.0% TMN-6 + L-77, 1:9 | 100 | none | 78 | 23 |
| Formulation B | none | 100 | 0.5% TMN-6 + L-77, 1:9 | 75 | 20 |
| Formulation B | none | 100 | 3.0% TMN-6 + L-77, 1:9 | 65 | 35 |

TABLE 30b

| Initial application 93 l/ha | | Glyphosate rate g a.e./ha | Subsequent application 93 l/ha | % Inhibition | |
|---|---|---|---|---|---|
| herbicide | accession agent | | accession agent at 4 hrs | ABUTH | ECHCF |
| Formulation B | none | 100 | none | 68 | 76 |
| Formulation B | none | 300 | none | 95 | 97 |
| Formulation B | none | 400 | none | 98 | 98 |
| Formulation B | none | 500 | none | 99 | 99 |
| Formulation B | 0.5% L-77 | 100 | none | 78 | 15 |
| Formulation B | 3.0% L-77 | 100 | none | 73 | 13 |
| Formulation B | none | 100 | 0.5% L-77 | 65 | 20 |
| Formulation B | none | 100 | 3.0% L-77 | 68 | 18 |
| Formulation B | 0.5% TMN-6 | 100 | none | 33 | 15 |
| Formulation B | 3.0% TMN-6 | 100 | none | 45 | 23 |
| Formulation B | none | 100 | 0.5% TMN-6 | 35 | 30 |
| Formulation B | none | 100 | 3.0% TMN-6 | 30 | 38 |
| Formulation B | 0.5% Tween 20 | 100 | none | 65 | 55 |
| Formulation B | 3.0% Tween 20 | 100 | none | 74 | 75 |
| Formulation B | none | 100 | 0.5% Tween 20 | 50 | 45 |
| Formulation B | none | 100 | 3.0% Tween 20 | 45 | 53 |
| Formulation B | 0.5% DMSO | 100 | none | 45 | 63 |
| Formulation B | 3.0% DMSO | 100 | none | 45 | 60 |
| Formulation B | none | 100 | 0.5% DMSO | 40 | 60 |
| Formulation B | none | 100 | 3.0% DMSO | 35 | 60 |
| Formulation B | 0.5% TMN-6 + L-77, 1:49 | 100 | none | 84 | 15 |
| Formulation B | 3.0% TMN-6 + L-77, 1:49 | 100 | none | 75 | 15 |
| Formulation B | none | 100 | 0.5% TMN-6 + L-77, 1:49 | 63 | 15 |
| Formulation B | none | 100 | 3.0% TMN-6 + L-77, 1:49 | 40 | 13 |
| Formulation B | 0.5% TMN-6 + L-77, 1:19 | 100 | none | 75 | 13 |
| Formulation B | 3.0% TMN-6 + L-77, 1:19 | 100 | none | 75 | 13 |
| Formulation B | none | 100 | 0.5% TMN-6 + L-77, 1:19 | 68 | 20 |
| Formulation B | none | 100 | 3.0% TMN-6 + L-77, 1:19 | 65 | 35 |
| Formulation B | 0.5% TMN-6 + L-77, 1:9 | 100 | none | 86 | 20 |
| Formulation B | 3.0% TMN-6 + L-77, 1:9 | 100 | none | 73 | 25 |
| Formulation F | none | 100 | 0.5% TMN-6 + L-77, 1:9 | 75 | 30 |
| Formulation F | none | 100 | 3.0% TMN-6 + L-77, 1:9 | 68 | 35 |

Example 31

The procedures of Example 30 were repeated exactly except percent inhibition was determined nineteen days after initial application, and the candidate accession agents in addition to Silwet L-77 were:

Tergitol TMN-10 of Union Carbide Corporation: described in Union Carbide Product Information, 1989 as 90% ethoxylated 2,6,8-trimethyl-4-nonanol; with an average of 11 moles of ethylene oxide; abbreviated in Tables herein as TMN-10. Tergitol TMN-10 was also employed with Silwet L-77 at ratios of 1:49, 1:19, and 1:9.

Light mineral oil obtained from Fisher Scientific: abbreviated in Tables herein as "min oil."

R-Way Crop Oil Concentrate described on its label as containing 83% petroleum oil and 17% surfactant blend; abbreviated in Tables herein as COC.

The light mineral oil contains no surfactants for emulsification in the spray solution; a mixture was prepared by agitation and applied immediately before the oil separated significantly from the water.

Treatments and corresponding percent inhibitions are given in Table 31 a (Formulation B applied without MON-0818) and 31b (Formulation B applied with 0.09% MON-0818).

TABLE 31a

| Initial application 93 l/ha, no MON-0818 | | Glyphosate | Subsequent application 93 l/ha | % Inhibition | |
|---|---|---|---|---|---|
| herbicide | accession agent | rate g a.e./ha | accession agent | ABUTH | ECHCF |
| | | | at 4 hrs | | |
| Formulation B | none | 100 | none | 43 | 60 |
| Formulation B | none | 300 | none | 90 | 94 |
| Formulation B | none | 400 | none | 91 | 95 |
| Formulation B | none | 500 | none | 98 | 98 |
| Formulation B | 0.5% L-77 | 100 | none | 90 | 25 |
| Formulation B | 3.0% L-77 | 100 | none | 73 | 23 |
| Formulation B | none | 100 | 0.5% L-77 | 81 | 53 |
| Formulation B | none | 100 | 3.0% L-77 | 70 | 38 |
| Formulation B | 0.5% TMN-10 | 100 | none | 70 | 50 |
| Formulation B | 3.0% TMN-10 | 100 | none | 48 | 40 |
| Formulation B | none | 100 | 0.5% TMN-10 | 71 | 35 |
| Formulation B | none | 100 | 3.0% TMN-10 | 45 | 40 |
| Formulation B | 0.5% min oil | 100 | none | 84 | 63 |
| Formulation B | 3.0% min oil | 100 | none | 81 | 76 |
| Formulation B | none | 100 | 0.5% min oil | 70 | 38 |
| Formulation B | none | 100 | 3.0% min oil | 53 | 50 |
| Formulation B | 0.5% COC | 100 | none | 63 | 25 |
| Formulation B | 3.0% COC | 100 | none | 60 | 23 |
| Formulation B | none | 100 | 0.5% COC | 68 | 38 |
| Formulation B | none | 100 | 3.0% COC | 58 | 40 |
| Formulation B | 0.5% TMN-10 + L-77, 1:49 | 100 | none | 89 | 13 |
| Formulation B | 3.0% TMN-10 + L-77, 1:49 | 100 | none | 76 | 23 |
| Formulation B | none | 100 | 0.5%TMN-10 + L-77, 1:49 | 78 | 25 |
| Formulation B | none | 100 | 3.0%TMN-10 + L-77, 1:49 | 70 | 38 |
| Formulation B | 0.5% TMN-10 + L-77,1:19 | 100 | none | 85 | 20 |
| Formulation B | 3.0% TMN-10 + L-77,1:19 | 100 | none | 80 | 15 |
| Formulation B | none | 100 | 0.5% TMN-10 + L-77, 1:19 | 80 | 43 |
| Formulation B | none | 100 | 3.0%TMN-10+ L-77, 1:19 | 74 | 33 |
| Formulation B | 0.5% TMN-10 + L-77, 1:9 | 100 | none | 78 | 23 |
| Formulation B | 3.0% TMN-10 + L-77, 1:9 | 100 | none | 60 | 23 |
| Formulation B | none | 100 | 0.5% TMN-10 + L-77, 1:9 | 75 | 40 |
| Formulation B | none | 100 | 3.0% TMN-10 + L-77, 1:9 | 74 | 33 |

TABLE 31b

| Initial application 93 l/ha, 0.09% MON-0818 | | Glyphosate | Subsequent application 93 l/ha | % Inhibition | |
|---|---|---|---|---|---|
| herbicide | accession agent | rate g a.e./ha | accession agent | ABUTH | ECHCF |
| | | | at 4 hrs | | |
| Formulation B | none | 100 | none | 81 | 81 |
| Formulation B | none | 300 | none | 86 | 96 |
| Formulation B | none | 400 | none | 99 | 98 |
| Formulation B | none | 500 | none | 99 | 97 |
| Formulation B | 0.5% L-77 | 100 | none | 90 | 25 |
| Formulation B | 3.0% L-77 | 100 | none | 76 | 25 |

TABLE 31b-continued

| Initial application 93 l/ha, 0.09% MON-0818 | | Glyphosate | Subsequent application 93 l/ha | % Inhibition | |
|---|---|---|---|---|---|
| herbicide | accession agent | rate g a.e./ha | accession agent at 4 hrs | ABUTH | ECHCF |
| Formulation B | none | 100 | 0.5% L-77 | 79 | 50 |
| Formulation B | none | 100 | 3.0% L-77 | 70 | 45 |
| Formulation B | 0.5% TMN-10 | 100 | none | 70 | 75 |
| Formulation B | 3.0% TMN-10 | 100 | none | 74 | 33 |
| Formulation B | none | 100 | 0.5% TMN-10 | 73 | 60 |
| Formulation B | none | 100 | 3.0% TMN-10 | 55 | 50 |
| Formulation B | 0.5% min oil | 100 | none | 70 | 63 |
| Formulation B | 3.0% min oil | 100 | none | 69 | 56 |
| Formulation B | none | 100 | 0.5% min oil | 91 | 89 |
| Formulation B | none | 100 | 3.0% min oil | 68 | 64 |
| Formulation B | 0.5% COC | 100 | none | 69 | 48 |
| Formulation B | 3.0% COC | 100 | none | 68 | 50 |
| Formulation B | none | 100 | 0.5% COC | 71 | 55 |
| Formulation B | none | 100 | 3.0% COC | 75 | 60 |
| Formulation B | 0.5% TMN-10 + L-77, 1:49 | 100 | none | 89 | 23 |
| Formulation B | 3.0% TMN-10 +-0 L-77, 1:49 | 100 | none | 76 | 10 |
| Formulation B | none | 100 | 0.5% TMN-10 + L-77, 1:49 | 78 | 30 |
| Formulation B | none | 100 | 3.0% TMN-10 + L-77, 1:49 | 74 | 25 |
| Formulation B | 0.5% TMN-10 + L-77, 1:19 | 100 | none | 79 | 20 |
| Formulation B | 3.0% TMN-10 + L-77, 1:19 | 100 | none | 75 | 18 |
| Formulation B | none | 100 | 0.5% TMN-10 + L-77, 1:19 | 81 | 40 |
| Formulation B | none | 100 | 3.0% TMN-10 + L-77,1:19 | 75 | 43 |
| Formulation B | 0.5% TMN-10 + L-77, 1:9 | 100 | none | 68 | 30 |
| Formulation B | 3.0% TMN-10 + L-77, 1:9 | 100 | none | 79 | 20 |
| Formulation B | none | 100 | 0.5% TMN-10 + L-77, 1:9 | 78 | 40 |
| Formulation B | none | 100 | 3.0% TMN-10 + L-77, 1:9 | 76 | 53 |

Example 32

The procedures of Example 30 were repeated exactly except that initial applications were made 17 days after planting velvetleaf and 20 days after planting Japanese millet, percent inhibition was determined sixteen days after initial application, and the candidate accession agents in addition to Silwet L-77 were:

Ethoduomeen T/13 and Ethoduomeen T/25 of Akzo Chemicals Inc.: described in Akzo's brochure titled "Ethoxylated and propoxylated surfactants" published 1991 as ethoxylated N-tallowalkyl-1,3-diaminopropanes having respectively 3 and 15 moles EO; the Ethoduomeen trademark is abbreviated in tables herein as "Edm".

Ethylan CPG945 of Akcros Chemicals: described in McCutcheon's (loc. cit.) as a modified alcohol ethoxylate; abbreviated in tables herein by omission of the Ethylan trademark.

Neodol 25-3 and Neodol 25-9 of Shell Chemical Company: described in McCutcheon's (loc. cit.) as $C_{12-15}$ primary alcohol ethoxylate having respectively 3 and 9 moles EO; the Neodol trademark is abbreviated herein as "Neo".

SAG-47: a widely used silicone antifoam of Witco Corporation, OSi Specialties Group.

Treatments and corresponding percent inhibitions are given in Table 32a (Formulation B applied without MON-0818) and 32b (Formulation B applied with 0.09% MON-0818).

TABLE 32a

| Initial application 93 l/ha, no MON-0818 | | Glyphosate | Subsequent application 93 l/ha | % Inhibition | |
|---|---|---|---|---|---|
| herbicide | accession agent | rate g a.e./ha | accession agent at 4 hrs | ABUTH | ECHCF |
| Formulation B | none | 100 | none | 20 | 88 |
| Formulation B | none | 300 | none | 50 | 98 |

TABLE 32a-continued

| herbicide | Initial application 93 l/ha, no MON-0818 accession agent | Glyphosate rate g a.e./ha | Subsequent application 93 l/ha accession agent at 4 hrs | % Inhibition ABUTH | ECHCF |
|---|---|---|---|---|---|
| Formulation B | none | 400 | none | 78 | 97 |
| Formulation B | none | 500 | none | 88 | 99 |
| Formulation B | 0.5% L-77 | 100 | none | 40 | 5 |
| Formulation B | 3.0% L-77 | 100 | none | 45 | 38 |
| Formulation B | none | 100 | 0.5% L-77 | 45 | 30 |
| Formulation B | none | 100 | 3.0% L-77 | 43 | 13 |
| Formulation B | 0.5% Edm T/13 | 100 | none | 43 | 91 |
| Formulation B | 3.0% Edm T/13 | 100 | none | 73 | 85 |
| Formulation B | none | 100 | 0.5% Edm T/13 | 15 | 60 |
| Formulation B | none | 100 | 3.0% Edm T/13 | 43 | 55 |
| Formulation B | 0.5% Edm T/25 | 100 | none | 38 | 88 |
| Formulation B | 3.0% Edm T/25 | 100 | none | 74 | 91 |
| Formulation B | none | 100 | 0.5% Edm T/25 | 30 | 38 |
| Formulation B | none | 100 | 3.0% Edm T/25 | 35 | 20 |
| Formulation B | 0.5% CPG 945 | 100 | none | 35 | 74 |
| Formulation B | 3.0% CPG 945 | 100 | none | 40 | 71 |
| Formulation B | none | 100 | 0.5% CPG94S | 30 | 35 |
| Formulation B | none | 100 | 3.0% CPG94S | 33 | 35 |
| Formulation B | 0.5% Neo 25-3 | 100 | none | 33 | 20 |
| Formulation B | 3.0% Neo 25-3 | 100 | none | 35 | 20 |
| Formulation B | none | 100 | 0.5% Neo 25-3 | 10 | 5 |
| Formulation B | none | 100 | 3.0% Neo 25-3 | 5 | 0 |
| Formulation B | 0.5% Neo 25-9 | 100 | none | 10 | 10 |
| Formulation B | 3.0% Neo 25-9 | 100 | none | 30 | 10 |
| Formulation B | none | 100 | 0.5% Neo 25-9 | 28 | 30 |
| Formulation B | none | 100 | 3.0% Neo 25-9 | 23 | 33 |
| Formulation B | 0.5% SAG 47 | 100 | none | 23 | 38 |
| Formulation B | 3.0% SAG 47 | 100 | none | 18 | 30 |
| Formulation B | none | 100 | 0.5% SAG 47 | 15 | 25 |
| Formulation B | none | 100 | 3.0% SAG 47 | 20 | 25 |

TABLE 32b

| herbicide | Initial application 93 l/ha, 0.09% MON-0818 accession agent | Glyphosate rate g a.e./ha | Subsequent application 93 l/ha accession agent at 4 hrs | % Inhibition ABUTH | ECHCF |
|---|---|---|---|---|---|
| Formulation B | none | 100 | none | 18 | 86 |
| Formulation B | none | 300 | none | 84 | 99 |
| Formulation B | none | 400 | none | 95 | 99 |
| Formulation B | none | 500 | none | 95 | 99 |
| Formulation B | 0.5% L-77 | 100 | none | 45 | 28 |
| Formulation B | 3.0% L-77 | 100 | none | 50 | 18 |
| Formulation B | none | 100 | 0.5% L-77 | 43 | 74 |
| Formulation B | none | 100 | 3.0% L-77 | 40 | 48 |
| Formulation B | 0.5% Edm T/13 | 100 | none | 30 | 89 |
| Formulation B | 3.0% Edm T/13 | 100 | none | 75 | 96 |
| Formulation B | none | 1oo | 0.5%EdmT/13 | 25 | 33 |
| Formulation B | none | 1O() | 3.0% Edm T/13 | 43 | 98 |
| Formulation B | 0.5% Edm T/25 | 100 | none | 63 | 95 |
| Formulation B | 3.0% Edm T/25 | 100 | none | 75 | 95 |
| Formulation B | none | 100 | 0.5% Edm T/25 | 33 | 94 |
| Formulation B | none | 100 | 3.0% Edm T/25 | 70 | 83 |
| Formulation B | 0.5% CPG945 | 100 | none | 33 | 73 |
| Formulation B | 3.0% CPG945 | 100 | none | 53 | 75 |
| Formulation B | none | 100 | 0.5% CPG 945 | 55 | 88 |
| Formulation B | none | 100 | 3.0% CPG 945 | 45 | 86 |
| Formulation B | 0.5% Neo 25-3 | 100 | none | 63 | 53 |
| Formulation B | 3.0%Neo2S-3 | 100 | none | 55 | 35 |
| Formulation B | none | 1oo | 0.5% Neo25-3 | 35 | 35 |
| Formulation B | none | 100 | 3.0% Neo 25-3 | 33 | 20 |
| Formulation B | 0.5% Neo 25-9 | 100 | none | 28 | 20 |
| Formulation B | 3.0% Neo 25-9 | 100 | none | 35 | 10 |
| Formulation B | none | 100 | 0.5% Neo 25-9 | 8 | 10 |
| Formulation B | none | 100 | 3.0% Neo 25-9 | 25 | 46 |
| Formulation B | 0.5% SAG 47 | 100 | none | 45 | 97 |

TABLE 32b-continued

| Initial application 93 l/ha, 0.09% MON-0818 | | Glyphosate | Subsequent application 93 l/ha | % Inhibition | |
|---|---|---|---|---|---|
| herbicide | accession agent | rate g a.e./ha | accession agent at 4 hrs | ABUTH | ECHCF |
| Formulation B | 3.0% SAG47 | 100 | none | 48 | 85 |
| Formulation B | none | 100 | 0.5% SAG 47 | 50 | 89 |
| Formulation B | none | 100 | 3.0% SAG 47 | 45 | 79 |

Example 33

The procedures of Example 30 were repeated exactly except that initial applications were made 15 days after planting velvetleaf and 18 days after planting Japanese millet, percent inhibition was determined seventeen days after initial application, and the candidate accession agent in addition to Silwet L-77 was:

Nonanol (2EO) ethoxylate, supplied by Shell Chemical Company abbreviated in tables herein as "nonanol 2". Nonanol (2EO) ethoxylate was also employed in admixture with Silwet L-77 in ratios of 2:1, 1:2, 1:1, 1:9, and 9:1.

Treatments and corresponding percent inhibitions are given in Table 33a (Formulation B applied without MON-0818) and 33b (Formulation B applied with 0.09% MON-0818).

TABLE 33a

| Initial application 93 l/ha, no MON-0818 | | Glyphosate | Subsequent application 93 l/ha | % Inhibition | |
|---|---|---|---|---|---|
| herbicide | accession agent | rate g a.e./ha | accession agent at 4 hrs | ABUTH | ECHCF |
| Formulation B | none | 100 | none | 40 | 40 |
| Formulation B | none | 300 | none | 85 | 73 |
| Formulation B | none | 400 | none | 99 | 95 |
| Formulation B | none | 500 | none | 100 | 94 |
| Formulation B | 0.5% L-77 | 100 | none | 85 | 20 |
| Formulation B | 3.0% L-77 | 100 | none | 68 | 38 |
| Formulation B | none | 100 | 0.5% L-77 | 93 | 51 |
| Formulation B | none | 100 | 3.0% L-77 | 65 | 33 |
| Formulation B | 0.5% nonanol 2 | 100 | none | 24 | 20 |
| Formulation B | 3.0% nonanol 2 | 100 | none | 38 | 25 |
| Formulation B | none | 100 | 0.5% nonanol 2 | 53 | 64 |
| Formulation B | none | 100 | 3.0% nonanol 2 | 38 | 43 |
| Formulation B | 0.5% nonanol 2 + L-77, 2:1 | 100 | none | 68 | 20 |
| Formulation B | 3.0% nonanol 2 + L-77, 2:1 | 100 | none | 80 | 20 |
| Formulation B | none | 100 | 0.5% nonanol 2 + L-77, 2:1 | 53 | 64 |
| Formulation B | none | 100 | 3.0% nonanol 2 + L-77, 2:1 | 50 | 65 |
| Formulation B | 0.5% nonanol 2 + L-77, 1:2 | 100 | none | 85 | 30 |
| Formulation B | 3.0% nonanol 2 + L-77,1:2 | 100 | none | 78 | 48 |
| Formulation B | none | 100 | 0.5% nonanol 2 + L-77, 1:2 | 75 | 78 |
| Formulation B | none | 100 | 3.0% nonanol 2 + L-77, 1:2 | 63 | 48 |
| Formulation B | 0.5% nonanol 2 + L-77, {1 | 100 | none | 53 | 25 |
| Formulation B | 3.0% nonanol 2 | 100 | none | 70 | 23 |
| Formulation B | none | 100 | 0.5% nonanol 2 + L-77, 1:1 | 65 | 55 |
| Formulation B | none | 100 | 3.0% nonanol 2 + L-77,1:1 | 45 | 33 |
| Formulation B | 0.5% nonanol 2 + L-77,1:9 | 100 | none | 91 | 20 |
| Formulation B | 3.0% nonanol 2 + L-77, 1:9 | 100 | none | 78 | 38 |
| Forrnulation B | none L-77,1:9 | 100 | 0.5% nonanol 2 + | 68 | 48 |

TABLE 33a-continued

| herbicide | Initial application 93 l/ha, no MON-0818 accession agent | Glyphosate rate g a.e./ha | Subsequent application 93 l/ha accession agent at 4 hrs | % Inhibition ABUTH | ECHCF |
|---|---|---|---|---|---|
| Formulation B | none | 100 | 3.0% nonanol 2 + L-77, 1:9 | 65 | 38 |
| Formulation B | 0.5% nonanol 2 + L-77, 9:1 | 100 | none | 40 | 33 |
| Formulation B | 3.0% nonanol 2 +L-77, 9:1 | 100 | none | 48 | 20 |
| Formulation B | none | 100 | 0.5% nonanol 2 + L-77, 9:1 | 40 | 40 |
| Formulation B | none | 100 | 3.0% nonanol 2 + L-77, 9:1 | 35 | 33 |

TABLE 33b

| herbicide | Initial application 93 l/ha, 0.09% MON-0818 accession agent | Glyphosate rate g a.e./ha | Subsequent application 93 l/ha accession agent at 4 hrs | % Inhibition ABUTH | ECHCF |
|---|---|---|---|---|---|
| Formulation B | none | 100 | none | 73 | 97 |
| Formulation B | none | 300 | none | 99 | 98 |
| Formulation B | none | 400 | none | 97 | 100 |
| Formulation B | none | 500 | none | 100' | 100 |
| Formulation B | 0.5% L-77 | 100 | none | 89 | 30 |
| Formulation B | 3.0% L-77 | 100 | none | 68 | 40 |
| Formulation B | none | 100 | 0.5% L-77 | 73 | 81 |
| Formulation B | none | 100 | 3.0% L-77 | 60 | 75 |
| Formulation B | 0.5% nonanol 2 | 100 | none | 20 | 15 |
| Formulation B | 3.0% nonanol 2 | 100 | none | 45 | 15 |
| Formulation B | none | 100 | 0.5% nonanol 2 | 50 | 97 |
| Formulation B | none | 100 | 3.0% nonanol 2 | 45 | 81 |
| Formulation B | 0.5% nonanol 2 + L-77,2:1 | 100 | none | 40 | 20 |
| Formulation B | 3.0% nonanol 2 + L-77, 2:1 | 100 | none | 75 | 25 |
| Formulation B | none | 100 | 0.5% nonanol 2 + L-77,2:1 | 50 | 95 |
| Formulation B | none | 100 | 3.0% nonanol 2 + L-77,2:1 | 70 | 86 |
| Formulation B | 0.5% nonanol 2 + L-77, 1:2 | 100 | none | 83 | 38 |
| Formulation B | 3.0% nonanol 2 + L-77, 1:2 | 100 | none | 80 | 58 |
| Formulation B | none | 100 | 0.5% nonanol 2 + L-77, 1:2 | 73 | 89 |
| Formulation B | none | 100 | 3.0% nonanol 2 + L-77, 1:2 | 68 | 85 |
| Formulation B | 0.5% nonanol 2 + L-77, 1:1 | 100 | none | 7& | 38 |
| Formulation B | 3.0% nonanol 2 + L-77, 1:1 | 100 | none | 75 | 53 |
| Formulation B | none | 100 | 0.5% nonanol 2 + L-77, 1:1 | 65 | 95 |
| Formulation B | none | 100 | 3.0% nonanol 2 + L-77, 1:1 | 65 | 85 |
| Formulation B | 0.5% nonanol 2 + L-77, 1:9 | 100 | none | 87 | 20 |
| Formulation B | 3.0% nonanol 2 + L-77, 1:9 | 100 | none | 75 | 45 |
| Formulation B | none | 100 | 0.5% nonanol 2 + L-77, 1:9 | 73 | 94 |
| Formulation B | none | 100 | 3.0% nonanol 2 + L-77, 1:9 | 68 | 76 |
| Formulation B | 0.5% nonanol 2 + L-77, 9:1 | 100 | none | 60 | 33 |
| Formulation B | 3.0% nonanol 2 + L-77,9:1 | 100 | none | 48 | 23 |
| Formulation B | none | 100 | 0.5% nonanol 2 + | 55 | 88 |

TABLE 33b-continued

| Initial application 93 l/ha, 0.09% MON-0818 | | Glyphosate | Subsequent application 93 l/ha | % Inhibition | |
|---|---|---|---|---|---|
| herbicide | accession agent | rate g a.e./ha | accession agent at 4 hrs | ABUTH | ECHCF |
| Formulation B | none | 100 | 3.0% nonanol 2 + L-77, 9:1 | 38 | 80 |

Example 34

The procedures of Example 30 were repeated exactly except that initial applications were made 14 days after planting velvetleaf and 17 days after planting Japanese millet, percent inhibition was determined seventeen days after initial application, and the candidate accession agent in addition to Silwet L-77 was:

Nonanol (4EO) ethoxylate, supplied by Shell Chemical company abbreviated in tables herein as "nonanol 4". Nonanol (4EO) ethoxylate was also employed in admixture with Silwet L-77 in ratios of 2:1, 1:2, 1:1, 9:1, and 1:9.

TABLE 34a

| Initial application 93 l/ha, no MON-0818 | | Glyphosate | Subsequent application 93 l/ha | % Inhibition | |
|---|---|---|---|---|---|
| herbicide | accession agent | rate g a.e./ha | accession agent at 4 hrs | ABUTH | ECHCF |
| Formulation B | none | 100 | none | 65 | 45 |
| Formulation B | none | 300 | none | 85 | 90 |
| Formulation B | none | 400 | none | 93 | 91 |
| Formulation B | none | 500 | none | 96 | 99 |
| Formulation B | 0.5% L-77 | 100 | none | 80 | 23 |
| Formulation B | 3.0% L-77 | 100 | none | 75 | 23 |
| Formulation B | none | 100 | 0.5% L-77 | 73 | 55 |
| Formulation B | none | 100 | 3.0% L-77 | 74 | 45 |
| Formulation B | 0.5% nonanol 4 | 100 | none | 43 | 25 |
| Formulation B | 3.0% nonanol 4 | 100 | none | 68 | 43 |
| Formulation B | none | 100 | 0.5% nonanol 4 | 45 | 45 |
| Formulation B | none | 100 | 3.0% nonanol 4 | 45 | 48 |
| Formulation B | 0.5% nonanol 4 + L-77, 2:1 | 100 | none | 70 | 30 |
| Formulation B | 3.0% nonanol4 + L-77, 2:1 | 100 | none | 84 | 38 |
| Formulation B | none | 100 | 0.5% nonanol 4 + L-77, 2:1 | 53 | 53 |
| Eormulation B | none | 100 | 3.0% nonanol 4 + L-77, 2:1 | 74 | 53 |
| Formulation B | 0.5% nonanol 4 + L-77, 1:2 | 100 | none | 79 | 30 |
| Formulation B | 3.0% nonanol 4 + L-77,1:2 | 100 | none | 80 | 48 |
| Formulation B | none | 100 | 0.5% nonanol 4 + L-77, 1:2 | 85 | 50 |
| Formulation B | none | 100 | 3.0% nonanol 4 + L-77, 1:2 | 79 | 53 |
| Formulation B | 0.5% nonanol 4 + L-77, 1:1 | 100 | none | 78 | 30 |
| Formulation B | 3.0% nonanol 4 + L-77,1:1 | 100 | none | 84 | 50 |
| Formulation B | none | 100 | 0.5% nonanol 4 + L-77, 1:1 | 80 | 48 |
| Formulation B | none | 100 | 3.0% nonanol 4 + L-77, 1:1 | 71 | 48 |
| Formulation B | 0.5% nonanol 4 + L-77, 1:9 | 100 | none | 84 | 40 |
| Formulation B | 3.0% nonanol 4 + L-77,1:9 | 100 | none | 76 | 45. |
| Formulation B | none | 100 | 0.5% nonanol 4 + L-77, 1:9 | 80 | 48 |
| Formulation B | none | 100 | 3.0% nonanol 4 + L-77, 1:9 | 71 | 43 |
| Formulation B | 0.5% nonanol 4 + L-77,9:1 | 100 | none | 28 | 23 |
| Formulation B | 3.0% nonanol 4 + L-77, 9:1 | 100 | none | 65 | 10 |

TABLE 34a-continued

| | Initial application 93 l/ha, no MON-0818 | Glyphosate | Subsequent application 93 l/ha | % Inhibition | |
|---|---|---|---|---|---|
| herbicide | accession agent | rate g a.e./ha | accession agent at 4 hrs | ABUTH | ECHCF |
| Formulation B | none | 100 | 0.5% nonanol 4 + L-77, 9:1 | 55 | 38 |
| Formulation B | none | 100 | 3.0% nonanol 4 + L-77, 9:1 | 35 | 30 |

TABLE 34b

| | Initial application 93 l/ha, 0.09% MON-0818 | Glyphosate | Subsequent application 93 l/ha | % Inhibition | |
|---|---|---|---|---|---|
| herbicide | accession agent | rate g a.e./ha | accession agent at 4 hrs | ABUTH | ECHCF |
| Formulation B | none | 100 | none | 78 | 88 |
| Formulation B | none | 300 | none | 93 | 100 |
| Formulation B | none | 400 | none | 96 | 100 |
| Formulation B | none | 500 | none | 97 | 100 |
| Formulation B | 0.5% L-77 | 100 | none | 70 | 30 |
| Formulation B | 3.0% L-77 | 100 | none | 76 | 35 |
| Formulation B | none | 100 | 0.5% L-77 | 89 | 55 |
| Formulation B | none | 100 | 3.0% L-77 | 70 | 65 |
| Formulation B | 0.5% nonanol 4 | 100 | none | 75 | 48 |
| Formulation B | 3.0% nonanol 4 | 100 | none | 65 | 18 |
| Formulation B | none | 100 | 0.5% nonanol 4 | 45 | 63 |
| Formulation B | none | 100 | 3.0% nonanol 4 | 45 | 83 |
| Formulation B | 0.5% nonanol 4 + L-77,2:1 | 100 | none | 68 | 30 |
| Formulation B | 3.0% nonanol 4 + L-77,2:1 | 100 | none | 91 | 40 |
| Formulation B | none | 100 | 0.5% nonanol 4 + L-77, 2:1 | 71 | 83 |
| Formulation B | none | 100 | 3.0% nonanol 4 + L-77,2:1 | 73 | 85 |
| Formulation B | 0.5% nonanol 4 + L-77, 1:2 | 100 | none | 79 | 38 |
| Formulation B | 3.0% nonanol 4 + L-77, 1:2 | 100 | none | 80 | 55 |
| Formulation B | none | 100 | 0.5% nonanol 4 + L-77, 1:2 | 78 | 74 |
| Formulation B | none | 100 | 3.0% nonanol 4 + L-77, 1:2 | 78 | 78 |
| Formulation B | 0.5% nonanol 4 + L-77, 1:1 | 100 | none | 77 | 43 |
| Formulation B | 3.0% nonanol 4 + L-77, 1:1 | 100 | none | 88 | 48 |
| Formulation B | none | 100 | 0.5% nonanol 4 + L-77, 1:1 | 80 | 55 |
| Formulation B | none | 100 | 3.0% nonanol 4 + L-77, 1:1 | 70 | 70 |
| Formulation B | 0.5% nonanol 4 + L-77, 1:9 | 100 | none | 85 | 40 |
| Formulation B | 3.0% nonanol 4 + L-77, 1:9 | 100 | none | 76 | 40 |
| Formulation B | none | 100 | 0.5% nonanol 4 + L-77, 1:9 | 80 | 60 |
| Formulation B | none | 100 | 3.0% nonanol 4 + L-77, 1:9 | 75 | 68 |
| Formulation B | 0.5% nonanol 4 + L-77,9:1 | 100 | none | 25 | 38 |
| Formulation B | 3.0% nonanol 4 + L-77, 9:1 | 100 | none | 65 | 23 |
| Formulation B | none | 100 | 0.5% nonanol 4 + L-77, 9:1 | 43 | 58 |
| Formulation B | none | 100 | 3.0% nonanol 4 + L-77, 9:1 | 50 | 53 |

Example 35

The procedures of Example 30 were repeated exactly except that initial applications were made 17 days after planting velvetleaf and 20 days after planting Japanese millet, percent inhibition was determined seventeen days after initial application, and the candidate accession agent in addition to Silwet L-77 was:

Neodol 1-5 of Shell Chemical Company: described in McCutcheon's (loc. cit.) as $C_{11}$ primary alcohol ethoxylate having 5 moles EO. Neodol 1-5 (labelled Neo 1-5) was also employed in admixture with Silwet L-77 in ratios of 2:1, 1:2, 1:1, 9:1, and 1:9.

Treatments and corresponding percent inhibitions are given in Table 35a (Formulation B applied without MON-0818) and 35b (Formulation B applied with MON-0818).

TABLE 35a

| | Initial application 93 l/ha, no MON-0818 | Glyphosate rate | Subsequent application 93 l/ha | % Inhibition | |
|---|---|---|---|---|---|
| herbicide | accession agent | g a.e./ha | accession agent at 4 hrs | ABUTH | ECHCF |
| Formulation B | none | 100 | none | 10 | 30 |
| Formulation B | none | 300 | none | 40 | 55 |
| Formulation B | none | 400 | none | 80 | 53 |
| Formulation B | none | 500 | none | 80 | 68 |
| Formulation B | 0.5% L-77 | 100 | none | 84 | 35 |
| Formulation B | 3.0% L-77 | 100 | none | 55 | 40 |
| Formulation B | none | 100 | 0.5% L-77 | 55 | 45 |
| Formulation B | none | 100 | 3.0% L-77 | 33 | 40 |
| Formulation B | 0.5% Neo 1-5 | 100 | none | 40 | 35 |
| Formulation B | 3.0% Neo 1-5 | 100 | none | 35 | 28 |
| Formulation B | none | 100 | 0.5% Neo 1-5 | 40 | 55 |
| Formulation B | none | 100 | 3.0% Neo 1-5 | 30 | 38 |
| Formulation B | 0.5% Neo 1-5 + L-77, 2:1 | 100 | none | 35 | 30 |
| Formulation B | 3.0% Neo 1-5 + L-77, 2:1 | 100 | none | 60 | 15 |
| Formulation B | none | 100 | 0.5% Neo 1-5 + L-77, 2:1 | 40 | 50 |
| Formulation B | none | 100 | 3.0% Neo 1-5 + L-77, 2:1 | 30 | 38 |
| Formulation B | 0.5% Neo 1-5 + L-77, 1:2 | 100 | none | 55 | 33 |
| Formulation B | 3.0% Neo 1-5 + L-77, 1:2 | 100 | none | 68 | 33 |
| Formulation B | none | 100 | 0.5% Neo 1-5 + L-77, 1:2 | 65 | 50 |
| Formulation B | none | 100 | 3.0% Neo 1-5 + L-77, 1:2 | 55 | 45 |
| Formulation B | 0.5% Neo 1-5 + L-77, 1:1 | 100 | none | 65 | 40 |
| Formulation B | 3.0% Neo 1-5 + L-77, 1:1 | 100 | none | 75 | 25 |
| Formulation B | none | 100 | 0.5% Neo 1-5 + L-77, 1:1 | 48 | 50 |
| Formulation B | none | 100 | 3.0% Neo 1-5 + | 50 | 35 |
| Formulation B | 0.5% Neo 1-5 + L-77, 1:9 | 100 | none | 68 | 33 |
| Formulation B | 3.0% Neo 1-5 + L-77, 1:9 | 100 | none | 65 | 45 |
| Formulation B | none | 100 | 0.5% Neo 1-5 + L-77, 1:9 | 38 | 45 |
| Formulation B | none | 1oo | 3.0%Neo 1-5.+ L-77, 1:9 | 58 | 38 |
| Formulation B | 0.5% Neo 1-5 + L-77, 9:1 | 100 | none | 43 | 35 |
| Formulation B | 3.0% Neo 1-5 + L-77, 9:1 | 100 | none | 43 | 25 |
| Formulation B | none | 100 | 0.5% Neo 1-5 + L-77,9:1 | 30 | 38 |
| Formulation B | none | 100 | 3.0% Neo 1-5+ L-77, 9:1 | 28 | 28 |

TABLE 35b

| Initial application 93 1/ha, 0.09% MON-0818 | | Glyphosate | Subsequent application 93 l/ha | % Inhibition | |
|---|---|---|---|---|---|
| herbicide | accession agent | rate g a.e./ha | accession agent at 4 hrs | ABUTH | ECHCF |
| Formulation B | none | 100 | none | 48 | 70 |
| Formulation B | none | 300 | none | 75 | 97 |
| Formulation B | none | 400 | none | 96 | 95 |
| Formulation B | none | 500 | none | 97 | 99 |
| Formulation B | 0.5% L-77 | 100 | none | 58 | 50 |
| Formulation B | 3.0% L-77 | 100 | none | 63 | 40 |
| Formulation B | none | 100 | 0.5% L-77 | 64 | 63 |
| Formulation B | none | 100 | 3.0% L-77 | 40 | 70 |
| Formulation B | 0.5% Neo 1-5 | 100 | none | 50 | 43 |
| Formulation B | 3.0% Neo 1-5 | 100 | none | 30 | 23 |
| Formulation B | none | 100 | 0.5% Neo 1-5 | 58 | 73 |
| Formulation B | none | 100 | 3.0% Neo 1-5 | 50 | 70 |
| Formulation B | 0.5% Neo 1'45 + L-77, 2:1 | 100 | none | 60 | 45 |
| Formuiation B | 3.0% Neo 1-5+ L-77, 2:1 | 100 | none | 45 | 15 |
| Formulation B | none | 100 | 0.5% Neo 1-5 + L-77, 2:1 | 50 | 74 |
| Formulation B | none | 100 | 3.0% Neo 1-5 + L-77, 2:1 | 50 | 65 |
| Formulation B | 0.5% Neo 1-5+ L-77, 1:2 | 100 | none | 50 | 30 |
| Formulation B | 3.0% Neo 1-5+ L-77,1:2 | 100 | none | 50 | 38 |
| Formulation B | none | 100 | 0.5% Neo 1-5 + L-77, 1:2 | 68 | 55 |
| Formulation B | none | 100 | 3.0% Neo 1-5 + L-77, 1:2 | 35 | 63 |
| Formulation B | 0.5% Neo 1-5 + L-77, 1:1 | 100 | none | 50 | 28 |
| Formulation B | 3.0% Neo 1-5 + L-77, 1:1 | 100 | none | 53 | 20 |
| Formulation B | none | 100 | 0.5% Neo 1-5 + L-77,1:1 | 53 | 73 |
| Formulation B | none | 100 | 3.0% Neo 1-5 + L-77, 1:1 | 43 | 63 |
| Formulation B | 0.5% Neo 1-5 + L-77,1:9 | 100 | none | 70 | 30 |
| Formulation B | 3.0% Neo 1-5+ L-77, 1:9 | 100 | none | 58 | 48 |
| Formulation B | none | 100 | 0.5% Neo 1-5 + L-77, 1:9 | 58 | 71 |
| Formulation B | none | 100 | 3.0% Neo 1-5 + L-77, 1:9 | 63 | 65 |
| Formulation B | 0.5% Neo 1-5 + L-77, 9:1 | 100 | none | 45 | 45 |
| Formulation B | 3.0% Neo 1-5 + L-77, 9:1 | 100 | none | 48 | 35 |
| Formulation B | none | 100 | 0.5% Neo 1-5 + L-77, 9:1 | 50 | 70 |
| Formulation B | none | 100 | 3.0% Neo 1-5 + L-77, 9:1 | 50 | 58 |

Example 36

Velvetleaf (*Abutilon theophrasti*, ABUTH) and Japanese millet (*Echinochloa crus-galli*, ECHCF) plants were grown in pots, maintained in a greenhouse and treated with initial and subsequent applications by procedures exactly as described for Example 1, except where otherwise noted below.

The experimental design included four replicate pots per treatment. Initial applications of Formulation B, in tank mix with MON-0818 surfactant and/or an accession agent, were applied 22 days after planting velvetleaf and 20 days after planting Japanese millet. MON-0818 was used at a concentration of 0.09% in the initial application spray solution in all treatments, except where MON-0818 itself was being tested as a candidate accession agent (see below). Formulation B was applied without accession agent at a range of rates from 200 to 1000 g a.e./ha. When an accession agent was included in the treatment, either in tank mix or as a subsequent application, Formulation B was tested only at 200 and 400 g a.e./ha, with 0.09% MON-0818. This Example includes as an accession agent an aqueous solution containing 0.5% Silwet L-77. Other candidate accession agents tested in this Example include aqueous solutions, at concentrations of 1.5% and 5.0%, of the following surfactants or other substances:

Neodol 91-8 of Shell Chemical Company: described in McCutcheon's (loc. cit.) as $C_{9-11}$ primary alcohol ethoxylate having 8 moles EO.

MON-0818: tallowamine (15EO) ethoxylate based surfactant of Monsanto Company. In the tank mix applications using MON-0818 as a candidate accession test were examined by a single practiced technician to evaluate percent inhibition. Treatments and corresponding percent inhibitions are given in Table 36.

TABLE 36

| Initial application 93 l/ha, no MON-0818 | | Glyphosate rate | Subsequent application 93 l/ha | % Inhibition | |
|---|---|---|---|---|---|
| herbicide | accession agent | g a.e./ha | accession agent at 4 hrs | ABUTH | ECHCF |
| Formulation B | none | 200 | none | 29 | 78 |
| Formulation B | none | 400 | none | 55 | 100 |
| Formulation B | none | 600 | none | 73 | 100 |
| Formulation B | none | 800 | none | 92 | 100 |
| Formulation B | none | 1000 | none | 95 | 100 |
| Formulation B | 0.5% L-77 | 200 | none | 54 | 20 |
| Formulation B | 0.5% L-77 | 400 | none | 81 | 31 |
| Formulation B | none | 200 | 0.5% L-77 | 54 | 58 |
| Formulation B | none | 400 | 0.5% L-77 | 75 | 85 |
| Formulation B | 1.5% Neo 91-8 | 200 | none | 44 | 70 |
| Formulation B | 1.5% Neo 91-8 | 400 | none | 50 | 91 |
| Formulation B | 5.0% Neo 91-8 | 200 | none | 18 | 35 |
| Formulation B | 5.0% Neo 91-8 | 400 | none | 49 | 76 |
| Formulation B | none | 200 | 1.5% Neo 91-8 | 40 | 72 |
| Formulation B | none | 400 | 1.5% Neo 91-8 | 50 | 93 |
| Formulation B | none | 200 | 5.0% Neo 91-8 | 27 | 65 |
| Formulation B | none | 400 | 5.0% Neo 91-8 | 49 | 83 |
| Formulation B | 1.5% MON-0818 | 200 | none | 66 | 84 |
| Formulation B | 1.5% MON-0818 | 400 | none | 76 | 100 |
| Formulation B | 5.0% MON-0818 | 200 | none | 35 | 91 |
| Formulation B | 5.0% MON-0818 | 400 | none | 63 | 93 |
| Formulation B | none | 200 | 1.5% MON-0818 | 31 | 88 |
| Formulation B | none | 400 | 1.5% MON-0818 | 73 | 95 |
| Formulation B | none | 200 | 5.0% MON-0818 | 48 | 78 |
| Formulation B | none | 400 | 5.0% MON-O8#8 | 49 | 88 |
| Formulation B | 1.5% glycerin | 200 | none | 19 | 81 |
| Formulation B | 1.5% glycerin | 400 | none | 55 | 100 |
| Formulation B | 5.0% glycerin | 200 | none | 53 | 88 |
| Formulation B | 5.0% glycerin | 400 | none | 55 | 95 |
| Formulation B | none | 200 | 1.5% glycerin | 24 | 96 |
| Formulation B | none | 400 | 1.5% glycerin | 76 | 99 |
| Formulation B | none | 200 | 5.0% glycerin | 31 | 95 |
| Formulation B | none | 400 | 5.0% glycerin | 50 | 91 |
| Formulation B | 1.5% Tween 20 | 200 | none | 20 | 66 |
| Formulation B | 1.5% Tween 20 | 400 | none | 38 | 68 |
| Formulation B | 5.0% Tween 20 | 200 | none | 29 | 55 |
| Formulation B | 5.0% Tween 20 | 400 | none | 43 | 79 |
| Formulation B | ndne | 200 | 1.5% Tween 20 | 21 | 71 |
| Formulation B | none | 400 | 1.5% Tween 20 | 66 | 98 |
| Formulation B | none | 200 | 5.0% Tween 20 | 39 | 80 |
| Formulation B | none | 400 | 5.0% Tween 20 | 65 | 94 |
| Formulation B | 1.5% 15-S-9 | 200 | none | 31 | 70 |
| Formulation B | 1.5% 15-S-9 | 400 | none | 51 | 100 |
| Formulation B | 5.0% 15-S-9 | 200 | none | 21 | 333 |
| Formulation B | 5.0% 15-S-9 | 400 | none | 39 | 39 |
| Formulation B | none | 200 | 1.5% 15-S-9 | 38 | 64 |
| Formulation B | none | 400 | 1.5% 15-S-9 | 59 | 86 |
| Formulation B | none | 200 | 5.0% 15-S-9 | 34 | 60 |
| Formulation B | none | 400 | 5.0% 15-S-9 | 66 | 96 | agent, a further 0.09% MON-0818 was not added to the tank mix.
Glycerin.
Tween 20 of ICI Surfactants: described in McCutcheon's (loc. cit.) as polyoxyethylene (20) sorbitan monolaurate.
Tergitol 15-S-9 of Union Carbide Corporation: described in McCutcheon's (loc. cit.) as $C_{11-15}$ secondary alcohol ethoxylate, believed to have 9 moles EO; abbreviated in tables herein as "15-S-9".
The time interval between initial and subsequent applications was 3 hours.
Nineteen days after the initial application, all plants in the Example 37

Velvetleaf (*Abutilon theophrasti*, ABUTH) and Japanese millet (*Echinochloa crus-galli*, ECHCF) plants were grown in pots, maintained in a greenhouse and treated with initial and subsequent applications by procedures exactly as described for Example 1, except where otherwise noted below.

The experimental design included four replicate pots per treatment. Initial applications of Formulation B, in tank mix with MON-0818 surfactant or with MON-0818 and an accession agent, were applied 15 days after planting velvetleaf and 18 days after planting Japanese millet. MON- 0818 was used at a concentration of 0.09% in the initial application spray solution in all treatments. Formulation B was applied without accession agent at a range of rates from 200 to 1000 g a.e./ha. When an accession agent was included in the treatment, either in tank mix or as a subsequent application, Formulation B was tested only at 200 and 400 g a.e./ha, with 0.09% MON-0818. This Example includes as an accession agent an aqueous solution containing 0.5% Silwet L-77. Other candidate accession agents tested in this Example include aqueous solutions, at concentrations of 1.5% and 5.0%, of the following surfactants or other substances:

A 1:1 weight/weight blend of Ethomeen C/15 of Akzo Chemicals Inc. with Tergitol 15-S-9 as described above; Ethomeen C/15 is described in Akzo's brochure titled "Ethoxylated and propoxylated surfactants" published 1991 as ethoxylated cocoamine having 5 moles EO; abbreviated in tables herein as "Em C/15".

Agrimul PG 2069 as described above.

Surfynol 465 as described above.

Miranol C2M of Rhone-Poulenc: described in McCutcheon's (loc. cit.) as a dicarboxylic coconut derivative, disodium salt; abbreviated in tables herein as "Miranol".

Ethoquad C/12 of Akzo Chemicals Inc.: described in Akzo's brochure titled "Ethoxylated and propoxylated surfactants" published 1991 as 75% ethoxylated cocoalkylmethyl quaternary ammonium chloride having 2 moles EO; abbreviated in tables herein as "Eq C/12".

Aerosol OT of Cytec Industries, a unit of American Cyanamid: described in McCutcheon's (loc. cit.) as dioctyl ester of sodium sulfosuccinic acid; abbreviated in tables herein as "AOT".

The time interval between initial and subsequent applications was 3 hours.

Twenty days after the initial application, all plants in the test were examined by a single practiced technician to evaluate percent inhibition. Treatments and corresponding percent inhibitions are given in Table 37.

TABLE 37

| Initial application 93 l/ha, no MON-0818 | | Glyphosate rate | Subsequent application 93 l/ha | % Inhibition | |
|---|---|---|---|---|---|
| herbicide | accession agent | g a.e./ha | accession agent at 4 hrs | ABUTH | ECHCF |
| Formulation B | none | 200 | none | 41 | 29 |
| Formulation B | none | 400 | none | 97 | 98 |
| Formulation B | none | 600 | none | 99 | 95 |
| Formulation B | none | 800 | none | 100 | 96 |
| Formulation B | none | 1000 | none | 100 | 100 |
| Formulation B | 0.5% L-77 | 200 | none | 87 | 33 |
| Formulation B | 0.5% L-77 | 400 | none | 95 | 33 |
| Formulation B | none | 200 | 0.5% L-77 | 93 | 91 |
| Formulation B | none | 400 | 0.5% L-77 | 100 | 98 |
| Formulation B | 1.5% Em C/15 + 15-S-9, 1:1 | 200 | none | 14 | 92 |
| Formulation B | 1.5% Em C/15 + 15-S-9, 1:1 | 400 | none | 99 | 86 |
| Formulation B | 5.0% Em C/15 + 15-S-9, 1:1 | 200 | none | 55 | 64 |
| Formulation B | 5.0% Em C/15 + 15-S-9, 1:1 | 400 | none | 55 | 72 |
| Formulation B | none | 200 | 1.5% Em C/15 + 15-S-9, 1:1 | 81 | 80 |
| Formulation B | none | 400 | 1.5% Em C/15 + 15-S-9, 1:1 | 100 | 94 |
| Formulation B | none | 200 | 5.0% Em C/15 + 15-S-9, 1:1 | 36 | 53 |
| Formulation B | none | 400 | 5.0% Em C/15 + 15-S-9, 1:1 | 75 | 85 |
| Formulation B | 1.5% PG 2069 | 200 | none | 94 | 94 |
| Formulation B | 1.5% PG 2069 | 400 | none | 100 | 100 |
| Formulation B | 5.0% PG 2069 | 200 | none | 83 | 93 |
| Formulation B | 5.0% PG 2069 | 400 | none | 100 | 100 |
| Formulation B | none | 200 | 1.5% PG 2069 | 66 | 99 |
| Formulation B | none | 400 | 1.5% PG 2069 | 98 | 99 |
| Formulation B | none | 200 | 5.0% PG 2069 | 80 | 96 |
| Formulation B | none | 400 | 5.0% PG 2069 | 100 | 93 |
| Formulation B | 1.5% Surf 465 | 200 | none | 94 | 89 |
| Formulation B | 1.5% Surf 465 | 400 | none | 99 | 98 |
| Formulation B | 5.0% Surf 465 | 200 | none | 79 | 92 |
| Formulation B | 5.0% Surf 465 | 400 | none | 92 | 98 |
| Formulation B | none | 200 | 1.5% Surf 465 | 76 | 79 |
| Formulation B | none | 400 | 1.5% Surf 465 | 99 | 96 |
| Formulation B | none | 200 | 5.0% Surf 465 | 68 | 82 |
| Formulation B | none | 400 | 5.0% Surf 465 | 88 | 95 |
| Formulation B | 1.5% Miranol | 200 | none | 70 | 87 |
| Formulation B | 1.5% Miranol | 400 | none | 96 | 90 |
| Formulation B | 5.0% Miranol | 200 | none | 90 | 93 |
| Formulation B | 5.0% Miranol | 400 | none | 99 | 95 |

TABLE 37-continued

| herbicide | Initial application 93 1/ha, no MON-0818 accession agent | Glyphosate rate g a.e./ha | Subsequent application 93 1/ha accession agent at 4 hrs | % Inhibition ABUTH | ECHCF |
|---|---|---|---|---|---|
| Formulation B | none | 200 | 1.5% Miranol | 84 | 92 |
| Formulation B | none | 400 | 1.5% Miranol | 99 | 98 |
| Formulation B | none | 200 | 5.0% Miranol | 88 | 88 |
| Formulation B | none | 400 | 5.0% Miranol | 95 | 83 |
| Formulation B | 1.5% Eq C/12 | 200 | none | 66 | 62 |
| Formulation B | 1.5% Eq C/12 | 400 | none | 92 | 78 |
| Formulation B | 5.0% Eq C/12 | 200 | none | 48 | 48 |
| Formulation B | 5.0% Eq C/12 | 400 | none | 81 | 84 |
| Formulation B | none | 200 | 1.5% Eq C/12 | 8 | .21 |
| Formulation B | non& | 400 | 1.5% Eq C/12 | 92 | 84 |
| Formulation B | none | 200 | 5.0% Eq C/12 | 31 | 68 |
| Formulation B | none | 400 | 5.0% Eq C/12 | 71 | 92 |
| Formulation B | 1.5% AOT | 200 | none | 75 | 75 |
| Formulation B | 1.5% AOT | 400 | none | 85 | 72 |
| Formulation B | 5.0% AOT | 200 | none | 24 | 24 |
| Formulation B | 5.0% AOT | 400 | none | 53 | 8 |
| Formulation B | none | 200 | 1.5% AOT | 30 | 40 |
| Formulation B | none | 400 | 1.5% AOT | 73 | 89 |
| Formulation B | none | 200 | 5.0% AOT | 53 | 79 |
| Formulation B | none | 400 | 5.0% AOT | 69 | 87 |

Example 38

The procedures of Example 30 were repeated exactly except that initial applications were made 14 days after planting velvetleaf and 17 days after planting Japanese millet, percent inhibition was determined twenty days after initial application, accession agents were applied in tank mix and subsequent applications at concentrations of 0.25% and 0.5%, and the candidate accession agents in addition to Silwet L-77 were the following organosilicone surfactants of OSi Specialties, abbreviated in tables herein by omission of the "Silwet" trademark:

Silwet 408, available from OSi but composition not disclosed.

Silwet 800, available from OSi but composition not disclosed.

Silwet L-7001, described in OSi Specialties brochure titled "Silwet surfactants" published 1994 as a 75% product having the general formula

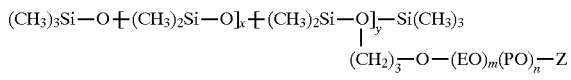

where EO refers to ethylene oxide units and PO to propylene oxide units; in Silwet L-7001 the ratio of m to n is 40/60, Z is methyl and the average molecular weight is 20,000.

Silwet L-7500, described in the OSi Specialties brochure cited above as being a 100% product having the same general formula as Silwet L-7001 but with all PO units (no EO), Z being butyl and the average molecular weight being 3000.

Silwet L-7604, described in the OSi Specialties brochure cited above as being a 100% product having the same general formula as Silwet L-7001 but with all EO units (no PO), Z being hydrogen and the average molecular weight being 4000.

Silwet L-7605, described in the OSi Specialties brochure cited above as being a 100% product having the same general formula as Silwet L-7001 but with all EO units (no PO), Z being methyl and the average molecular weight being 6000.

Treatments and corresponding percent inhibitions are given in Table 38a (Formulation B applied without MON-0818) and 38b (Formulation B applied with 0.09% MON-0818).

TABLE 38a

| herbicide | Initial application 93 1/ha, no MON-0818 accession agent | Glyphosate rate g a.e./ha | Subsequent application 93 1/ha accession agent at 4 hrs | % Inhibition ABUTH | ECHCF |
|---|---|---|---|---|---|
| Formulation B | none | 100 | none | 30 | 20 |
| Formulation B | none | 300 | none | 73 | 81 |
| Formulation B | none | 400 | none | 78 | 80 |
| Formulation B | none | 500 | none | 83 | 83 |
| Formulation B | 0.25% L-77 | 100 | none | 66 | 5 |
| Formulation B | 0.5% L-77 | 100 | none | 75 | 5 |
| Formulation B | none | 100 | 0.25% L-77 | 70 | 30 |

TABLE 38a-continued

| herbicide | Initial application 93 1/ha, no MON-0818 accession agent | Glyphosate rate g a.e./ha | Subsequent application 93 1/ha accession agent at 4 hrs | % Inhibition ABUTH | ECHCF |
|---|---|---|---|---|---|
| Formulation B | none | 100 | 0.5% L-77 | 75 | 10 |
| Formulation B | 0.25% 408 | 100 | none | 70 | 10 |
| Formulation B | 0.5% 408 | 100 | none | 76 | 10 |
| Formulation B | none | 100 | 0.25% 408 | 70 | 20 |
| Formulation B | none | 100 | 0.5% 408 | 74 | 20 |
| Formulation B | 0.25% 800 | 100 | none | 70 | 10 |
| Formulation B | 0.5% 800 | 100 | none | 78 | 10 |
| Formulation B | none | 100 | 0.25% 800 | 60 | 30 |
| Formulation B | none | 100 | 0.5% 800 | 74 | 25 |
| Formulation B | 0.25% L-7001 | 100 | none | 60 | 10 |
| Formulation B | 0.5% L-7001 | 100 | none | 50 | 15 |
| Formulation B | none | 100 | 0.25% L-7001 | 50 | 38 |
| Formulation B | none | 100 | 0.5% L-7001 | 28 | 30 |
| Formulation B | 0.25% L-7500 | 100 | none | 48 | 20 |
| Formulation B | 0.5% L-7500 | 100 | none | 40 | 30 |
| Formulation B | none | 100 | 0.25% L-7500 | 48 | 30 |
| Formulation B | none | 100 | 0.5% L-7500 | 25 | 20 |
| Formulation B | 0.25% L-7604 | 100 | none | 68 | 35 |
| Formulation B | 0.5% L-7604 | 100 | none | 75 | 73 |
| Formulation B | none | 100 | 0.25% L-7604 | 55 | 23 |
| Formulation B | none | 100 | 0.5% L-7604 | 53 | 20 |
| Formulation B | 0.25% L-7605 | 100 | none | 68 | 51 |
| Formulation B | 0.5% L-7605 | 100 | none | 75 | 50 |
| Formulation B | none | 100 | 0.25% L-7605 | 70 | 45 |
| Formulation B | none | 100 | 0.5% L-7605 | 60 | 33 |

TABLE 38b

| herbicide | Initial application 93 1/ha, 0.09% MON-0818 accession agent | Glyphosate rate g a.e./ha | Subsequent application 93 1/ha accession agent at 4 hrs | % Inhibition ABUTH | ECHCF |
|---|---|---|---|---|---|
| Formulation B | none | 100 | none | 60 | 90 |
| Formulation B | none | 300 | none | 79 | 97 |
| Formulation B | none | 400 | none | 94 | 98 |
| Formulation B | none | 500 | none | 94 | 98 |
| Formulation B | 0.25% L-77 | 100 | none | 68 | 5 |
| Formulation B | 0.5% L-77 | 100 | none | 75 | 5 |
| Formulation B | none | 100 | 0.25% L-77 | 60 | 58 |
| Formulation B | none | 100 | 0.5% L-77 | 75 | 48 |
| Formulation B | 0.25% 408 | 100 | none | 63 | 18 |
| Formulation B | 0.5% 408 | 100 | none | 75 | 20 |
| Formulation B | none | 100 | 0.25% 408 | 68 | 43 |
| Formulation B | none | 100 | 0.5% 408 | 75 | 45 |
| Formulation B | 0.25% 800 | 100 | none | 70 | 10 |
| Formulation B | 0.5% 800 | 100 | none | 78 | 10 |
| Formulation B | none | 100 | 0.25% 800 | 74 | 65 |
| Formulation B | none | 100 | 0.5% 800 | 78 | 43 |
| Formulation B | 0.25% L-7001 | 100 | none | 70 | 30 |
| Formulation B | 0.5% L-7001 | 100 | none | 73 | 35 |
| Formulation B | none | 100 | 0.25% L-7001 | 63 | 43 |
| Formulation B | none | 100 | 0.5% L-7001 | 55 | 79 |
| Formulation B | 0.25% L-7500 | 100 | none | 66 | 60 |
| Formulation B | 0.5% L-7500 | 100 | none | 75 | 70 |
| Formulation B | none | 100 | 0.25% L-7500 | 65 | 68 |
| Formulation B | ndne | 100 | 0.5% L-7500 | 53 | 65 |
| Formulation B | 0.25% L-7604 | 100 | none | 70 | 50 |
| Formulation B | 0.5% L-7604 | 100 | none | 75 | 60 |
| Formulation B | none | 100 | 0.25% L-7604 | 65 | 63 |
| Formulation B | none | 100 | 0.5% L-7604 | 70 | 65 |
| Formulation B | 0.25% L-7605 | 100 | none | 70 | 55 |
| Formulation B | 0.5% L-7605 | 100 | none | 80 | 74 |
| Formulation B | none | 100 | 0.25% L-7605 | 69 | 55 |
| Formulation B | none | 100 | 0.5% L-7605 | 70 | 60 |

Example 39

The procedures of Example 30 were repeated exactly except that initial applications were made 13 days after planting velvetleaf and 16 days after planting Japanese millet, percent inhibition was determined twenty days after initial application, accession agents were applied in tank mix and subsequent applications at concentrations of 0.25% and 0.5%, and the candidate accession agents in addition to Silwet L-77 were:

Ethomeen T/30 of Akzo Chemicals Inc.: not specifically described in Akzo's brochure titled "Ethoxylated and propoxylated surfactants" published 1991 but believed to be ethoxylated tallowamine having 20 moles EO; abbreviated in tables herein as "Em T/30".

Treatments and corresponding percent inhibitions are given in Table 39a (Formulation B applied without MON-0818) and 39b (Formulation B applied with 0.09% MON-0818).

TABLE 39a

| | Initial application 93 l/ha, no MON-0818 | | Subsequent Glyphosate application 93 l/ha | | % Inhibition | |
|---|---|---|---|---|---|---|
| herbicide | accession agent | rate g a.e./ha | accession agent at 4 hrs | | ABUTH | ECHF |
| Formulation B | none | 100 | none | | 50 | 20 |
| Formulation B | none | 300 | none | | 93 | 55 |
| Formulation B | none | 400 | none | | 97 | 60 |
| Formulation B | none | 500 | none | | 100 | 92 |
| Formulation B | 0.25% L-77 | 100 | none | | 74 | 10 |
| Formulation B | 0.5% L-77 | 100 | none | | 90 | 10 |
| Formulation B | none | 100 | 0.25% L-77 | | 76 | 30 |
| Formulation B | none | 100 | 0.5% L-77 | | 83 | 20 |
| Formulation B | 0.25% L-720 | 100 | none | | 53 | 58 |
| Formulation B | 0.5% L-720 | 100 | none | | 55 | 60 |
| Formulation B | none | 100 | 0.25% L-720 | | 50 | 40 |
| Formulation B | none | 100 | 0.5% L-720 | | 45 | 20 |
| Formulation B | 0.25% Em T/30 | 100 | none | | 83 | 79 |
| Formulation B | 0.5% Em T/30 | 100 | none | | 80 | 85 |
| Formulation B | none | 100 | 0.25% Em T/30 | | 65 | 40 |
| Formulation B | none | 100 | 0.5% Em T/30 | | 60 | 30 |

TABLE 39b

| | Initial application 93 l/ha, 0.09% MON-0818 | | Subsequent Glyphosate application 93 l/ha | | % Inhibition | |
|---|---|---|---|---|---|---|
| herbicide | accession agent | rate g a.e./ha | accession agent at 4 hrs | | ABUTH | ECHF |
| Formulation B | none | 100 | none | | 79 | 78 |
| Formulation B | none | 300 | none | | 98 | 98 |
| Formulation B | none | 400 | none | | 100 | 100 |
| Formulation B | none | 500 | none | | 99 | 100 |
| Formulation B | 0.25% L-77 | 100 | none | | 78 | 15 |
| Formulation B | 0.5% L-77 | 100 | none | | 85 | 20 |
| Formulation B | none | 100 | 0.25% L-77 | | 78 | 69 |
| Formulation B | none | 100 | 0.5% L-77 | | 83 | 75 |
| Formulation B | 0.25% L-720 | 100 | none | | 74 | 73 |
| Formulation B | 0.5% L-720 | 100 | none | | 73 | 70 |
| Formulation B | none | 100 | 0.25% L-720 | | 76 | 78 |
| Fonnulation B | none | 100 | 0.5% L-720 | | 70 | 71 |
| Formulation B | 0.25% Em T/30 | 100 | none | | 80 | 83 |
| Formulation B | 0.5% Em T/30 | 100 | none | | 80 | 69 |
| Formulation B | none | 100 | 0.25% Em T/30 | | 75 | 69 |
| Formulation B | none | 100 | 0.5% Em T/30 | | 75 | 70 |

Silwet L-720, described in OSi Specialties brochure titled "Silwet surfactants" published 1994 as a 50% product having the general formula

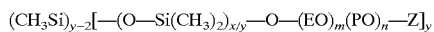

where EO refers to ethylene oxide units and PO to propylene oxide units; in Silwet L-720 the ratio of m to n is 50/50, Z is butyl and the average molecular weight is 12,000.

Example 40

The procedures of Example 30 were repeated exactly except that initial applications were made 20 days after planting velvetleaf and 17 days after planting Japanese millet, percent inhibition was determined twenty days after initial application, accession agents were applied in tank mix and subsequent applications at concentrations of 0.25% and 0.5%, and the candidate accession agents in addition to Silwet L-77 were:

Ganex P-904 of ISP: described in ISP Product Literature as alkylated polyvinylpyrrolidone; abbreviated in tables herein as "P-904".

Fluorad FC-120 of 3M Company: described in McCutcheon's (loc. cit.) as 25% ammonium perfluoroalkyl sulfonate.

Fluorad FC-129 of 3M Company: described in McCutcheon's (loc. cit.) as 50% potassium fluorinated alkyl carboxylates.

Fluorad FC-170-C of 3M Company: described in McCutcheon's (loc. cit.) as 95% fluorinated alkyl polyoxyethylene ethanols; abbreviated in tables herein as FC-170.

Fluorad FC-171 of 3M Company: described in McCutcheon's (loc. cit.) as 100% fluorinated alkyl alkoxylate.

Fluorad FC-430 of 3M Company: described in McCutcheon's (loc. cit.) as 100% fluorinated alkyl esters.

Treatments and corresponding percent inhibitions are given in Table 40a (Formulation B applied without MON-0818) and 40b (Formulation B applied with 0.09% MON-0818).

TABLE 40a

| Initial application 93 l/ha, no MON-0818 | | Subsequent Glyphosate | application 93 l/ha | % Inhibition | |
|---|---|---|---|---|---|
| herbicide | accession agent | rate g a.e./ha | accession agent at 4 hrs | ABUTH | ECHF |
| Formulation B | none | 100 | none | 50 | 33 |
| Formulation B | none | 300 | none | 88 | 75 |
| Formulation B | none | 400 | none | 95 | 83 |
| Formulation B | none | 500 | none | 97 | 94 |
| Formulation B | 0.25% L-77 | 100 | none | 76 | 20 |
| Formulation B | 0.5% L-77 | 100 | none | 76 | 13 |
| Formulation B | none | 100 | 0.25% L-77 | 71 | 45 |
| Formulation B | none | 100 | 0.5% L-77 | 73 | 30 |
| Formulation B | 0.25% P-904 | 100 | none | 65 | 73 |
| Formulation B | 0.5% P-904 | 100 | none | 30 | 58 |
| Formulation B | none | 100 | 0.25% P-904 | 48 | 64 |
| Formulation B | none | 100 | 0.5% P-904 | 20 | 30 |
| Formulation B | 0.25% FC-120 | 100 | none | 76 | 25 |
| Formulation B | 0.5% FC-120 | 100 | none | 70 | 28 |
| Formulation B | none | 100 | 0.25% FC-120 | 63 | 40 |
| Formulation B | none | 100 | 0.5% FC-120 | 75 | 35 |
| Formulation B | 0.25% FC-129 | 100 | none | 50 | 10 |
| Formulation B | 0.5% FC-129 | 100 | none | 63 | 10 |
| Formulation B | none | 100 | 0.25% FC-129 | 60 | 43 |
| Formulation B | none | 100 | 0.50% FC-129 | 58 | 35 |
| Formulation B | 0.25% FC-170 | 100 | none | 70 | 33 |
| Formulation B | 0.5% FC-170 | 100 | none | 69 | 40 |
| Formulation B | none | 100 | 0.25% FC-170 | 68 | 48 |
| Formulation B | none | 100 | 0.5% FC-170 | 75 | 38 |
| Formulation B | 0.25% FC-171 | 100 | none | 55 | 30 |
| Formulation B | 0.5% FC-171 | 100 | none | 25 | 30 |
| Formulation B | none | 100 | 0.25% FC-171 | 48 | 55 |
| Formulation B | none | 100 | 0.5% FC-171 | 30 | 35 |
| Formulation B | 0.25% FC-430 | 100 | none | 45 | 40 |
| Formulation B | 0.5% FC-430 | 100 | none | 53 | 60 |
| Formulation B | none | 100 | 0.25% FC-430 | 50 | 48 |
| Formulation B | none | 100 | 0.5% FC-430 | 33 | 40 |

TABLE 40b

| Initial application 93 l/ha, 0.09% MON-0818 | | Subsequent Glyphosate | application 93 l/ha | % Inhibition | |
|---|---|---|---|---|---|
| herbicide | accession agent | rate g a.e./ha | accession agent at 4 hrs | ABUTH | ECHF |
| Formulation B | none | 100 | none | 74 | 97 |
| Formulation B | none | 300 | none | 96 | 99 |
| Formulation B | none | 400 | none | 97 | 100 |
| Formulation B | none | 500 | none | 99 | 100 |
| Formulation B | 0.25% L-77 | 100 | none | 58 | 30 |
| Formulation B | 0.5% L-77 | 100 | none | 78 | 13 |
| Formulation B | none | 100 | 0.25% L-77 | 70 | 75 |
| Formulation B | none | 100 | 0.5% L-77 | 75 | 80 |
| Formulation B | 0.25% P-904 | 100 | none | 73 | 96 |
| Formulation B | 0.5% P-904 | 100 | none | 69 | 89 |

TABLE 40b-continued

| | Initial application 93 l/ha, 0.09% MON-0818 | Subsequent Glyphosate | application 93 l/ha | % Inhibition | |
|---|---|---|---|---|---|
| herbicide | accession agent | rate g a.e./ha | accession agent at 4 hrs | ABUTH | ECHF |
| Formulation B | none | 100 | 0.25% P-904 | 70 | 83 |
| Formulation B | none | 100 | 0.5% P-904 | 30 | 83 |
| Formulation B | 0.25% FC-120 | 100 | none | 74 | 20 |
| Formulation B | 0.5% FC-120 | 190 | none | 66 | 30 |
| Formulation B | none | 100 | 0.25% FC-120 | 80 | 75 |
| Formulation B | none | 100 | 0.5% FC-120 | 60 | 83 |
| Formulation B | 0.25% FC-129 | 100 | none | 73 | 40 |
| Formulation B | 0.5% FC-129 | 100 | none | 73 | 23 |
| Formulation B | none | 100 | 0.25% FC-129 | 6& | 65 |
| Formulation B | none | 100 | 0.5% FC-129 | 65 | 75 |
| Formulation B | 0.25% FC-170 | 100 | none | 75 | 73 |
| Formulation B | 0.5% FC-170 | 100 | none | 73 | 73 |
| Formulation B | none | 100 | 0.25% FC-170 | 75 | 80 |
| Formulation B | none | 100 | 0.5% FC-170 | 78 | 93 |
| Formulation B | 0.25% FC-171 | 100 | none | 79 | 65 |
| Formulation B | 0.5% FC-171 | 100 | none | 55 | 70 |
| Formulation B | none | 100 | 0.25% FC-171 | 70 | 85 |
| Formulation B | none | 100 | 0.5% FC-171 | 45 | 79 |
| Formulation B | 0.25% FC-430 | 100 | none | 75 | 60 |
| Formulation B | 0.5% FC-430 | 100 | none | 69 | 68 |
| Formulation B | none | 100 | 0.25% FC-430 | 65 | 80 |
| Formulation B | none | 100 | 0.5% FC-430 | 58 | 71 |

Example 41

The procedures of Example 30 were repeated exactly except that initial applications were made 17 days after planting velvetleaf and 19 days after planting Japanese millet, percent inhibition was determined eighteen days after initial application, and the candidate accession agents in addition to Silwet L-77 were:

Fluorad FC-129 as described above.

Fluorad FC-135 as described above.

Kinetic: a commercial agricultural spray adjuvant of Helena Chemical Company, containing an organosilicone surfactant.

Treatments and corresponding percent inhibitions are given in Table 41a (Formulation B applied without MON-0818) and 41b (Formulation B applied with 0.09% MON-0818).

TABLE 41a

| | Initial application 93 l/ha, no MON-0818 | Subsequent Glyphosate | application 93 l/ha | % Inhibition | |
|---|---|---|---|---|---|
| herbicide | accession agent | rate g a.e./ha | accession agent at 4 hrs | ABUTH | ECHF |
| Formulation B | none | 100 | none | 3 | 43 |
| Formulation B | none | 300 | none | 40 | 80 |
| Formulation B | none | 400 | none | 65 | 93 |
| Formulation B | none | 500 | none | 83 | 94 |
| Formulation B | 0.5% L-77 | 100 | none | 75 | 25 |
| Formulation B | 3.0% L-77 | 100 | none | 70 | 33 |
| Formulation B | none | 100 | 0.5% L-77 | 75 | 50 |
| Formulation B | none | 100 | 3.0% L-77 | 35 | 38 |
| Formulation B | 0.5% FC-129 | 100 | none | 40 | 33 |
| Formulation B | 3.0% FC-129 | 100 | none | 50 | 50 |
| Formulation B | none | 100 | 0.5% FC-129 | 84 | 65 |
| Formulation B | none | 100 | 3.0% FC-129 | 50 | 43 |
| Formulation B | 0.5% FC-135 | 100 | none | 66 | 83 |
| Formulation B | 3.0% FC-135 | 100 | none | 61 | 64 |
| Formulation B | none | 100 | 0.5% FC-135 | 58 | 55 |
| Formulation B | none | 100 | 3.0% FC-135 | 53 | 40 |
| Formulation B | 0.5% Kinetic | 100 | none | 68 | 35 |
| Formulation B | 3.0% Kinetic | 100 | none | 78 | 38 |
| Formulation B | none | 100 | 0.5% Kinetic | 58 | 48 |
| Formulation B | none | 100 | 3.0% Kinetic | 68 | 38 |
| Formulation B | FC-129 + L-77 (1:49) at 0.5% | 100 | none | 83 | 35 |
| Formulation B | FC-129 + L-77 (1:49) at 3.0% | 100 | none | 73 | 350 |
| Formulation B | none | 100 | FC-129 + L-77 | 78 | 49 |

TABLE 41a-continued

| | Initial application 93 l/ha, no MON-0818 | Subsequent Glyphosate | application 93 l/ha | % Inhibition | |
|---|---|---|---|---|---|
| herbicide | accession agent | rate g a.e./ha | accession agent at 4 hrs | ABUTH | ECHF |
| Formulation B | none | 1oo | FC-129 + L-77 (1:49) at 0.5% | 58 | 35 |
| Formulation B | FC-129 + L-77 (1:19) at 0.5% | 100 | FC-129 + L-77 (1:49) at 3.0% none | 84 | 30 |
| Formulation B | FC-129 + L-77 (1:19) at 3.0% | 100 | none | 78 | 40 |
| Formulation B | none | 100 | FC-129 + L-77 (1:19) at 0.5% | 75 | 55 |
| Formulation B | none | 100 | FC-129 + L-77 (1:19) at 3.0% | 60 | 33 |
| Formulation B | FC-129 + L-77 (1:9) at 0.5% | 100 | none | 84 | 38 |
| Formulation B | FC-129 + L-77 (1:9) at 3.0% | 100 | none | 75 | 35 |
| Formulation B | none | 100 | FC-129 + L-77 (1:9) at 0.5% | 79 | 45 |
| Formulation B | none | 100 | FC-129 + L-77 (1:9) at 3.0% | 63 | 33 |

TABLE 41b

| | Initial application 93 l/ha, 0.09% MON-0818 | Subsequent Glyphosate | application 93 l/ha | % Inhibition | |
|---|---|---|---|---|---|
| herbicide | accession agent | rate g a.e./ha | accession agent at 4 hrs | ABUTH | ECHF |
| Formulation B | none | 100 | none | 30 | 98 |
| Formulation B | none | 300 | none | 64 | 100 |
| Formulation B | none | 400 | none | 79 | 100 |
| Fonnulation B | none | 500 | none | 87 | 99 |
| Formulation B | 0.5% L-77 | 100 | none | 85 | 38 |
| Formulation B | 3.0% L-77 | 100 | none | 68 | 35 |
| Formulation B | none | 100 | 0.5% L-77 | 75 | 48 |
| Formulation B | none | 100 | 3.0% L-77 | 70 | 68 |
| Formulation B | 0.5% FC-129 | 100 | none | 25 | 30 |
| Formulation B | 3.0% FC-129 | 100 | none | 70 | 43 |
| Formulation B | none | 100 | 0.5% FC-129 | 83 | 55 |
| Formulation B | none | 100 | 3.0% FC-129 | 55 | 78 |
| Formulation B | 0.5% FC-135 | 100 | none | 70 | 78 |
| Formulation B | 3.0% FC-135 | 100 | none | 73 | 73 |
| Formulation B | none | 100 | 0.5% FC-135 | 63 | 80 |
| Formulation B | none | 100 | 3.0% FC-135 | 63 | 73 |
| Formulation B | 0.5% Kinetic | 100 | none | 35 | 43 |
| Formulation B | 3.0% Kinetic | 100 | none | 75 | 38 |
| Formulation B | none | 100 | 0.5% Kinetic | 55 | 84 |
| Formulation B | none | 100 | 3.0% Kinetic | 55 | 73 |
| Formulation B | FC-129 + L-77 (1:49) at 0.5% | 100 | none | *75 | 40 |
| Formulation B | FC-129 + L-77 (1:49) at 3.0% | 100 | none | 75 | 35 |
| Formulation B | none | 100 | FC-129 + L-77 (1:49) at 0.5% | 74 | 89 |
| Formulation B | none | 100 | FC-129 + L-77 (1:49) at 3.0% | 55 | 73 |
| Formulation B | FC-129 + L-77 (1:19) at 0.5% | 100 | none | 88 | 33 |
| Formulation B | FC-129 + L-77 (1:19) at 3.0% | 100 | none | 78 | 43 |
| Formulation B | none | 100 | FC-129 + L-77 (1:19) at 0.5% | 74 | 60 |
| Formulation B | none | 100 | FC-129 + L-77 (1:19) at 3.0% | 55 | 73 |
| Formulation B | FC-129 + L-77 (1:9) at 0.5% | 100 | none | 90 | 33 |
| Formulation B | FC-129 + L-77 (1:9) at 3.0% | 100 | none | 75 | 35 |

TABLE 41b-continued

| Initial application 93 l/ha, 0.09% MON-0818 | | Subsequent Glyphosate application 93 l/ha | | % Inhibition | |
|---|---|---|---|---|---|
| herbicide | accession agent | rate g a.e./ha | accession agent at 4 hrs | ABUTH | ECHF |
| Formulation B | none | 100 | FC-129 + L-77 (1:9) at 0.5% | 80 | 50 |
| Formulation B | none | 100 | FC-129 + L-77 (1:9) at 3.0% | 60 | 55 |

Example 42

A field test was conducted to confirm the practical effectiveness of the method of the present invention. Weed species were seeded in rows on a farm in Arkansas. The following naturally occurring weed species were used in evaluating treatments of this Example: A, henbit (*Lamium amplexicaule*, LAMAM); B, shepherd's purse (*Capsella bursa-pastoris*, CAPBP); C, small-flowered bittercress (*Cardamine parviflora*, CARPA); D, annual bluegrass (*Poa annua*, POAAN); E, little barley (*Hordeum pusillum*, HORPU).

After emergence of the weeds, rectangular plots, each 2 m wide and about 9 m long, were marked out for herbicide treatments. A randomized complete block experimental design with four replicates was used. One set of plots in each block was left untreated as a reference against which effects of the treatments could later be evaluated.

Initial applications were made when LAMAM, CAPBP and POAAN were in the early bloom stage, CARPA was in the mid bloom stage and HORPU was at the 3–5 tiller stage. Applications were made using a backpack plot sprayer pressurized with carbon dioxide and fitted with a boom having four 95015 tapered flat fan nozzles with 100-mesh screens. Spraying was conducted at walking speed (approximately 5 km/h), and was calibrated to deliver a spray volume of 93 l/ha at a spray pressure of 193 kPa.

Plants treated according to methods of prior art, for comparative purposes, received an initial treatment only. Plants treated by a method illustrative of the present invention received an initial application of Formulation C followed sequentially by a subsequent application of an accession agent. Two intervals between initial and subsequent applications, about 0.05 hour and 3 hours, were tested in this Example. Subsequent applications were applied by spraying an accession agent with a backpack sprayer fitted exactly as for the initial application and calibrated to deliver a spray volume of 93 l/ha at a pressure of 193 kPa.

Formulation C was applied without accession agent at a range of rates from 157 to 1254 g a.e./ha. When an accession agent was included in the treatment, either in tank mix with Formulation C or as a subsequent application, only the four lowest rates of Formulation C, 157, 314, 420 and 627 g a.e./ha, were tested. This Example uses only one accession agent, an aqueous solution containing 0.5% Silwet L-77. Spray solutions were prepared immediately before application to minimize hydrolytic degradation of Silwet L-77.

Twenty-nine days after the initial application, all plots in the test were examined by a single practiced technician to evaluate percent inhibition. Treatments and corresponding percent inhibitions are given in Table 42. Results shown are an average of the four replicate plots for each treatment.

TABLE 42

| Initial application 93 l/ha | | Subsequent Glyphosate application 93 l/ha | | % Inhibition | | | | |
|---|---|---|---|---|---|---|---|---|
| herbicide | accession agent | rate g a.e./ha | accession agent at 4 hrs | A | B | C | D | E |
| Formulation C | none | 157 | none | 61 | 65 | 76 | 68 | 83 |
| Formulation C | none | 314 | none | 74 | 76 | 84 | 88 | 90 |
| Formulation C | none | 420 | none | 76 | 81 | 94 | 89 | 94 |
| Formulation C | none | 627 | none | 80 | 84 | 94 | 90 | 96 |
| Formulation C | none | 840 | none | 86 | 89 | 96 | 91 | 99 |
| Formulation C | none | 1254 | none | 95 | 94 | 99 | 100 | 100 |
| Formulation C | 0.5% L-77 | 157 | none | 58 | 60 | 65 | 50 | 63 |
| Formulation C | 0.5% L-77 | 314 | none | 69 | 71 | 80 | 60 | 73 |
| Formulation C | 0.5% L-77 | 420 | none | 79 | 81 | 91 | 76 | 85 |
| Formulation C | 0.5% L-77 | 627 | none | 88 | 90 | 98 | 90 | 98 |
| Formulation C | none | 157 | at ~0.05 hr | 70 | 69 | 80 | 68 | 77 |
| Formulation C | none | 314 | at ~0.05 hr | 83 | 85 | 93 | 83 | 93 |
| Formulation C | none | 420 | at ~0.05 hr | 59 | 60 | 68 | 65 | 69 |
| Formulation C | none | 627 | at ~0.05 hr | 64 | 66 | 71 | 71 | 74 |
| Formulation C | none | 157 | at 3 hrs | 65 | 63 | 69 | 63 | 81 |
| Formulation C | none | 314 | at 3hrs | 80 | 83 | 93 | 85 | 94 |
| Formulation C | none | 420 | at 3 hrs | 80 | 85 | 93 | 88 | 96 |
| Formulation C | none | 627 | at 3 hrs | 93 | 90 | 96 | 93 | 99 |

Tank mix application of an accession agent containing Silwet L-77 with Formulation C in this Example antagonized glyphosate activity at low glyphosate rates, with the antagonism being especially marked on POAAN and HORPU, the two grass species evaluated. This test demonstrates that, under field conditions, such antagonism can be reduced or overcome by sequential application of the accession agent after the glyphosate composition according to the method of the present invention.

Example 43

A field test was conducted to confirm the practical effectiveness of the method of the present invention. Weed species were seeded in rows on a farm in southern Alabama. The following species were used in evaluating treatments of this Example: A, henbit (*Lamium amplexicaule*, LAMAM); F, cutleaf evening primrose (*Primula trientalis*, PRITR); G, canola (*Brassica napus*, BRSNC); H, carolina geranium (*Geranium carolinianum*, GERCA); I, wild mustard (*Sinapis arvensis*, SINAR).

After emergence of the weeds, rectangular plots, each 2 m wide in the dimension parallel to the weed rows, and of such a length (~4.5 m) as to extend across all planted rows, were marked out for herbicide treatments. A randomized complete block experimental design with four replicates was used. One set of plots in each block was left untreated as a reference against which effects of the treatments could later be evaluated.

Initial applications were made 64 days after planting, using a backpack plot sprayer pressurized with carbon dioxide and fitted with a boom having four 11002 tapered flat fan nozzles with 50-mesh screens. Spraying was conducted at walking speed (approximately 5 km/h), in a direction perpendicular to the weed rows, and was calibrated to deliver a spray volume of 93 l/ha at a spray pressure of 179 kPa.

Plants treated according to methods of prior art, for comparative purposes, received an initial treatment only. Glyphosate formulations used in this Example included Formulations A, B, C. and J.

Plants treated by a method illustrative of the present invention received an initial application of Formulation A, B, C. or J, followed sequentially one hour later by a subsequent application of an accession agent. Subsequent applications were applied by spraying an accession agent with a backpack sprayer fitted exactly as for the initial application and calibrated to deliver a spray volume of 93 l/ha at a pressure of 179 kPa.

Formulations were applied without accession agent at a range of rates from 314 to 627 g a.e./ha. When an accession agent was included in the treatment, either in tank or as a subsequent application, only the two lowest rates of each formulation, 314 and 420 g a.e./ha, were tested. This Example uses only one accession agent, an aqueous solution containing 0.5% Silwet L-77. Spray solutions were prepared immediately before application to minimize hydrolytic degradation of Silwet L-77.

Twenty-four days after the initial application, all plots in the test were examined by a single practiced technician to evaluate percent inhibition. Treatments and corresponding percent inhibitions are given in Table 43. Results shown are an average of the four replicate plots for each treatment.

TABLE 43

| Initial application 93 l/ha | | Glyphosate rate | Subsequent application, 93 l/ha | % Inhibition | | | | |
|---|---|---|---|---|---|---|---|---|
| herbicide | accession agent | g a.e./ha | accession agent 0.5% L-77 | A | F | G | H | I |
| Formulation A | none | 314 | none | 91 | 64 | 79 | 60 | 76 |
| Formulation A | none | 420 | none | 94 | 75 | 83 | 65 | 83 |
| Formulation A | none | 627 | none | 96 | 78 | 90 | 76 | 90 |
| Formulation A | 0.5% L-77 | 314 | none | 86 | 63 | 69 | 69 | 66 |
| Formulation A | 0.5%L-77 | 420 | none | 91 | 70 | 77 | 68 | 68 |
| Formulation A | none | 314 | at1 hr | 89 | 64 | 74 | 64 | 76 |
| Fonnulation A | none | 420 | at 1 hr | 99 | 71 | 85 | 66 | 88 |
| Formulation B | none | 314 | none | 79 | 70 | 81 | 68 | 76 |
| Formulation B | none | 420 | none | 89 | 69 | 80 | 68 | 85 |
| Formulation B | none | 627 | none | 94 | 80 | 89 | 76 | 91 |
| Formulation B | 0.5% L-77 | 314 | none | 91 | 60 | 73 | 65 | 71 |
| Formulation B | 0.5% L-77 | 420 | none | 98 | 71 | 79 | 70 | 81 |
| Formulation B | none | 314 | at 1 hr | 86 | 63 | 78 | 68 | 75 |
| Formulation B | none | 420 | at 1 hr | 98 | 78 | 85 | 68 | 87 |
| Formulation C | none | 314 | none | 89 | 73 | 79 | 69 | 87 |
| Formulation C | none | 420 | none | 96 | 68 | 88 | 65 | 90 |
| Formulation C | none | 627 | none | 99 | 80 | 89 | 80 | 96 |
| Formulation C | 0.5%L-77 | 314 | none | 93 | 55 | 65 | 66 | 63 |
| Formulation C | 0.5% L-77 | 420 | none | 97 | 70 | 80 | 73 | 71 |
| Formulation C | none | 314 | at 1 hr | 89 | 68 | 80 | 65 | 80 |
| Formulation C | none | 420 | at 1 hr | 97 | 76 | 90 | 74 | 88 |
| Formulation J | none | 314 | none | 81 | 74 | 82 | 66 | 85 |
| Formulation J | none | 420 | none | 93 | 76 | 89 | 65 | 91 |
| Formulation J | none | 627 | none | 93 | 79 | 90 | 75 | 85 |
| Formulation J | 0.5% L-77 | 314 | none | 95 | 70 | 67 | 70 | 66 |
| Formulation J | 0.5% L-77 | 420 | none | 98 | 73 | 82 | 74 | 82 |
| Formulation J | none | 314 | at 1 hr | 93 | 66 | 81 | 68 | 73 |
| Formulation J | none | 420 | at 1 hr | 95 | 73 | 89 | 70 | 87 |

Tank mix application of an accession agent containing Silwet L-77 with all four glyphosate formulations in this Example antagonized glyphosate activity at low glyphosate rates, with the antagonism being especially marked on BRSNC and SINAR. This test demonstrates that, under field conditions, such antagonism can be reduced or overcome by sequential application of the accession agent after the glyphosate composition according to the method of the present invention.

Example 44

A field test was conducted to confirm the practical effectiveness of the method of the present invention. Weed species were seeded in rows on a farm in west central Illinois. The following species were used in evaluating treatments of this Example: I, wild mustard (*Sinapis arvensis*, SINAR); J, wild buckwheat (*Polygonum convolvulus*, POLCO); K, winter wheat (*Triticum aestivum*, TRZAW); L, wild oat (*Avena fatua*, AVEFA); M, annual ryegrass (*Lolium multiflorum*, LOLMU), N, giant foxtail (*Setaria faberi*, SETFA); O, redroot pigweed (*Amaranthus retroflexus*, AMARE).

After emergence of the weeds, rectangular plots, each 2 m wide in the dimension parallel to the weed rows, and of such a length (~6.5 m) as to extend across all planted rows, were marked out for herbicide treatments. A randomized complete block experimental design with three replicates was used. One set of plots in each block was left untreated as a reference against which effects of the treatments could later be evaluated.

Initial applications were made 53 days after planting, using a backpack plot sprayer pressurized with carbon dioxide and fitted with a boom having four 80015 tapered flat fan nozzles with 50-mesh screens. Spraying was conducted at walking speed (approximately 5 km/h), in a direction perpendicular to the weed rows, and was calibrated to deliver a spray volume of 93 l/ha at a spray pressure of 193 kPa.

Plants treated according to methods of prior art, for comparative purposes, received an initial treatment only. Glyphosate formulations used in this Example included Formulations A, B, C and J.

Plants treated by a method illustrative of the present invention received an initial application of Formulation A, B, C or J, followed sequentially one hour later by a subsequent application of an accession agent. Subsequent applications were applied by spraying an accession agent with a backpack sprayer fitted exactly as for the initial application and calibrated to deliver a spray volume of 93 l/ha at a pressure of 193 kPa.

Formulations were applied without accession agent at a range of rates from 157 to 627 g a.e./ha. When an accession agent was included in the treatment, either in tank or as a subsequent application, only the two lowest rates of each formulation, 157 and 314 g a.e./ha, were tested. This Example uses only one accession agent, an aqueous solution containing 0.5% Silwet L-77. Spray solutions were prepared immediately before application to minimize hydrolytic degradation of Silwet L-77.

Twenty-one days after the initial application, all plots in the test were examined by a single practiced technician to evaluate percent inhibition. Treatments and corresponding percent inhibitions are given in Table 44. Results shown are an average of the three replicate plots for each treatment.

TABLE 44

| Initial application 93 l/ha | | Glyphosate | Subsequent application, 93 l/ha | % Inhibition | | | | | | |
|---|---|---|---|---|---|---|---|---|---|---|
| herbicide | accession agent | rate g a.e./ha | accession agent 0.5% L-77 | I | J | K | L | M | N | O |
| Formul'n A | none | 157 | none | 23 | 12 | 28 | 50 | 45 | 57 | 20 |
| Formul'n A | none | 314 | none | 35 | 18 | 68 | 85 | 70 | 83 | 50 |
| Formul'n A | none | 420 | none | 55 | 35 | 87 | 97 | 82 | 90 | 68 |
| Formul'n A | none | 627 | none | 87 | 65 | 98 | 99 | 91 | 93 | 82 |
| Formul'n A | 0.5% L-77 | 157 | none | 53 | 62 | 52 | 67 | 60 | 72 | 40 |
| Formul'n A | 0.5% L-77 | 314 | none | 85 | 87 | 89 | 98 | 83 | 94 | 73 |
| Formul'n A | none | 157 | at 1 hr | 53 | 37 | 57 | 77 | 57 | 75 | 43 |
| Formul'n A | none | 314 | at 1 hr | 70 | 47 | 91 | 97 | 88 | 90 | 73 |
| Formul'n B | none | 157 | none | 30 | 17 | 25 | 45 | 40 | 63 | 28 |
| Formul'n B | none | 314 | none | 37 | 20 | 47 | 67 | 65 | 73 | 40 |
| Formul'n B | none | 420 | none | 53 | 30 | 40 | 67 | 70 | 75 | 53 |
| Formul'n B | none | 627 | none | 77 | 55 | 78 | 80 | 82 | 91 | 75 |
| Formul'n B | 0.5% L-77 | 157 | none | 72 | 77 | 62 | 82 | 72 | 77 | 47 |
| Formul'n B | 0.5% L-77 | 314 | none | 75 | 82 | 94 | 93 | 78 | 87 | 63 |
| Formul'n B | none | 157 | at 1 hr | 32 | 23 | 18 | 40 | 33 | 47 | 25 |
| Formul'n B | none | 314 | at 1 hr | 62 | 42 | 47 | 77 | 67 | 77 | 47 |
| Formul'n C | none | 157 | none | 35 | 12 | 55 | 75 | 65 | 78 | 43 |
| Formul'n C | none | 314 | none | 63 | 32 | 84 | 96 | 82 | 85 | 68 |
| Formul'n C | none | 420 | none | 62 | 30 | 92 | 100 | 83 | 82 | 53 |
| Formul'n C | none | 627 | none | 87 | 75 | 98 | 100 | 91 | 93 | 80 |
| Formul'n C | 0.5% L-77 | 157 | none | 45 | 53 | 42 | 65 | 62 | 72 | 40 |
| Formul'n C | 0.5% L-77 | 314 | none | 75 | 65 | 52 | 85 | 78 | 85 | 68 |
| Formul'n C | none | 157 | at 1 hr | 40 | 32 | 43 | 80 | 57 | 75 | 33 |
| Formul'n C | none | 314 | at 1 hr | 63 | 47 | 95 | 99 | 83 | 90 | 70 |
| Formul'n J | none | 157 | none | 30 | 17 | 73 | 89 | 73 | 83 | 60 |
| Formul'n J | none | 314 | none | 37 | 23 | 85 | 96 | 87 | 88 | 52 |
| Formul'n J | none | 420 | none | 68 | 55 | 98 | 100 | 94 | 92 | 68 |
| Formul'n J | none | 627 | none | 75 | 65 | 100 | 98 | 95 | 92 | 70 |

TABLE 44-continued

| Initial application 93 l/ha | | Glyphosate | Subsequent application, 93 l/ha | | | | | | | |
|---|---|---|---|---|---|---|---|---|---|---|
| | accession | rate | accession agent | % Inhibition | | | | | | |
| herbicide | agent | g a.e./ha | 0.5% L-77 | I | J | K | L | M | N | O |
| Formul'n J | 0.5% L-77 | 157 | none | 63 | 43 | 57 | 78 | 60 | 77 | 30 |
| Formul'n J | 0.5% L-77 | 314 | none | 73 | 85 | 82 | 92 | 80 | 92 | 60 |
| Formul'n J | none | 157 | at 1 hr | 37 | 22 | 63 | 77 | 68 | 75 | 35 |
| Formul'n J | none | 314 | at 1 hr | 68 | 50 | 92 | 98 | 88 | 92 | 72 |

Example 45

A field test was conducted to confirm the practical effectiveness of the method of the present invention. Weed species were seeded in rows on a farm in Arkansas. The following species were used in evaluating treatments of this Example: I, wild mustard (*Sinapis arvensis*, SINAR); M, annual ryegrass (*Lolium multiflorum*, LOLMU); P, downy broom (*Bromus tectorum*, BROTE); Q, cutleaf geranium (*Geranium dissectum*, GERDI); R, curly dock (*Rumex crispus*, RUMCR).

After emergence of the weeds, rectangular plots, each 2 m wide in the dimension parallel to the weed rows, and of such a length (~4.5 m) as to extend across all planted rows, were marked out for herbicide treatments. A randomized complete block experimental design with four replicates was used. One set of plots in each block was left untreated as a reference against which effects of the treatments could later be evaluated.

Initial applications were made 62 days after planting, using a backpack plot sprayer pressurized with carbon dioxide and fitted with a boom having four 95015 tapered flat fan nozzles with 100-mesh screens. Spraying was conducted at walking speed (approximately 5 km/h), in a direction perpendicular to the weed rows, and was calibrated to deliver a spray volume of 93 l/ha at a spray pressure of 193 kPa.

Plants treated according to methods of prior art, for comparative purposes, received an initial treatment only. Glyphosate formulations used in this Example included Formulations A, B, C and J.

Plants treated by a method illustrative of the present invention received an initial application of Formulation A, B, C or J, followed sequentially five hours later by a subsequent application of an accession agent. Subsequent applications were applied by spraying an accession agent with a backpack sprayer fitted exactly as for the initial application and calibrated to deliver a spray volume of 93 l/ha at a pressure of 193 kPa.

Formulations were applied without accession agent at a range of rates from 314 to 840 g a.e./ha. When an accession agent was included in the treatment, either in tank or as a subsequent application, only two rates of each formulation, 420 and 627 g a.e./ha, were tested. This Example uses only one accession agent, an aqueous solution containing 0.5% Silwet L-77. Spray solutions were prepared immediately before application to minimize hydrolytic degradation of Silwet L-77.

Twenty days after the initial application, all plots in the test were examined by a single practiced technician to evaluate percent inhibition. Treatments and corresponding percent inhibitions are given in Table 45. Results shown are an average of the four replicate plots for each treatment.

TABLE 45

| Initial application 93 l/ha | | Glyphosate | Subsequent application, 93 l/ha | | | | | |
|---|---|---|---|---|---|---|---|---|
| | accession | rate | accession agent | % Inhibition | | | | |
| herbicide | agent | g a.e./ha | 0.5% L-77 | I | M | P | Q | R |
| Formulation A | none | 314 | none | 83 | 55 | 73 | 65 | 68 |
| Formulation A | none | 420 | none | 98 | 75 | 88 | 90 | 84 |
| Formulation A | none | 627 | none | 96 | 80 | 88 | 95 | 91 |
| Formulation A | none | 840 | none | 100 | 85 | 94 | 96 | 95 |
| Formulation A | 0.5% L-77 | 420 | none | 93 | 63 | 73 | 91 | 88 |
| Formulation A | 0.5% L-77 | 627 | none | 95 | 80 | 93 | 93 | 88 |
| Formulation A | none | 420 | at 5 hrs | 63 | 48 | 58 | 58 | 50 |
| Formulation A | none | 627 | at 5 hrs | 93 | 81 | 95 | 95 | 83 |
| Formulation B | none | 314 | none | 83 | 45 | 63 | 58 | 55 |
| Formulation B | none | 420 | none | 88 | 58 | 78 | 80 | 79 |
| Formulation B | none | 627 | none | 93 | 63 | 83 | 88 | 88 |
| Formulation B | none | 840 | none | 93 | 78 | 88 | 95 | 90 |
| Formulation B | 0..5% L-77 | 420 | none | 83 | 50 | 65 | 80 | 75 |
| Formulation B | 0.5% L-77 | 627 | none | 98 | 71 | 86 | 96 | 88 |
| Formulation B | none | 420 | at 5 hrs | 88 | 55 | 76 | 81 | 75 |
| Formulation B | none | 627 | at 5 hrs | 98 | 70 | 83 | 96 | 94 |
| Formulation C | none | 314 | none | 80 | 58 | 83 | 55 | 58 |
| Formulation C | none | 420 | none | 95 | 78 | 93 | 89 | 88 |
| Formulation C | none | 627 | none | 100 | 80 | 90 | 100 | 95 |
| Formulation C | none | 840 | none | 100 | 93 | 95 | 100 | 95 |

TABLE 45-continued

| Initial application 93 l/ha | | Glyphosate | Subsequent application, 93 1/ha | | | | | |
|---|---|---|---|---|---|---|---|---|
| herbicide | accession agent | rate g a.e./ha | accession agent 0.5% L-77 | % Inhibition | | | | |
| | | | | I | M | P | Q | R |
| Formulation C | 0.5% L-77 | 420 | none | 85 | 60 | 65 | 70 | 70 |
| Formulation C | 0.5% L-77 | 627 | none | 90 | 78 | 86 | 94 | 78 |
| Formulation C | none | 420 | at 5 hrs | 88 | 68 | 88 | 85 | 83 |
| Formulation C | none 627 | at 5 hrs | 95 | 79 | 93 | 93 | 85 | |
| Formulation J | none | 314 | none | 83 | 65 | 86 | 68 | 73 |
| Formulation J | none | 420 | none | 98 | 85 | 96 | 90 | 88 |
| Formulation J | none | 627 | none | 98 | 85 | 95 | 96 | 90 |
| Formulation J | none | 840 | none | 100 | 94 | 98 | 100 | 96 |
| Formulation J | 0.5% L-77 | 420 | none | 83 | 63 | 73 | 84 | 66 |
| Formulation J | 0.5% L-77 | 627 | none | 95 | 73 | 89 | 90 | 91 |
| Formulation J | none | 420 | at 5 hrs | 90 | 73 | 88 | 88 | 80 |
| Formulation J | none | 627 | at 5 hrs | 100 | 85 | 98 | 96 | 93 |

Example 46

A field test was conducted to confirm the practical effectiveness of the method of the present invention. Weed species were seeded in rows on a farm in southern Alabama. The following species were used in evaluating treatments of this Example: S, broadleaf signalgrass (*Brachiaria platyphylla*, BRAPP); T, barnyardgrass (*Echinochloa crusgalli*, ECHCG); U, johnsongrass (*Sorghum halepense*, SORHA); V, prickly sida (*Sida spinosa*, SIDSP); W, pigweed (*Amaranthus sp.*, AMASS); X, velvetleaf (*Abutilon theophrasti*, ABUTH); Y, hemp sesbania (*Sesbania exaltata*, SEBEX); Z, sicklepod (*Cassia obtusifolia*, CASOB); AA, pitted morningglory (*Ipomoea lacunosa*, IPOLA).

After emergence of the weeds, rectangular plots, each 2 m wide in the dimension parallel to the weed rows, and of such a length (~4.5 m) as to extend across all planted rows, were marked out for herbicide treatments. A randomized complete block experimental design with four replicates was used. One set of plots in each block was left untreated as a reference against which effects of the treatments could later be evaluated.

Initial applications were made 14 days after planting, using a backpack plot sprayer pressurized with carbon dioxide and fitted with a boom having four 11002 tapered flat fan nozzles with 50-mesh screens. Spraying was conducted at walking speed (approximately 5 km/h), in a direction perpendicular to the weed rows, and was calibrated to deliver a spray volume of 93 l/ha at a spray pressure of 193 kPa.

Plants treated according to methods of prior art, for comparative purposes, received an initial treatment only. Glyphosate formulations used in this Example included Formulations A, B, C and J.

Plants treated by a method illustrative of the present invention received an initial application of Formulation A, B, C or J, followed sequentially four hours later by a subsequent application of an accession agent. Subsequent applications were applied by spraying an accession agent with a backpack sprayer fitted exactly as for the initial application and calibrated to deliver a spray volume of 93 l/ha at a pressure of 193 kPa.

Formulations were applied without accession agent at a range of rates from 420 to 1265 g a.e./ha. When an accession agent was included in the treatment, either in tank or as a subsequent application, only two rates of each formulation, 420 and 627 g a.e./ha, were tested. This Example uses only one accession agent, an aqueous solution containing 0.5% Silwet L-77. Spray solutions were prepared immediately before application to minimize hydrolytic degradation of Silwet L-77.

Twenty-six days after the initial application, all plots in the test were examined by a single practiced technician to evaluate percent inhibition. Treatments and corresponding percent inhibitions are given in Table 46a and 46b. Results shown are an average of the four replicate plots for each treatment.

TABLE 46a

| Initial application 93 l/ha | | Glyphosate | Subsequent application, 93 1/ha | | | | | |
|---|---|---|---|---|---|---|---|---|
| herbicide | accession agent | rate g a.e./ha | accession agent 0.5% L-77 | % Inhibition | | | | |
| | | | | S | T | U | V | W |
| Formulation A | none | 420 | none | 91 | 91 | 96 | 91 | 97 |
| Formulation A | none | 627 | none | 95 | 90 | 98 | 97 | 98 |
| Formulation A | none | 1 265 | none | 93 | 93 | 96 | 100 | 98 |
| Formulation A | 0.5% L-77 | 420 | none | 90 | 88 | 98 | 99 | 99 |
| Formulation A | 0.5% L-77 | 627 | none | 95 | 91 | 99 | 97 | 98 |
| Formulation A | none | 420 | at 4 hrs | 91 | 92 | 95 | 100 | 96 |
| Formulation A | none | 627 | at 4 hrs | 92 | 94 | 98 | 99 | 97 |
| Formulation B | none | 420 | none | 89 | 82 | 91 | 96 | 94 |

TABLE 46a-continued

| Initial application 93 l/ha | | | Subsequent application, 93 l/ha | | | | | |
|---|---|---|---|---|---|---|---|---|
| | accession | rate | accession agent | % Inhibition | | | | |
| herbicide | agent | g a.e./ha | 0.5% L-77 | S | T | U | V | W |
| Formulation B | none | 627 | none | 92 | 88 | 95 | 99 | 98 |
| Formulation B | none | 1265 | none | 96 | 97 | 99 | 100 | 100 |
| Formulation B | 0.5% L-77 | 420 | none | 89 | 88 | 91 | 99 | 95 |
| Formulation B | 0.5% L-77 | 627 | none | 90 | 88 | 95 | 99 | 94 |
| Formulation B | none | 420 | at4hrs | 91 | 83 | 90 | 95 | 93 |
| Formulation B | none | 627 | at 4 hrs | 94 | 87 | 89 | 95 | 96 |
| Formulation C | none | 420 | none | 90 | 91 | 96 | 92 | 95 |
| Formulation C | none | 627 | none | 94 | 96 | 98 | 97 | 97 |
| Formulation C | none | 1265 | none | 99 | 99 | 100 | 100 | 99 |
| Formulation C | 0.5% L-77 | 420 | none | 89 | 85 | 96 | 94 | 92 |
| Formulation C | 0.5% L-77 | 627 | none | 92 | 92 | 96 | 96 | 95 |
| Formulation C | none | 420 | at 4 hrs | 92 | 93 | 97 | 97 | 98 |
| Formulation C | none | 627 | at 4 hrs | 92 | 90 | 97 | 95 | 95 |
| Formulation J | none | 420 | none | 90 | 92 | 95 | 94 | 94 |
| Formulation J | none | 627 | none | 93 | 95 | 95 | 99 | 99 |
| Formulation J | none | 1265 | none | 95 | 96 | 98 | 100 | 99 |
| Formulation J | 0.5% L-77 | 420 | none | 88 | 84 | 93 | 97 | 94 |
| Formulation J | 0.5% L-77 | 627 | none | 88 | 89 | 94 | 99 | 95 |
| Formulation J | none | 420 | at 4 hrs | 94 | 92 | 95 | 92 | 95 |
| Formulation J | none | 627 | at 4 hrs | 96 | 98 | 99 | 100 | 99 |

TABLE 46b

| Initial application 93 l/ha | | | Subsequent application, 93 l/ha | | | | |
|---|---|---|---|---|---|---|---|
| | accession | rate | accession agent | % Inhibition | | | |
| herbicide | agent | g a.e./ha | 0.5% L-77 | X | Y | Z | AA |
| Formulation A | none | 420 | none | 79 | 90 | 91 | 65 |
| Formulation A | none | 627 | none | 88 | 97 | 94 | 79 |
| Formulation A | none | 1265 | none | 96 | 100 | 99 | 89 |
| Formulation A | 0.5% L-77 | 420 | none | 97 | 94 | 90 | 68 |
| Formulation A | 0.5% L-77 | 627 | none | 94 | 96 | 93 | 82 |
| Formuiation A | none | 420 | at 4 hrs | 90 | 90 | 93 | 60 |
| Formulation A | none | 627 | at 4 hrs | 94 | 96 | 96 | 78 |
| Formulation B | none | 420 | none | 83 | 56 | 78 | 71 |
| Formulation B | none | 627 | none | 86 | 71 | 88 | 71 |
| Formulation B | none | 1265 | none | 97 | 89 | 93 | 90 |
| Formulation B | 0.5% L-77 | 420 | none | 93 | 83 | 85 | 69 |
| Formulation B | 0.5% L-77 | 627 | none | 95 | 93 | 92 | 77 |
| Formulation B | none | 420 | at 4 hrs | 89 | 54 | 74 | 65 |
| Formulation B | none | 627 | at 4 hrs | 94 | 67 | 77 | 70 |
| Formulation C | none | 420 | none | 82 | 90 | 92 | 71 |
| Formulation C | none | 627 | none | 91 | 96 | 97 | 73 |
| Formulation C | none | 1265 | none | 95 | 99 | 100 | 94 |
| Formulation C | 0.5% L-77 | 420 | none | 91 | 93 | 90 | 58 |
| Formulation C | 0.5 % L-77 | 627 | none | 85 | 90 | 93 | 63 |
| Formulation C | none | 420 | at 4 hrs | 92 | 92 | 92 | 61 |
| Formulation C | none | 627 | at 4 hrs | 94 | 94 | 95 | 64 |
| Formulation J | none | 420 | none | 84 | 93 | 93 | 66 |
| Formulation J | none | 627 | none | 92 | 98 | 99 | 82 |
| Formulation J | none | 1265 | none | 98 | 100 | 97 | 85 |
| Formulation J | 0.5% L-77 | 420 | none | 93 | 89 | 90 | 59 |
| Formulation J | 0.5% L-77 | 627 | none | 95 | 98 | 98 | 63 |
| Formulation J | none | 420 | at 4 hrs | 91 | 93 | 93 | 63 |
| Formulation J | none | 627 | at 4 hrs | 96 | 94 | 95 | 68 |

The present invention may also be embodied in specific modes other than those set forth in the foregoing specification, without departing from the spirit or essential attributes of the invention. Accordingly, reference should be made to the appended claims, rather than the foregoing specification, as indicating the scope of the invention.

What is claimed is:

1. A herbicidal method comprising sequentially the steps of (a) contacting a plant with a herbicide comprising N-phosphonomethylglycine or a herbicidal derivative thereof and (b) thereafter contacting the plant with an accession agent whereby any antagonism to herbicidal effectiveness that would be exhibited were the plant contacted with a tank mix or coformulation of the herbicide and the accession agent is substantially reduced.

2. A method for enhancing the herbicidal effectiveness of a herbicide for a plurality of plant species in a field comprising the steps of (a) applying to the plurality of plant species in the field a herbicide comprising N-phosphonomethylglycine or a herbicidal derivative thereof and (b) thereafter applying to the plurality of plant species an accession agent, whereby the herbicidal effectiveness of the herbicide for at least one of the plurality of plant species is substantially enhanced.

3. A method for reducing the antagonism of an accession agent to the herbicidal effectiveness of a herbicide comprising N-phosphonomethylglycine or a herbicidal derivative thereof comprising the steps (a) applying the herbicide to a plant species for which the accession agent is antagonistic to the herbicidal effectiveness of the herbicide when tank mixed or coformulated therewith and (b) thereafter applying to the plant species an accession agent, whereby the herbicidal effectiveness of the herbicide for the plant species is substantially preserved or enhanced.

4. The method as in any one of claims 1–3 wherein the herbicide comprises a water soluble salt of N-phosphonomethylglycine.

5. The method of claim 4 wherein the herbicide comprises a salt selected from the group consisting of ammonium, alkylamine, alkali metal, alkylsulfonium, and sulfoxonium salts of N-phosphonomethylglycine.

6. The method of claim 5 wherein the herbicide comprises an alkali metal salt of N-phosphonomethylglycine.

7. The method of claim 6 wherein the herbicide comprises the monosodium salt of N-phosphonomethylglycine.

8. The method of claim 5 wherein the herbicide comprises an ammonium or an alkylamine salt of N-phosphonomethylglycine.

9. The method of claim 8 wherein the herbicide comprises the monoisopropylamine salt of N-phosphonomethylglycine.

10. The method of claim 9 wherein the herbicide further comprises a surfactant.

11. The method of claim 10 wherein the surfactant is a tertiary or quaternary polyoxyalkylene alkylamine.

12. The method of claim 11 wherein the surfactant is a polyethoxylated tallowamine.

13. The method of claim 12 wherein the accession agent is an aqueous solution of a surfactant.

14. The method of claim 13 wherein the accession agent is an aqueous solution of a superwetting surfactant.

15. The method of claim 14 wherein the superwetting surfactant is selected from the group consisting of organosilicone wetting agents and fluoro-organic wetting agents.

16. The method of claim 15 wherein the superwetting surfactant is an organosilicone wetting agent.

17. The method of claim 16 wherein the superwetting surfactant is an organosilicone wetting agent of the following average formula:

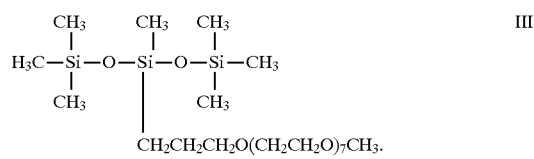

18. The method of claim 17 wherein the concentration of the surfactant in the aqueous solution is at least about 0.25% by volume.

19. The method of claim 18 wherein the concentration of the surfactant in the aqueous solution is at least about 0.50% by volume.

20. The method of claim 15 wherein the superwetting surfactant is a fluoro-organic wetting agent.

21. The method of claim 20 wherein the superwetting surfactant is a fluoroalkyl quaternary ammonium iodide surfactant.

22. The method of claim 21 wherein the concentration of the surfactant in the aqueous solution is at least about 0.25% by volume.

23. The method of claim 22 wherein the concentration of the surfactant in the aqueous solution is at lest about 0.50% by volume.

24. The method as in any one of claims 1–3 wherein the accession agent is an aqueous solution of a superwetting surfactant.

25. The method of claim 24 wherein the superwetting surfactant is selected from the group consisting of organosilicone wetting agents and fluoro-organic wetting agents.

26. The method of claim 25 wherein the superwetting surfactant is an organosilicone wetting agent.

27. The method of claim 26 wherein the superwetting surfactant is an organosilicone wetting agent for the following average formula:

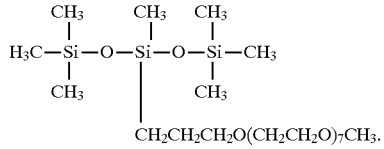

28. The method of claim 25 wherein the superwetting surfactant is a fluoro-organic wetting agent.

29. The method of claim 28 wherein the superwetting surfactant is a fluoroalkyl quaternary ammonium iodide surfactant.

30. The method as in any one of claims 1–3 wherein the herbicide further comprises a surfactant.

31. The method of claim 30 wherein the surfactant in the herbicide is a tertiary or quaternary polyoxyalkylene alkylamine.

32. The method of claim 31 wherein the surfactant in the herbicide is a polyethoxylated tallows amine.

33. A herbicidal method comprising sequentially the steps of (a) contacting a plant with a herbicide comprising a water soluble salt of N-phosphonomethylglycine and (b) thereafter contacting the plant with an aqueous solution containing at least about 0.50% by volume of a superwetting surfactant selected from the group consisting of organosilicone wetting agents and fluoro-organic wetting agents, whereby any antagonism to herbicidal effectiveness that would be exhibited were the plant contacted with a tank mix or coformulation of the herbicide and the superwetting surfactant is substantially reduced.

34. A method for enhancing the herbicidal effectiveness of a herbicide for a plurality of plant species in a field comprising the steps of (a) applying to the plurality of plant species in the field a herbicide comprising a water soluble salt of N-phosphonomethyl-glycine and (b) thereafter applying to the plurality of plant species an aqueous solution containing at least about 0.50% by volume of a superwetting surfactant selected from the group consisting of organosilicone wetting agents and fluoro-organic wetting agents, whereby the herbicidal effectiveness of the herbicide is substantially enhanced for at least one of the plurality of plant species.

35. The method as in either of claims 33–34 wherein the herbicide further comprises a surfactant.

36. The method as in claim 35 wherein the surfactant in the herbicide is a tertiary or quaternary polyoxyalkylene alkylamine.

37. The method of claim 36 wherein the surfactant in the herbicide is a polyethoxylated tallowamine.

38. The method of claim 1 wherein the plant is contacted with the accession agent during a period of time ranging from immediately after up to about 24 hours after contacting the plant with the herbicide.

39. The method as in either of claims 2–3 wherein the accession agent is applied during a period of time ranging from immediately after up to about 24 hours after application of the herbicide.

40. The method of claim 33 wherein the plant is contacted with the aqueous solution of superwetting surfactant during a period of time ranging from immediately after up to about 24 hours after contacting the plant with the herbicide.

41. The method of claim 34 wherein the aqueous solution of superwetting surfactant is applied during a period of time ranging from immediately after to about 24 hours after application of the herbicide.

42. The method as in either of claim 38 or 40 wherein the period of time is from about one hour up to about three hours after contacting the plant with the herbicide.

43. The method of claim 39 wherein the period of time is from about one hour to about three hours after application of the herbicide.

44. The method of claim 41 wherein the period of time is from about one hour to about three hours after application of the herbicide.

45. The method as in either claim 38 or 40 wherein the period of time is from about 0.05 to about 10 seconds after contacting the plant with the herbicide.

46. The method of claim 39 wherein the period of time is from about 0.05 to about 10 seconds after application of the herbicide.

47. The method of claim 41 wherein the period of time is from about 0.05 to about 10 seconds after application of the herbicide.

48. The method as in any one of claims 1–3 or 33–34 wherein the herbicide effectively controls one or more plant species of one or more of the following genera:

Abutilon, Amaranthus, Artemisia, Asclepias, Avena, Axonopus, Borreria, Brachiaria, Brassica, Bromus, Chenopodium, Cirsium, Commelina, Convolvulus, Cynodon, Cyperus, Digitaria, Echinochloa, Eleusine, Elymus, Equisetum, Erodium, Helianthus, Imperata, Ipomoea, Kochia, Lolium, Malva, Oryza, Ottochloa, Panicum, Paspalum, Phalaris, Phragmites, Polygonum, Portulaca, Pteridium, Pueraria, Rubus, Salsola, Setaria, Sida, Sinapis, Sorghum, Triticum, Typha, Ulex, Xanthium, and Zea.

49. The method as in any one of claims 1–3 or 33–34 wherein the herbicide effectively controls one or more of the following plant species:

velvetleaf (*Abutilon theophrasti*)
pigweed (*Amaranthus spp.*)
buttonweed (*Borreria spp.*)
oilseed rape, canola, indian mustard, etc. (*Brassica spp.*)
commelina (*Commelina spp.*)
filaree (*Erodium spp.*)
sunflower (*Helianthus spp.*)
morningglory (*Ipomoea spp.*)
kochia (*Kochia scoparia*)
mallow (*Malva spp.*)
wild buckwheat, smartweed, etc. (*Polygonum spp.*)
purslane (*Portulaca spp.*)
russian thistle (*Salsola spp.*)
sida (*Sida spp.*)
wild mustard (*Sinapis arvensis*)
cocklebur (*Xanthium spp.*)
wild oat (*Avena fatua*)
carpetgrass (*Axonopus spp.*)
downy broom (*Bromus tectorum*)
crabgrass (*Digitaria spp.*)
barnyardgrass (*Echinochloa crus-galli*)
goosegrass (*Eleusine indica*)
annual ryegrass (*Lolium multiflorum*)
rice (*Oryza sativa*)
ottochloa (*Ottochloa nodosa*)
bahiagrass (*Paspalum notatum*)
canarygrass (*Phalaris spp.*)
foxtail (*Setaria spp.*)
wheat (*Triticum aestivum*)
corn (*Zea mays*)
mugwort (*Artemisia spp.*)
milkweed (*Asclepias spp.*)
canada thistle (*Cirsium arvense*)
field bindweed (*Convolvulus arvensis*)
kudzu (*Pueraria spp.*)
brachiaria (*Brachiaria spp.*)
bermudagrass (*Cynodon dactylon*)
yellow nutsedge (*Cyperus esculentus*)
purple nutsedge (*C. rotundus*)
quackgrass (*Elymus repens*)
lalang (*Imperata cylindrica*)
perennial ryegrass (*Lolium perenne*)
guineagrass (*Panicum maximum*)
dallisgrass (*Paspalum dilatatum*)
reed (*Phragmites spp.*)
johnsongrass (*Sorghum halepense*)
cattail (*Typha spp.*)
horsetail (*Equisetum spp.*)
bracken (*Pteridium aquilinum*)
blackberry (*Rubus spp.*)
gorse (*Ulex europaeus*).

50. The method as in any one of claims 1–3 or 33–34 wherein the herbicide effectively controls one or more of the following plant species:

velvetleaf (*Abutilon theophrasti*)
redroot pigweed (*Amaranthus retroflexus*)
wild oat (*Avena fatua*)
broadlead signalgrass (*Brachiaria platyphylla*)
canola (*Brassica napus*)
downy broom (*Bromus tectorum*)
sicklepod (*Cassia obtusifolia*)
common lambsquarter (*Chenopodium album*)
barnyardgrass (*Echinochloa crus-galli*)
redstem filaree (*Erodium cicutarium*)
cutleaf geranium (*Geranium dissectum*)
soybean (*Glycine max*)
little barley (*Hordeum pusillum*)
pitted morning-glory (*Ipomoca lacunosa*)
annual ryegrass (*Lolium multiflorum*)
annual bluegrass (*Poa annua*)

wild buckwheat (*Polygonum convolvulus*)
cutleaf evening primrose (*Primula trientalis*)
curly dock (*Rumex crispus*)
hemp sesbania (*Sesbania exaltata*)
prickly sida (*Sida spinosa*)
wild mustard (*Sinapis arvensis*)
johnsongrass (*Sorghum halepense*)
wheat (*Triticum aestivum*).

51. A method for enhancing the yield of a field crop comprising the steps of:
   (a) planting a crop in a field,
   (b) substantially freeing the field of one or more weed species that would diminish the yield of the crop by
      (i) applying to the weed species a herbicide comprising N-phosphonomethylglycine or a herbicidal derivative thereof and
      (ii) thereafter applying to the weed species an accession agent, whereby any antagonism to herbicidal effectiveness that would be exhibited by application of a tank mix or coformulation of the herbicide and the accession agent is substantially reduced,
   (c) allowing the crop to mature, and
   (d) harvesting the crop.

52. The method of claim 51 wherein the herbicide comprises a water soluble salt of N-phosphonomethylglycine and the accession agent comprises an aqueous solution of a superwetting surfactant selected from the group consisting of organosilicone wetting agents and fluoro-organic wetting agents.

53. The method of claim 52 wherein the herbicide further comprises a surfactant.

54. The method of claim 53 where the surfactant in the herbicide is a tertiary or quaternary polyoxyalkylene alkylamine.

55. The method of 54 wherein the surfactant in the herbicide is a polyethoxylated tallowamine.

56. A method of enhancing the yield of a field crop comprising the steps of:
   (a) selecting a field for planting a crop,
   (b) substantially freeing the field of one or more weed species that would diminish the yield of the crop by:
      (i) applying to the weed species a herbicide comprising N-phosphonomethylglycine or a herbicidal derivative thereof and
      (ii) thereafter applying to the weed species an accession agent, whereby any antagonism to herbicidal effectiveness that would be exhibited by application of a tank mix or coformulation of the herbicide and the accession agent is substantially reduced,
   (c) planting the crop in the field,
   (d) allowing the crop to mature, and
   (e) harvesting the crop.

57. The method of claim 56 wherein the herbicide comprises a water soluble salt of N-phosphonomethylglycine and the accession agent comprises an aqueous solution of a superwetting surfactant selected from the group consisting of organosilicone wetting agents and fluoro-organic wetting agents.

58. The method of claim 57 wherein the herbicide further comprises a surfactant.

59. The method of claim 58 wherein the surfactant in the herbicide is a tertiary or quaternary polyoxyalkylene alkylamine.

60. The method of claim 59 wherein the surfactant in the herbicide is a polyethoxylated tallowamine.

* * * * *

UNITED STATES PATENT AND TRADEMARK OFFICE
CERTIFICATE OF CORRECTION

PATENT NO. : 5,821,195

DATED : October 13, 1998

INVENTOR(S) : Joseph J. Sandbrink, et al

It is certified that error appears in the above-identified patent and that said Letters Patent is hereby corrected as shown below:

At column 2, line 21, delete "Gaskini" and insert in its place --Gaskin--.

At column 3, line 9, delete "broom" and insert in its place --brome--.

At column 3, line 36, delete "broadlead" and insert in its place --broadleaf--.

At column 3, line 38, delete "broom" and insert in its place --brome--.

At column 7, line 49, delete "filarce" and insert in its place --filaree--.

At column 7, line 66, delete "broom" and insert in its place --brome--.

At column 107, line 22, delete "broom" and insert in its place --brome--.

In claim 23, column 114, line 10, delete "lest" and insert in its place --least--.

In claim 32, column 114, lines 39, delete "tallows amine" and insert in its place --tallowamine--.

In claim 49, column 116, line 7, delete "broom" and insert in its place --brome--.

UNITED STATES PATENT AND TRADEMARK OFFICE
CERTIFICATE OF CORRECTION

PATENT NO.   :   5,821,195

DATED        :   October 13, 1998

INVENTOR(S)  :   Joseph J. Sandbrink, et al

It is certified that error appears in the above-identified patent and that said Letters Patent is hereby corrected as shown below:

In claim 50, column 116, line 53, delete "broadlead" and insert in its place --broadleaf--.

In claim 50, column 116, line 56, delete "broom" and insert in its place --brome--.

Signed and Sealed this

Thirtieth Day of March, 1999

Attest:

Q. TODD DICKINSON

*Attesting Officer*            *Acting Commissioner of Patents and Trademarks*